(12) United States Patent
Parikh et al.

(10) Patent No.: US 10,683,328 B2
(45) Date of Patent: *Jun. 16, 2020

(54) INHIBITORS OF METASTASIS

(71) Applicants: BIOMARCK PHARMACEUTICALS LTD, Durham, NC (US); NORTH CAROLINA STATE UNIVERSITY, Raleigh, NC (US)

(72) Inventors: Indu Parikh, Chapel Hill, NC (US); Kenneth B. Adler, Raleigh, NC (US)

(73) Assignees: BIOMARCK PHARMACEUTICALS LTD., Durham, NC (US); NORTH CAROLINA STATE UNIVERSITY, Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/996,797

(22) Filed: Jun. 4, 2018

(65) Prior Publication Data

US 2019/0119320 A1 Apr. 25, 2019

Related U.S. Application Data

(63) Continuation of application No. 15/203,376, filed on Jul. 6, 2016, now Pat. No. 10,011,636, which is a continuation of application No. 14/246,864, filed on Apr. 7, 2014, now Pat. No. 9,408,886.

(60) Provisional application No. 61/808,966, filed on Apr. 5, 2013.

(51) Int. Cl.

| C07K 7/06 | (2006.01) |
|---|---|
| A61K 38/00 | (2006.01) |
| A61K 38/08 | (2019.01) |
| A61K 38/10 | (2006.01) |
| A61K 38/16 | (2006.01) |
| A61K 45/06 | (2006.01) |
| A61K 31/7105 | (2006.01) |
| A61K 38/07 | (2006.01) |
| A61K 31/713 | (2006.01) |
| A61P 35/04 | (2006.01) |
| C12N 15/113 | (2010.01) |

(52) U.S. Cl.
CPC .............. *C07K 7/06* (2013.01); *A61K 31/713* (2013.01); *A61K 31/7105* (2013.01); *A61K 38/07* (2013.01); *A61K 38/08* (2013.01); *A61K 38/10* (2013.01); *A61K 38/16* (2013.01); *A61K 45/06* (2013.01); *A61P 35/04* (2018.01); *A61K 38/00* (2013.01); *C12N 15/113* (2013.01); *C12N 2310/113* (2013.01); *C12N 2310/14* (2013.01); *C12N 2310/141* (2013.01)

(58) Field of Classification Search
None
See application file for complete search history.

(56) References Cited

U.S. PATENT DOCUMENTS

| 9,408,886 B2 * | 8/2016 | Parikh ................ A61K 38/08 |
|---|---|---|
| 10,011,636 B2 * | 7/2018 | Parikh ................ A61K 38/08 |
| 2004/0180836 A1 | 9/2004 | Martin et al. |
| 2006/0205664 A1 | 9/2006 | Parikh et al. |
| 2006/0217307 A1 | 9/2006 | Takashi et al. |
| 2008/0213319 A1 | 9/2008 | Kang et al. |
| 2008/0299654 A1 | 12/2008 | Monahan et al. |
| 2009/0203620 A1 | 8/2009 | Parikh et al. |
| 2009/0220581 A1 | 9/2009 | Li et al. |
| 2010/0003247 A1 | 1/2010 | Petricoin, III et al. |
| 2010/0197607 A1 | 8/2010 | Parikh et al. |
| 2011/0064739 A1 * | 3/2011 | Borlak ................ C12Q 1/6886 424/138.1 |
| 2013/0338085 A1 | 12/2013 | Parikh et al. |
| 2014/0302057 A1 | 10/2014 | Parikh et al. |
| 2017/0121369 A1 | 5/2017 | Parikh et al. |

FOREIGN PATENT DOCUMENTS

| WO | WO 2003/000027 A2 | 1/2003 |
|---|---|---|
| WO | WO 2003/030827 A2 | 4/2003 |
| WO | WO 2007/103368 A2 | 9/2007 |
| WO | WO 2008/057305 A2 | 5/2008 |
| WO | WO 2009/062128 A2 | 5/2009 |
| WO | WO 2011/079015 A1 | 6/2011 |
| WO | WO 2012/139137 A2 | 10/2012 |
| WO | WO 2014/165853 A1 | 10/2014 |

OTHER PUBLICATIONS

Clower, downloaded on Sep. 12, 2019 from URL:<https://time.com/4519760/no-you-cant-prevent-all-cancers/> (Year: 2019).*

Baker and Reddy, "A Key Player in the Cell Cycle, Development, and Cancer." Genes & Cancer (2013); 3(11-12): 658-669.

Butsuri, Seibutsu, "The Role of Protein Myristoylation in Protein-Lipid and Protein-Protein Interactions." Biophysics (2005); 45(3): 128-133 (with English Abstract).

Chen et al. "Protein kinase C substrates that drive motility of cancer cells." The City University of New York (2010).

Chen et al. "A peptide that inhibits function of myristoylated alanine-rich C Kinase Substrate (MARCKS) reduces lung cancer metastasis." Oncogene 33(28) 3696. Epub Aug. 19, 2013.

Chen and Rotenberg, "PhosphoMARCKS drives motility of mouse melanoma cells." Cell Signal. (2010); 22 (7): 1097-1103.

Entschladen et al. "Re-Use of Established Drugs for Anti-Metastatic Indications." Cells 5.1 (2016): 2.

(Continued)

*Primary Examiner* — Sergio Coffa
(74) *Attorney, Agent, or Firm* — Cooley LLP

(57) ABSTRACT

The present invention relates to methods and compounds for treating or preventing cancer. Methods and compositions provided include including inhibiting or suppressing the development, maintenance, and proliferation of cancers, including blocking or inhibiting cancer cell metastasis.

12 Claims, 16 Drawing Sheets

Specification includes a Sequence Listing.

(56) References Cited

OTHER PUBLICATIONS

Hardin et al. "A peptide identical to the N-terminal region of MARCKS protein decreases proliferation of two lung cancer cell lines." Abstract 5964. Poster. American Thoracic Society Meeting 2010.

Ikenoya et al. "Inhibition of Rho-kinase-induced myristoylated alanine-rich C kinase substrate (MARCKS) phosphorylation in human neuronal cells by H-1152, a novel and specific Rho-kinase inhibitor." Journal of Neurochemistry 81.1 (2002): 9-16.

International Application No. PCT/US2014/033206, International Preliminary Report on Patentability dated Oct. 26, 2015.

International Application No. PCT/US2014/033206, International Search Report and Written Opinion dated Sep. 4, 2014.

Jarboe, et al., "MARCKS Regulates Growth and Radiation Sensitivity and Is a Novel Prognostic Factor for Glioma". Clinical Cancer Research (2012); 18(11): 3030-3041.

Ogasawara et al. "Screening of natural compounds for inhibitory activity on colon cancer cell migration." Biological and Pharmaceutical Bulletin 24.6 (2001): 720-723.

Rihani, et al., "Inhibition of CDK4/6 as a novel therapeutic option for neuroblastoma." Cancer Cell International (2015); 15: 76.

Rombouts et al., "Myristoylated Alanine-Rich protein Kinase C Substrate (MARCKS) expression modulates the metastatic phenotype in human and murine colon carcinoma in vitro and in vivo," Cancer Letters 333:244-252 (2013).

Singer, et al., "A MARCKS-related peptide blocks mucus hypersecretion in a mouse model of asthma." Nature Medicine (2004); 10(2): 193-196.

Smith and Adler. "MARCKS and Human Cancer Cell Line Proliferation." College of Veterinary Medicine, NC State University. Poster. Jul. 2012.

Supplementary European Search Report, EP appl. No. 14779844.1, 7 pages (dated Oct. 11, 2016).

Techasen et al., "Myristoylated alanine-rich C kinase substrate phosphorylation promotes cholangiocarcinoma cell migration and metastasis via the protein kinase C-dependent pathway," Cancer Sci. 101:658-665 (2010).

\* cited by examiner

Figure 1
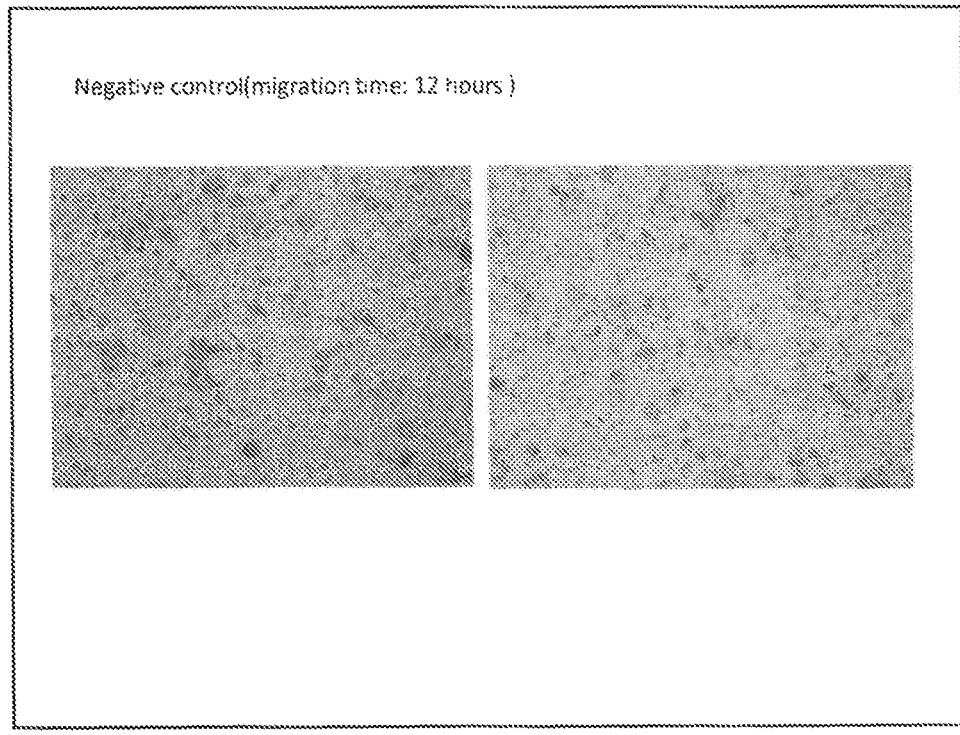
Figure 2A                    Figure 2B
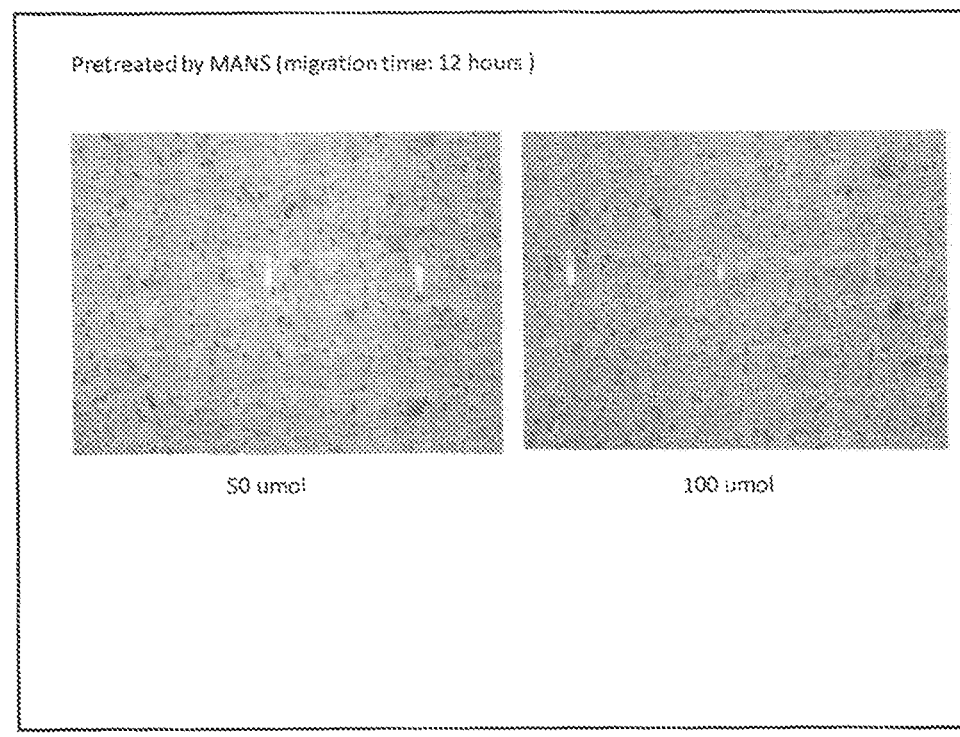

Figure 7A                              Figure 7B
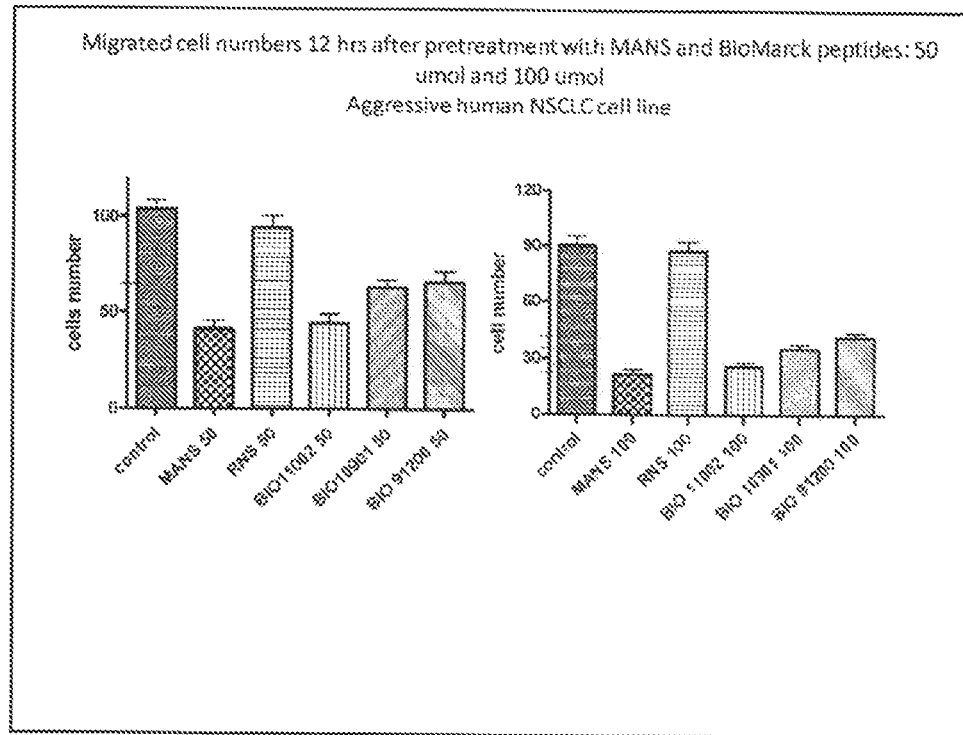
Figure 8A                              Figure 8B
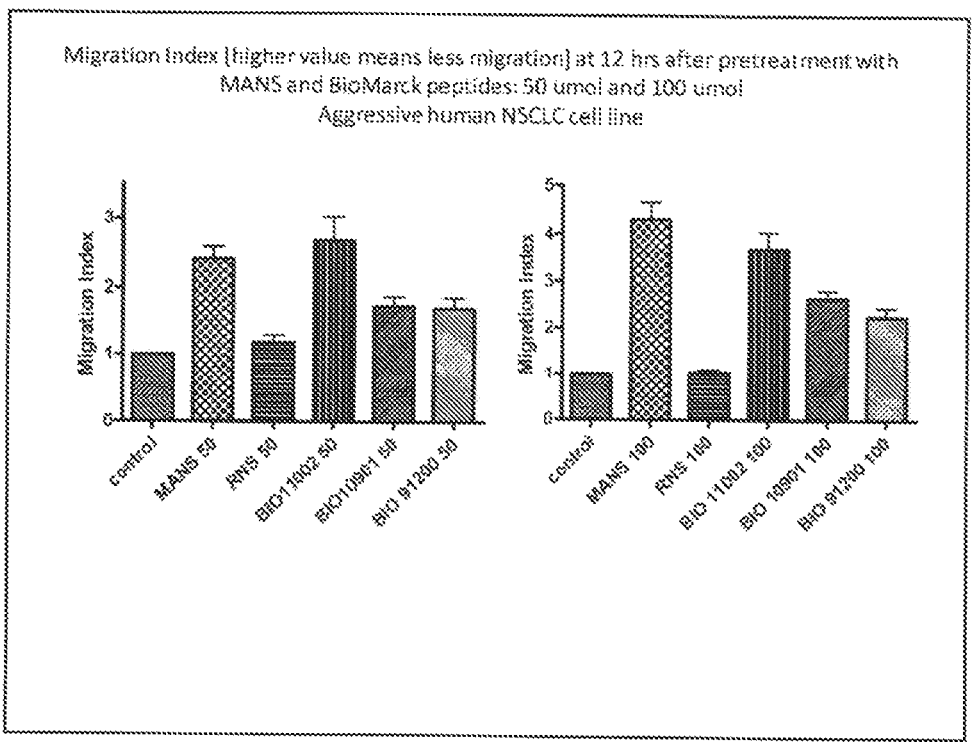

MARCKS protein expression (Y-Axis) is decreased ~60% in PC-9 Cells following siRNA-M treatment. Level of MARCKS protein assessed via Western Blot MARCKS protein expression (Y-Axis) is decreased ~50% in A549 Cells following siRNA-M treatment. Level of MARCKS protein assessed via Western Blot Knockdown of MARCKS in PC-9 cells by MARCKS siRNA resulted in ~ 90% reduction in cell migration A: miR-21 negative control 50nM
B: miR-21 inhibitor 50nM PC9 (P15) cells were transfected with 50nM of negative control (HiPerfect vehicle) or the miR-21 inhibitor. After 48 hours, cell were harvested and protein analysis by Western Blot with MARCKS antibody.

The miR-21 inhibitor increased MARCKS protein expression in PC-9 cells ~ 2.5 fold.

INHIBITORS OF METASTASIS

CROSS REFERENCE TO RELATED APPLICATIONS

This application is a continuation of U.S. application Ser. No. 15/203,376, filed Jul. 6, 2016, now U.S. Pat. No. 10,011,636, which is a continuation of U.S. application Ser. No. 14/246,864, filed Apr. 7, 2014, now U.S. Pat. No. 9,408,886, which claims priority to U.S. Provisional Application No. 61/808,966, filed Apr. 5, 2013, each of which is herein incorporated by reference in its entirety.

FIELD OF THE INVENTION

This invention relates to compositions and formulations comprising antibodies, nucleic acid molecules, polynucleotides and peptides, and methods of their use for the prevention and treatment of metastatic cancers, especially for the reduction, blocking, or inhibition of cancer cell proliferation, metastasis and/or angiogenesis.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: BMRK_006_02US_SubSeqList_ST25.txt, date recorded Sep. 26, 2017, file size 58 kilobytes).

BACKGROUND OF THE INVENTION

MARCKS protein (Myristoylated Alanine-Rich C Kinase Substrate) is a ubiquitous phosphorylation target of protein kinase C (PKC) (Li et al., *Journal of Biological Chemistry* 276; 40982 (2002)). MARCKS has three evolutionarily-conserved regions (Aderem et al., Nature 1988; 332:362-364; Thelen et al., Nature 1991; 351:320-322; Hartwig et al., Nature 1992; 356:618-622; Seykora et al., J Biol Chem 1996; 271:18797-18802): an N-terminus, a phosphorylation site domain (or PSD; also known as the effector domain), and a multiple homology 2 (MH2) domain. The N-terminus, an alpha-amino acid sequence comprising 24 amino acid residues with a myristic acid moiety attached via an amide bond to the N-terminal glycine residue is involved in binding of MARCKS to membranes in cells (Seykora et al., J Biol Chem 1996; 271:18797-18802) and possibly to calmodulin (Matsubara et al., J Biol Chem 2003; 278:48898-48902). This 24 amino acid sequence is known as the MANS peptide. MANS peptide and related peptides are disclosed in U.S. Pat. Nos. 7,265,088; 7,529,926; 7,544,772; 8,492,518; 8,501,911; 7,918,293,870; and 8,563,689; the entire contents of each of which are incorporated by reference in their entireties.

There is a need in the art for new, safe therapies directed to preventing, treating, and inhibiting cancer, including inhibiting cancer cell metastasis, cancer cell proliferation, tumor growth, and/or angiogenesis. The present invention addresses these and other needs.

BRIEF SUMMARY OF THE INVENTION

This invention relates to methods and compositions useful for preventing or treating cancer. In one embodiment, methods and compositions for inhibiting cancer cell metastasis, cancer cell proliferation, tumor growth, or angiogeneis are provided. In one embodiment, methods and compositions for preventing and inhibiting cancer cell metastasis, cancer cell proliferation, tumor growth, or angiogeneis are provided, comprising inhibition of myristoylated alanine-rich C-kinase substrate (MARCKS). In one embodiment, the compositions comprise MARCKS-inhibitory compounds including peptides, polypeptides, antibodies or fragments thereof, and nucleic acid molecules such as antisense polynucleotides, aptamers, small interfering RNA (siRNA), micro RNA (miRNA), and short-hairpin RNA (shRNA). "MARCKS-inhibitory nucleic acid molecules" as used herein refer to polynucleotides or nucleic acid molecules such as siRNA, miRNA, shRNA, or antisense polynucleotides, that reduce expression and/or function of MARCKS. In one embodiment, the compositions comprise one or more MARCKS-related peptides. In another embodiment, the MARCKS-related peptides correspond to the MH2 domain of MARCKS. In another embodiment, the peptides are myristoylated N-terminal sequence (MANS peptide, which is a 24 amino-acid fragment of MARCKS)-related peptides (i.e., "MANS-related peptides"). In a further embodiment, MANS-related peptides are selected from the group consisting of: MANS peptide; unsubstituted fragments of MANS which contain four or more amino acids and which comprise the same sequence found in the N-terminal amino acid sequence in MANS peptide; peptides comprising a sequence substantially identical to the sequence found in the MANS peptide or MANS peptide fragment; MANS peptide or fragments of MANS peptide with the identical or substantially identical amino acid sequence as the MANS peptide that are N-terminal myristoylated or N-terminal acylated with, for example, an acetyl group; and MANS peptide or fragments of MANS peptide with the identical or substantially identical amino acid sequence as the MANS peptide that are C-terminal chemically modified. In one embodiment, the MANS-related peptides are both N-terminal and C-terminal chemically modified. In one embodiment, the MARCKS-inhibitory compounds provided herein are antibodies or fragments thereof. In one embodiment, the antibody or fragment thereof inhibits the functions of the MARCKS protein. In another embodiment, the antibody or fragment thereof binds to the N-terminal of the MARCKS protein or the MH2 sequence of the MARCKS protein. We have found surprisingly that use of different types of MARCKS-inhibitory compounds exhibit an inhibitory effect on cancer cell migration in vitro and inhibit metastasis in vivo. In one embodiment, MARCKS-inhibitory compounds exhibit an inhibitory effect on migration of aggressive cancer cell lines. In one embodiment, the MARCKS-inhibitor compounds provided herein inhibit metastasis of cancer cells in a tumor in a mammal. In a further embodiment, the tumor is a solid tumor. In another embodiment, the tumor is a non-solid tumor. In one embodiment, the MARCKS-inhibitor compounds provided herein inhibit metastasis of cancer cells associated with a lymphoma or leukemia.

In one embodiment, MARCKS-inhibitory compounds comprise MARCKS-inhibitory polynucleotides or MARCKS-inhibitory nucleic acid molecules. In a further embodiment, the MARCKS-inhibitory compounds are antisense RNA, siRNA, shRNA, or microRNA polynucleotides that inhibit MARCKS expression and/or function. In one embodiment, the MARCKS-inhibitory compounds are mimics of proteins or polynucleotides that regulate MARCKS expression, such as mimics of miR21.

In one embodiment, the MARKS-inhibitory compounds are MARCKS-related or MANS-related peptides. In another embodiment, the MARCKS-related peptides correspond to the N-terminal myristoylated domain of MARCKS. Thus, in one embodiment, the MARCKS-related peptides are MANS-related peptides. In one embodiment, MANS-related peptides and certain chemically modified MANS-related peptides block migration of aggressive cancer cell lines. In one embodiment, MANS-related peptides are used to exert an inhibitory effect on metastasis of cancer cells. In one embodiment, MARCKS-inhibitory compounds exhibit blocking effects on metastasis of cancer cells in vivo. In vivo sites of inhibition of metastatic disease include at least lung tissue, heart tissue, spleen tissue, intestine tissue, and diaphragm tissue. In one embodiment, MANS-related peptides are used to treat or prevent cancer cell metastasis, cancer cell proliferation, tumor cell growth, or angiogenesis.

In one aspect, compositions and methods are provided for treating or preventing cancer comprising administration of a MARCKS-inhibitory compound to a cancer cell or to a cell that plays a role in the development, maintenance, proliferation, or metastasis of cancer cells. In one embodiment, a method is provided for inhibiting metastasis of a cancer cell comprising administration to the cancer cell of a metastasis-inhibiting amount of a MARCKS-inhibitory compound. In one embodiment, a method is provided for inhibiting metastasis of a cancer cell comprising administration to the cancer cell of a metastasis-inhibiting amount of a MANS-related peptide. In another embodiment, a method is provided for inhibiting metastasis of a cancer cell in a tumor comprising administration to the cancer cell of a metastasis-inhibiting amount of a peptide having an amino acid sequence selected from the group consisting of SEQ ID NO: 1 to SEQ ID NO: 231 (inclusive), SEQ ID NO: 234, and SEQ ID NO: 235; wherein the N-terminal and/or C-terminal amino acid of the peptide sequence is optionally chemically modified. In another embodiment, a method is provided for treating cancer in a subject in need thereof, the method comprising administering to the subject a therapeutically effective amount of a MANS-related peptide. In another embodiment, a method is provided for treating cancer in a subject in need thereof, the method comprising administering to the subject a therapeutically effective amount of a peptide having an amino acid sequence selected from the group consisting of SEQ ID NO: 1 to SEQ ID NO: 231 (inclusive), SEQ ID NO: 234, and SEQ ID NO: 235; wherein the N-terminal and/or C-terminal amino acid of the peptide sequence is optionally chemically modified.

In one embodiment, the N-terminal amino acid of the peptide is chemically modified by acylation of the N-terminal amino acid of the peptide in the form of an amide selected from the group consisting of:

an amide of a $C_2$ (acetyl) to $C_{24}$ aliphatic carboxylic acid which may be linear, branched, saturated, or unsaturated, an amide of trifluoroacetic acid, an amide of benzoic acid, and an amide of a $C_1$ to $C_{24}$ aliphatic alkyl sulfonic acid; or the N-terminal amine group of the N-terminal amino acid of the peptide can be alkylated with a group selected from the group consisting of:

a $C_1$ to $C_{24}$ aliphatic alkyl group, a linear 2-($C_1$ to $C_{24}$ aliphatic alkyl)oxyethyl group, an omega-methoxy-poly(ethyleneoxy)$_n$-ethyl group, where n is from 0 to 10.

In a further embodiment, the N-terminal amide is selected from the group consisting of acetyl and myristoyl.

In another embodiment, the C-terminal amino acid of the peptide is chemically modified by amide formation at the C-terminal carboxylic acid group of the C-terminal amino acid of the peptide in the form of an amide selected from the group consisting of:

an amide of ammonia, an amide of a $C_1$ to $C_{24}$ aliphatic alkyl amine, an amide of a hydroxyl-substituted $C_2$ to $C_{24}$ aliphatic alkyl amine, an amide of a linear 2-(C1 to C24 aliphatic alkyl)oxyethylamine group, and an amide of an omega-methoxy-poly(ethyleneoxy)$_n$-ethylamine group, where n is from 0 to 10.

In one embodiment, a method for inhibiting metastasis of a cancer cell, or for treating cancer, comprising administering a MANS-related peptide to the cancer cell or subject, respectively, is provided. In one embodiment, the peptide is selected from the group consisting of N-myristoyl-GAQF-SKTAAKGEAAAERPGEAAVA (SEQ ID NO: 1); N-myristoyl-GAQFSKTAAKGEAAAERPGEAAV (SEQ ID No: 2); N-myristoyl-GAQFSKTAAKGEAAAERPGEAA (SEQ ID No: 4); N-myristoyl-GAQFSKTAAKGEAAAERPGEA (SEQ ID No: 7); N-myristoyl-GAQFSKTAAKGEAAAERPGE (SEQ ID No: 11); N-myristoyl-GAQFSKTAAKGEAAAERPG (SEQ ID No: 16); N-myristoyl-GAQFSKTAAKGEAAAERP (SEQ ID No: 22); N-myristoyl-GAQFSKTAAKGEAAAER (SEQ ID No: 29); N-myristoyl-GAQFSKTAAKGEAAAE (SEQ ID No: 37); N-myristoyl-GAQFSKTAAKGEAAA (SEQ ID No: 46); N-myristoyl-GAQFSKTAAKGEAA (SEQ ID No: 56); N-myristoyl-GAQFSKTAAKGEA (SEQ ID No: 67); N-myristoyl-GAQFSKTAAKGE (SEQ ID No: 79); N-myristoyl-GAQFSKTAAKG (SEQ ID No: 92); N-myristoyl-GAQFSKTAAK (SEQ ID No: 106); N-myristoyl-GAQFSKTAA (SEQ ID No: 121); N-myristoyl-GAQFSKTA (SEQ ID No: 137); N-myristoyl-GAQFSKT (SEQ ID No: 154); N-myristoyl-GAQFSK (SEQ ID No: 172), N-myristoyl-GAQFS (SEQ ID No: 191), N-myristoyl-GAQF (SEQ ID No: 211), N-acetyl-RGAQFSKTAAK (SEQ ID No: 234), N-acetyl-RGAQFSKTAAK-NH2 (SEQ ID No: 234), N-acetyl-RAKGE (SEQ ID NO: 235), and a combination thereof.

In one embodiment, the peptide is selected from the group consisting of N-acetyl-GAQFSKTAAK (SEQ ID No: 106; BIO-11006); N-myristoyl-AKGE (SEQ ID No: 219; BIO-91200); N-myristoyl-GAQFSKTAAK-NH2 (SEQ ID No: 106; BIO-11002); N-myristoyl-GAQFSKTAAK (SEQ ID No: 106; BIO-11000); N-acetyl-GAQFSKTAA (SEQ ID No: 121; BIO-10901); N-myristoyl-GAQFSKTAAK (SEQ ID No: 121; BIO-10900); and N-acetyl-GAQFSKTAAK-NH2 (SEQ ID No: 106). In one embodiment, certain amino acids are present in d-configuration. For example, in one embodiment, the peptide is N-acetyl-GAQFS(d)KTAA(d)K (SEQ ID NO: 106; BIO-11037), in which the lysine (K) at positions 6 and 10 of the peptide are of d-configuration.

In some embodiments, MANS-related peptides exhibit properties that make them suitable for use in therapeutic applications, for example, in the treatment of cancers. For example, in one embodiment, certain MANS-related peptides disclosed herein exhibit enhanced solubility relative to MANS peptide or peptides other than MANS-related peptides. In another embodiment, certain MANS-related peptides provided herein exhibit longer half-lives in plasma than the MANS peptide or peptides other than MANS-related peptides.

In one embodiment, the MARCKS-related peptide exhibits reduced cancer cell migration. For example, in one embodiment, pretreatment of cancer cells with a MANS-related peptide (e.g., BIO-11006, BIO11002, BIO10901, BIO10900, BIO11000, or BIO-91200) may reduce migration of the cancer cells when cells are pretreated with from about 10 μm peptide to about 200 μm peptide; or pretreated with from about 20 μm to about 200 μm; or pretreated with from about 25 μm peptide to about 75 μm peptide. In one embodiment, the MARCKS-related peptide exhibits reduced cancer cell migration when administered at concentrations of about 1 μM to about 500 μM, about 5 μM to about 250 μM, or about 10 μM to about 200 μM. In one embodiment, the MARCKS-related peptide exhibits reduced cancer cell migration when administered at concentrations of about 1 μM, about 5 μM, about 10 μM, about 25 μM, about 50 μM, about 100 μM, about 150 μM, about 200 μM, or about 500 μM. In one embodiment, cancer cells are treated with the peptide in vitro to determine the effects of the peptide. In one embodiment, the cancer cells are derived from a patient. In a further embodiment, the cancer cells are treated with the peptide in vitro to determine if the patient is likely to respond to treatment with the peptide.

In one embodiment, the MARCKS-related peptide exhibits reduced cancer cell metastasis when administered to a patient at concentrations of about 0.01 mg/kg/day to about 10 mg/kg/day. In a further embodiment, the MARCKS-related peptide exhibits reduced cancer cell metastasis when administered to a patient at concentrations of about 0.1 mg/kg/day to about 5.0 mg/kg/day. In a yet further embodiment, the MARCKS-related peptide exhibits reduced cancer cell metastasis when administered to a patient at concentrations of about 0.5 mg/kg/day to about 2.5 mg/kg/day. For example, the MARCKS-related peptide exhibits reduced cancer cell migration when administered to a patient at concentrations of about 0.01, about 0.05, about 0.1, about 0.5, about 0.75, about 1.0, about 1.25, about 1.5, about 1.75, about 2.0, about 2.25, about 2.5, about 2.75, about 3.0, about 3.5, about 4.0, about 5.0, about 6.0, about 7.0, about 8.0, about 9.0, about 10.0, or more mg/kg/day.

In one embodiment, the peptide is administered by inhalation of a liquid solution or suspension, or by inhalation of a dry powder formulation of the peptide. In another embodiment, the peptide is administered by injection of a liquid formulation or suspension of the peptide. In a further embodiment, the injection is into a primary tumor region, wherein the region contains the cancer cell. In a further embodiment, the cancer cell resides in a tumor in a mammal. In one embodiment, the tumor is a solid tumor. In another embodiment, the tumor is a non-solid tumor. In one embodiment, the MARCKS-inhibitor compounds provided herein inhibit metastasis of cancer cells associated with a lymphoma or leukemia. In another embodiment, the liquid formulation is isotonic. In another embodiment, the liquid formulation is buffered.

In one embodiment, the metastasis-inhibiting amount of the peptide is in the range from about 0.1 to about 100 micromoles per milliliter. In a further embodiment, the metastasis-inhibiting amount of the peptide is in the range from about 1 to about 10 micromoles per milliliter. In another embodiment, the peptide is in a formulation comprising an additional drug useful in the treatment of cancer, or is formulated for administration with an additional drug.

In one aspect, a method for treating or preventing cancer or inhibiting metastasis of a cancer cell in a mammal is provided, wherein the method comprises administering to said mammal a MARCKS-inhibitory compound. In one embodiment, the MARCKS-inhibitory compound is a polynucleotide or nucleic acid molecule that reduces expression or activity of MARCKS. In a further embodiment, the MARCKS-inhibitory polynucleotide is an antisense RNA, siRNA, shRNA, or miRNA. In one embodiment, the MARCKS-inhibitory polynucleotide is administered in an amount from about 10 nM to 10 μM, or from about 20 nM to about 500 nM, or from about 30 nM to about 300 nM, or from about 40 nM to about 200 nM, or from about 50 nM to about 100 nM. In one embodiment, the MARCKS-inhibitory polynucleotide is a mimic of an miRNA that regulates MARCKS expression. For example, in one embodiment, the MARCKS-inhibitory polynucleotide is a mimic of miR21. In one embodiment, the polynucleotides and nucleic acid molecules are administered together with a delivery agent such as a peptide, protein, lipid, sterol, polymer, transfection reagent, or any polynucleotide or nucleic acid delivery agent known in the art.

In one aspect, a method for treating or preventing cancer or inhibiting metastasis of a cancer cell in a mammal is provided, wherein the method comprises administering to said mammal a MANS-related peptide, wherein said peptide exhibits a migration index of at least about 1.5, at least about 1.6, at least about 1.7, at least about 1.8, at least about 1.9, at least about 2.0, at least about 2.1, at least about 2.2, at least about 2.3, at least about 2.4, at least about 2.5, at least about 2.6, at least about 2.7, at least about 2.8 at least about 2.9, at least about 3.0, or more, following pretreatment of non-small-cell lung carcinoma (NSCLC) cells. In a further embodiment, the MANS-related peptide is present at a concentration of about 5, 10, 15, 20, 25, 30, 35, 40, 45, 50, 60, 70, 80, 90, 100, 125, 150, 175, or 200 μmolar of said peptide. In another embodiment, the migration period is 3, 4, 5, 6, 7, 8, 12, 15, 20, 21, 22, 23, or 24 hours. In one embodiment, the MANS-related peptide exhibits a migration index of at least about 1.5 following pretreatment of NSCLC cells with a concentration of 50 μmolar of said peptide and a migration period of about 12 hours. In another embodiment, the MANS-related peptide exhibits a migration index of at least about 2.0 following pretreatment of NSCLC cells with a concentration of at least about 100 μmolar of said peptide and a migration period of about 12 hours.

In one aspect, a method for treating or preventing cancer including cancer metastasis in a subject in need thereof is provided, the method comprising administering a MANS-related peptide to the subject at a dose of about 0.01 mg/kg/day to about 10 mg/kg/day. In a further embodiment, the MANS-related peptide is administered at concentrations of about 0.1 mg/kg/day to about 5.0 mg/kg/day. In a yet further embodiment, the MANS-related peptide is administered at concentrations of about 0.5 mg/kg/day to about 2.5 mg/kg/day. For example, the MANS-related peptide is administered at a dose of about 0.01, about 0.05, about 0.1, about 0.5, about 0.75, about 1.0, about 1.25, about 1.5, about 1.75, about 2.0, about 2.25, about 2.5, about 2.75, about 3.0, about 3.5, about 4.0, about 5.0, about 6.0, about 7.0, about 8.0, about 9.0, about 10.0, or more mg/kg/day for the treatment or prevention of cancer.

BRIEF DESCRIPTION OF THE DRAWINGS

FIG. 1 displays a cell count field of a negative control after a migration time of 12 hours.

FIG. 2A displays a cell count field obtained after pretreatment with 50μμ molar of MANS peptide followed by a migration time of 12 hours.

FIG. 2B displays a cell count field obtained after pretreatment with 100 μmolar of MANS peptide followed by a migration time of 12 hours.

FIG. 7A graphically displays migrated cell numbers obtained 12 hours after pretreatment at 50 μmolar with MANS peptide, BIO11002, BIO10901, BIO91200, or RNS peptide, or no peptide (control).

FIG. 7B graphically displays migrated cell numbers obtained 12 hours after pretreatment at 100 μmolar with MANS peptide, BIO11002, BIO10901, BIO91200, or RNS peptide, or no peptide (control).

FIG. 8A graphically displays the migration index of aggressive human NSCLC cell line cells, wherein a higher value of the migration index signifies less migration after pretreatment with peptides of the invention at 50 μmolar followed by 12 hours of treatment according to the protocol.

FIG. 8B graphically displays the migration index of aggressive human NSCLC cell line cells, wherein a higher value of the migration index signifies less migration after pretreatment with peptides of the invention at 100 μmolar followed by 12 hours of treatment according to the protocol.

DETAILED DESCRIPTION OF THE INVENTION

Figures 3A, 3B:
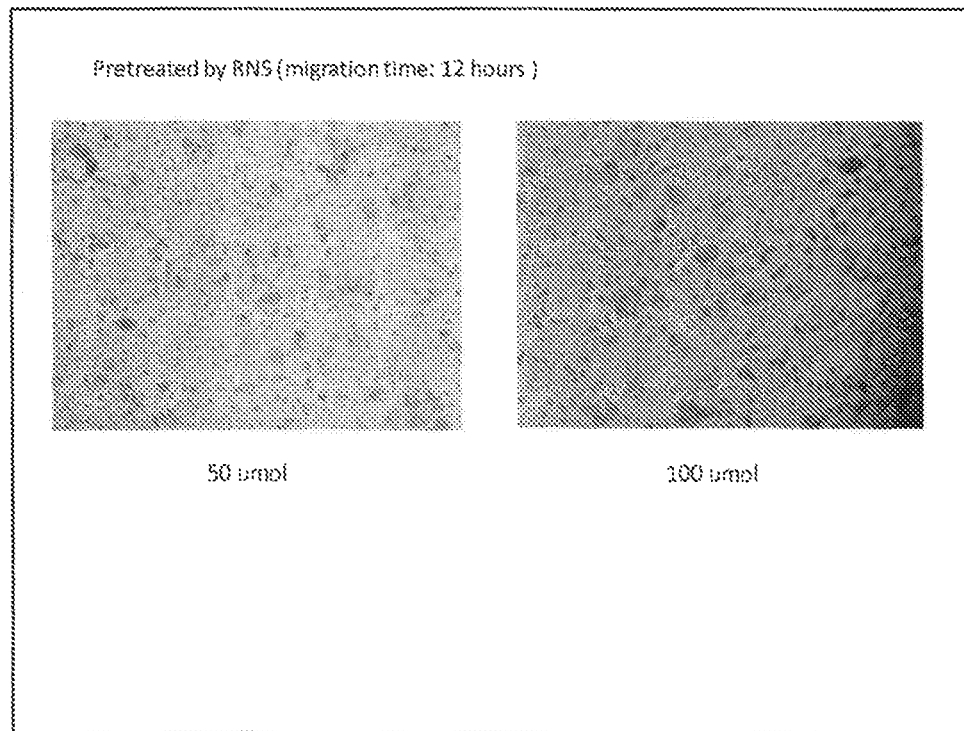
FIG. 3A displays a cell count field obtained after pretreatment with 50 μmolar of RNS peptide followed by a migration time of 12 hours.
FIG. 3B displays a cell count field obtained after pretreatment with 100 μmolar of RNS peptide followed by a migration time of 12 hours.

Myristoylated alanine-rich protein kinase C substrate (MARCKS) protein has been implicated previously in multiple cell processes. For example, it has been shown that MARCKS protein is involved integrally in cellular secretion, degranulation, migration and gene expression. These studies were based on the ability of a peptide identical to the myristoylated N-terminal sequence of MARCKS protein (i.e., MANS peptide) to affect processes in disparate cell types when the cells were pre-treated with the MANS peptide prior to stimulation. In all of these instances, a missense control peptide (consisting of a random amino acid sequence of the amino acids of the MANS peptide, and which is referred to herein as the RNS peptide) was without effect relative to activity exhibited by MANS peptide.

In one embodiment, the compositions comprise MARCKS-inhibitory compounds such as any type of inhibitory compound known in the art including peptides, polypeptides, antibodies or fragments thereof, and polynucleotides or nucleic acid molecules, such as antisense polynucleotides, aptamers, small interfering RNA (siRNA), micro RNA (miRNA), and short-hairpin RNA (shRNA). In one embodiment, the compositions comprise one or more myristoylated alanine-rich C-kinase substrate (MARCKS)-related peptides. In another embodiment, the MARCKS-related peptides correspond to the MH2 domain of MARCKS. In another embodiment, the compositions comprise MARCKS-inhibitory peptides, including peptides corresponding to the N-terminal sequence.

In one embodiment, the MARCKS-inhibitory compound provided herein is an antibody. As used herein, the term "antibody" refers to a binding protein having at least one antigen-binding domain and includes monoclonal antibodies, polyclonal antibodies, and antibody fragments and/or variants, including recombinant polypeptides, fusion proteins, and immunoconjugates. Examples of antibody fragments of the invention include, but are not limited to, the Fab fragment, the Fc fragment, the Fv fragment, the dAb fragment, isolated CDR regions, F(ab')$_2$, bivalent fragments comprising two linked Fab fragments, and single chain Fv molecules (scFv). The skilled artisan will recognize that antibodies or fragments provided herein may be generated from any species including, but not limited to, mouse, rat, rabbit, primate, llama and human. The skilled artisan will further recognize that the antibodies or fragments provided herein may be chimeric, humanized, or fully human.

In one aspect, compositions and methods for treating or preventing cancer are provided. Methods for treating or preventing cancer disclosed herein include treating or preventing all aspects of cancer including, but not limited to, metastasis, tumor growth, cancer cell proliferation, and angiogenesis. In one embodiment, compositions and methods are provided for treating or preventing cancer comprising administration of a MARCKS-inhibitory compound to a cancer cell or to a cell that plays a role in the development, maintence, proliferation, or metastasis of cancer cells, such as, for example, an endothelial cell.

In one aspect, compositions and methods for inhibiting the metastasis of cancer cells are provided, wherein the method comprises administering MARCKS-inhibitory compounds. In one embodiment, the MARCKS-inhibitory compounds are MARCKS-inhibitory peptides, antibodies or fragments thereof that bind to MARCKS or MARCKS peptides, or polynucleotides or nucleic acid molecules including antisense polynucleotides, aptamers, siRNA, miRNA, and shRNA that inhibit the functions of the MARCKS protein. In a further embodiment, the peptides are MANS-related peptides, wherein the peptides inhibit the metastasis of cancer cells. In one embodiment, MARCKS-inhibitory peptides that inhibit the metastasis of cancer cells are provided. In another aspect, methods of treating cancers using the compositions disclosed herein are provided. In one embodiment, the methods provided comprise contacting a cancer cell with a MARCKS-inhibitory peptide. In a further embodiment, the cancer cell is present in a tumor. In one embodiment, the MARCKS-inhibitory peptide is MANS-related peptide. As used herein, the term "MANS-related peptide" refers to MANS peptide or a peptide substantially identical to MANS; or a fragment of MANS peptide that contains at least four contiguous amino acids found in MANS peptide, or is substantially identical to a peptide containing at least 4 contiguous amino acids found in MANS peptide. Thus, MANS-related peptides are from 4 to 24 amino acids in length. As used herein, the term "substantially identical" means, with respect to comparison of the amino acid sequences of two peptides or comparison of the amino acid sequences of two peptide segments (e.g., segments of a reference peptide amino acid sequence), that the amino acid sequence of the peptides or segments of peptides have at least about 75% sequence identity, at least about 80% sequence identity, at least about 90% sequence identity, or at least about 95% sequence identity. Preferably, the amino acid sequence of the peptides have at least about 80% sequence identity to MANS peptide or the MANS peptide fragment. In one embodiment, the MANS-related peptide may comprise a peptide from 4 to 24 amino acids in length that is identical to or substantially identical to MANS peptide and may further comprise one or more additional amino acids. For example, in one embodiment, the MANS-related peptide comprises from 4 to 24 contiguous amino acids identical to or substantially identical to MANS peptide and further comprises at least one N-terminal amino acid that is not present in MANS peptide such as, for example, arginine.

In one embodiment, the MARCKS-inhibitory peptide is chemically modified. In one embodiment, the MARCKS-inhibitory peptide is a MANS-related peptide that is acylated at the N-terminal position. In a further embodiment, the MANS-related peptide is acylated with an acetyl group at the N-terminal position. In another embodiment, the MANS-related peptide is myristoylated at the N-terminal position. In another embodiment, the MANS-related peptide is chemically modified at the C-terminal position. In a further embodiment, the MANS-related peptide is chemically modified at the C-terminal position by formation of an amide with an amine (e.g., ammonia). In another embodiment, the MANS-related peptide is chemically modified at both the N-terminal and C-terminal position. Table 1 lists peptides relevant to the current invention which are myristoylated at their N-terminal position but unsubstituted at their C-terminal position. Certain control peptides (RNS peptides) are listed in Tables 1 and 2, and are myristoylated. However, the RNS peptides are not considered to reside within the scope of the current invention.

TABLE 1

MANS-related peptides of the invention which are N-terminal myristoylated and which can be further chemically modified at the C-terminal position as described herein

| Peptide No. | N-myristoyl Amino Acid Sequences | SEQ ID No: | |
| --- | --- | --- | --- |
| peptide 1 | GAQFSKTAAKGEAAAERPGEAAVA | SEQ ID NO: 1 | MANS |
| peptide 2 | GAQFSKTAAKGEAAAERPGEAAV | SEQ ID NO: 2 | |
| peptide 4 | GAQFSKTAAKGEAAAERPGEAA | SEQ ID NO: 4 | |
| peptide 7 | GAQFSKTAAKGEAAAERPGEA | SEQ ID NO: 7 | |
| peptide 11 | GAQFSKTAAKGEAAAERPGE | SEQ ID NO: 11 | |
| peptide 16 | GAQFSKTAAKGEAAAERPG | SEQ ID NO: 16 | |

TABLE 1-continued

MANS-related peptides of the invention which are N-terminal myristoylated and which can be further chemically modified at the C-terminal position as described herein

| Peptide No. | N-myristoyl Amino Acid Sequences | SEQ ID No: | |
|---|---|---|---|
| peptide 22 | GAQFSKTAAKGEAAAERP | SEQ ID NO: 22 | |
| peptide 29 | GAQFSKTAAKGEAAAER | SEQ ID NO: 29 | |
| peptide 37 | GAQFSKTAAKGEAAAE | SEQ ID NO: 37 | |
| peptide 46 | GAQFSKTAAKGEAAA | SEQ ID NO: 46 | |
| peptide 56 | GAQFSKTAAKGEAA | SEQ ID NO: 56 | |
| peptide 67 | GAQFSKTAAKGEA | SEQ ID NO: 67 | |
| peptide 79 | GAQFSKTAAKGE | SEQ ID NO: 79 | |
| peptide 92 | GAQFSKTAAKG | SEQ ID NO: 92 | |
| peptide 106 | GAQFSKTAAK | SEQ ID NO: 106 | |
| peptide 121 | GAQFSKTAA | SEQ ID NO: 121 | |
| peptide 137 | GAQFSKTA | SEQ ID NO: 137 | |
| peptide 154 | GAQFSKT | SEQ ID NO: 154 | |
| peptide 172 | GAQFSK | SEQ ID NO: 172 | |
| peptide 191 | GAQFS | SEQ ID NO: 191 | |
| peptide 211 | GAQF | SEQ ID NO: 211 | |
| Peptide 232 | GTAPAAEGAGAEVKRASAEAKQAF | SEQ ID NO: 232 | RNS |

Table 2 lists MANS-related peptide fragments of the invention, which can be substituted or chemically modified at the N-terminal and/or C-terminal position. In one embodiment, these active fragments of MANS peptide may be myristoylated at the N-terminal position as are those in Table 1. In another embodiment, chemical modification at the C-terminal position comprises amidation, for example, formation of an amide with an amine, such as, for example, ammonia. Peptide 234 (SEQ ID NO: 234) is an N-terminal arginine-substituted peptide homolog of peptide 106 (SEQ ID NO: 106; RGAQFSKTAAK), which may be chemically modified at the N-terminus (e.g., N-terminal acetyl analog, Ac-RGAQFSKTAAK), and which also may be chemically modified at its N-terminus and its C-terminus (e.g., N-terminal acetyl-, —C-terminal amide with ammonia analog, Ac-RGAQFSKTAAK-NH2). Peptide 235 (SEQ ID NO: 235) is an N-terminal arginine-substituted peptide homolog of peptide 219, (SEQ ID NO: 219; RAKGE) which may be chemically modified at the N-terminus (e.g., N-terminal acetyl analog, Ac-RAKGE), and which also may be chemically modified at its N-terminus and its C-terminus (e.g., N-terminal acetyl-, —C-terminal amide with ammonia analog, Ac-RAKGE-NH2). Preferred N-terminal modifications or substitutions include myristoyl and acetyl groups as well as N-terminal arginine groups, N-terminal acetyl-arginine groups, and N-terminal myristoyl-arginine groups. Preferred C-terminal modification includes the amide group from ammonia.

TABLE 2

MARCKS-related peptide sequences which may be chemically modified at the N-terminal and/or C-terminal position as described herein.

| Peptide No. | MANS peptide and active MANS-related peptide fragments Amino Acid Sequence | SEQ ID No: | |
|---|---|---|---|
| peptide 1 | GAQFSKTAAKGEAAAERPGEAAVA | SEQ ID NO: 1 | MANS |
| peptide 2 | GAQFSKTAAKGEAAAERPGEAAV | SEQ ID NO: 2 | |
| peptide 3 | AQFSKTAAKGEAAAERPGEAAVA | SEQ ID NO: 3 | |
| peptide 4 | GAQFSKTAAKGEAAAERPGEAA | SEQ ID NO: 4 | |
| peptide 5 | AQFSKTAAKGEAAAERPGEAAV | SEQ ID NO: 5 | |
| peptide 6 | QFSKTAAKGEAAAERPGEAAVA | SEQ ID NO: 6 | |

TABLE 2-continued

MARCKS-related peptide sequences which may be chemically modified at the N-terminal and/or C-terminal position as described herein.

| Peptide No. | MANS peptide and active MANS-related peptide fragments Amino Acid Sequence | SEQ ID No: |
|---|---|---|
| peptide 7 | GAQFSKTAAKGEAAAERPGEA | SEQ ID NO: 7 |
| peptide 8 | AQFSKTAAKGEAAAERPGEAA | SEQ ID NO: 8 |
| peptide 9 | QFSKTAAKGEAAAERPGEAAV | SEQ ID NO: 9 |
| peptide 10 | FSKTAAKGEAAAERPGEAAVA | SEQ ID NO: 10 |
| peptide 11 | GAQFSKTAAKGEAAAERPGE | SEQ ID NO: 11 |
| peptide 12 | AQFSKTAAKGEAAAERPGEA | SEQ ID NO: 12 |
| peptide 13 | QFSKTAAKGEAAAERPGEAA | SEQ ID NO: 13 |
| peptide 14 | FSKTAAKGEAAAERPGEAAV | SEQ ID NO: 14 |
| peptide 15 | SKTAAKGEAAAERPGEAAVA | SEQ ID NO: 15 |
| peptide 16 | GAQFSKTAAKGEAAAERPG | SEQ ID NO: 16 |
| peptide 17 | AQFSKTAAKGEAAAERPGE | SEQ ID NO: 17 |
| peptide 18 | QFSKTAAKGEAAAERPGEA | SEQ ID NO: 18 |
| peptide 19 | FSKTAAKGEAAAERPGEAA | SEQ ID NO: 19 |
| peptide 20 | SKTAAKGEAAAERPGEAAV | SEQ ID NO: 20 |
| peptide 21 | KTAAKGEAAAERPGEAAVA | SEQ ID NO: 21 |
| peptide 22 | GAQFSKTAAKGEAAAERP | SEQ ID NO: 22 |
| peptide 23 | AQFSKTAAKGEAAAERPG | SEQ ID NO: 23 |
| peptide 24 | QFSKTAAKGEAAAERPGE | SEQ ID NO: 24 |
| peptide 25 | FSKTAAKGEAAAERPGEA | SEQ ID NO: 25 |
| peptide 26 | SKTAAKGEAAAERPGEAA | SEQ ID NO: 26 |
| peptide 27 | KTAAKGEAAAERPGEAAV | SEQ ID NO: 27 |
| peptide 28 | TAAKGEAAAERPGEAAVA | SEQ ID NO: 28 |
| peptide 29 | GAQFSKTAAKGEAAAER | SEQ ID NO: 29 |
| peptide 30 | AQFSKTAAKGEAAAERP | SEQ ID NO: 30 |
| peptide 31 | QFSKTAAKGEAAAERPG | SEQ ID NO: 31 |
| peptide 32 | FSKTAAKGEAAAERPGE | SEQ ID NO: 32 |
| peptide 33 | SKTAAKGEAAAERPGEA | SEQ ID NO: 33 |
| peptide 34 | KTAAKGEAAAERPGEAA | SEQ ID NO: 34 |
| peptide 35 | TAAKGEAAAERPGEAAV | SEQ ID NO: 35 |
| peptide 36 | AAKGEAAAERPGEAAVA | SEQ ID NO: 36 |
| peptide 37 | GAQFSKTAAKGEAAAE | SEQ ID NO: 37 |
| peptide 38 | AQFSKTAAKGEAAAER | SEQ ID NO: 38 |
| peptide 39 | QFSKTAAKGEAAAERP | SEQ ID NO: 39 |
| peptide 40 | FSKTAAKGEAAAERPG | SEQ ID NO: 40 |
| peptide 41 | SKTAAKGEAAAERPGE | SEQ ID NO: 41 |
| peptide 42 | KTAAKGEAAAERPGEA | SEQ ID NO: 42 |
| peptide 43 | TAAKGEAAAERPGEAA | SEQ ID NO: 43 |

TABLE 2-continued

MARCKS-related peptide sequences which may be chemically modified at the N-terminal and/or C-terminal position as described herein.

| Peptide No. | MANS peptide and active MANS-related peptide fragments Amino Acid Sequence | SEQ ID No: |
|---|---|---|
| peptide 44 | AAKGEAAAERPGEAAV | SEQ ID NO: 44 |
| peptide 45 | AKGEAAAERPGEAAVA | SEQ ID NO: 45 |
| peptide 46 | GAQFSKTAAKGEAAA | SEQ ID NO: 46 |
| peptide 47 | AQFSKTAAKGEAAAE | SEQ ID NO: 47 |
| peptide 48 | QFSKTAAKGEAAAER | SEQ ID NO: 48 |
| peptide 49 | FSKTAAKGEAAAERP | SEQ ID NO: 49 |
| peptide 50 | SKTAAKGEAAAERPG | SEQ ID NO: 50 |
| peptide 51 | KTAAKGEAAAERPGE | SEQ ID NO: 51 |
| peptide 52 | TAAKGEAAAERPGEA | SEQ ID NO: 52 |
| peptide 53 | AAKGEAAAERPGEAA | SEQ ID NO: 53 |
| peptide 54 | AKGEAAAERPGEAAV | SEQ ID NO: 54 |
| peptide 55 | KGEAAAERPGEAAVA | SEQ ID NO: 55 |
| peptide 56 | GAQFSKTAAKGEAA | SEQ ID NO: 56 |
| peptide 57 | AQFSKTAAKGEAAA | SEQ ID NO: 57 |
| peptide 58 | QFSKTAAKGEAAAE | SEQ ID NO: 58 |
| peptide 59 | FSKTAAKGEAAAER | SEQ ID NO: 59 |
| peptide 60 | SKTAAKGEAAAERP | SEQ ID NO: 60 |
| peptide 61 | KTAAKGEAAAERPG | SEQ ID NO: 61 |
| peptide 62 | TAAKGEAAAERPGE | SEQ ID NO: 62 |
| peptide 63 | AAKGEAAAERPGEA | SEQ ID NO: 63 |
| peptide 64 | AKGEAAAERPGEAA | SEQ ID NO: 64 |
| peptide 65 | KGEAAAERPGEAV | SEQ ID NO: 65 |
| peptide 66 | GEAAAERPGEAAVA | SEQ ID NO: 66 |
| peptide 67 | GAQFSKTAAKGEA | SEQ ID NO: 67 |
| peptide 68 | AQFSKTAAKGEAA | SEQ ID NO: 68 |
| peptide 69 | QFSKTAAKGEAAA | SEQ ID NO: 69 |
| peptide 70 | FSKTAAKGEAAAE | SEQ ID NO: 70 |
| peptide 71 | SKTAAKGEAAAER | SEQ ID NO: 71 |
| peptide 72 | KTAAKGEAAAERP | SEQ ID NO: 72 |
| peptide 73 | TAAKGEAAAERPG | SEQ ID NO: 73 |
| peptide 74 | AAKGEAAAERPGE | SEQ ID NO: 74 |
| peptide 75 | AKGEAAAERPGEA | SEQ ID NO: 75 |
| peptide 76 | KGEAAAERPGEAA | SEQ ID NO: 76 |
| peptide 77 | GEAAAERPGEAAV | SEQ ID NO: 77 |
| peptide 78 | EAAAERPGEAAVA | SEQ ID NO: 78 |
| peptide 79 | GAQFSKTAAKGE | SEQ ID NO: 79 |

TABLE 2-continued

MARCKS-related peptide sequences which may be chemically modified at the N-terminal and/or C-terminal position as described herein.

| Peptide No. | MANS peptide and active MANS-related peptide fragments Amino Acid Sequence | SEQ ID No: |
|---|---|---|
| peptide 80 | AQFSKTAAKGEA | SEQ ID NO: 80 |
| peptide 81 | QFSKTAAKGEAA | SEQ ID NO: 81 |
| peptide 82 | FSKTAAKGEAAA | SEQ ID NO: 82 |
| peptide 83 | SKTAAKGEAAAE | SEQ ID NO: 83 |
| peptide 84 | KTAAKGEAAAER | SEQ ID NO: 84 |
| peptide 85 | TAAKGEAAAERP | SEQ ID NO: 85 |
| peptide 86 | AAKGEAAAERPG | SEQ ID NO: 86 |
| peptide 87 | AKGEAAAERPGE | SEQ ID NO: 87 |
| peptide 88 | KGEAAAERPGEA | SEQ ID NO: 88 |
| peptide 89 | GEAAAERPGEAA | SEQ ID NO: 89 |
| peptide 90 | EAAAERPGEAAV | SEQ ID NO: 90 |
| peptide 91 | AAAERPGEAAVA | SEQ ID NO: 91 |
| peptide 92 | GAQFSKTAAKG | SEQ ID NO: 92 |
| peptide 93 | AQFSKTAAKGE | SEQ ID NO: 93 |
| peptide 94 | QFSKTAAKGEA | SEQ ID NO: 94 |
| peptide 95 | FSKTAAKGEAA | SEQ ID NO: 95 |
| peptide 96 | SKTAAKGEAAA | SEQ ID NO: 96 |
| peptide 97 | KTAAKGEAAAE | SEQ ID NO: 97 |
| peptide 98 | TAAKGEAAAER | SEQ ID NO: 98 |
| peptide 99 | AAKGEAAAERP | SEQ ID NO: 99 |
| peptide 100 | AKGEAAAERPG | SEQ ID NO: 100 |
| peptide 101 | KGEAAAERPGE | SEQ ID NO: 101 |
| peptide 102 | GEAAAERPGEA | SEQ ID NO: 102 |
| peptide 103 | EAAAERPGEAA | SEQ ID NO: 103 |
| peptide 104 | AAAERPGEAAV | SEQ ID NO: 104 |
| peptide 105 | AAERPGEAAVA | SEQ ID NO: 105 |
| peptide 106 | GAQFSKTAAK | SEQ ID NO: 106 |
| peptide 107 | AQFSKTAAKG | SEQ ID NO: 107 |
| peptide 108 | QFSKTAAKGE | SEQ ID NO: 108 |
| peptide 109 | FSKTAAKGEA | SEQ ID NO: 109 |
| peptide 110 | SKTAAKGEAA | SEQ ID NO: 110 |
| peptide 111 | KTAAKGEAAA | SEQ ID NO: 111 |
| peptide 112 | TAAKGEAAAE | SEQ ID NO: 112 |
| peptide 113 | AAKGEAAAER | SEQ ID NO: 113 |
| peptide 114 | AKGEAAAERP | SEQ ID NO: 114 |
| peptide 115 | KGEAAAERPG | SEQ ID NO: 115 |
| peptide 116 | GEAAAERPGE | SEQ ID NO: 116 |

TABLE 2-continued

MARCKS-related peptide sequences which may be chemically modified at the N-terminal and/or C-terminal position as described herein.

| Peptide No. | MANS peptide and active MANS-related peptide fragments Amino Acid Sequence | SEQ ID No: |
|---|---|---|
| peptide 117 | EAAAERPGEA | SEQ ID NO: 117 |
| peptide 118 | AAAERPGEAA | SEQ ID NO: 118 |
| peptide 119 | AAERPGEAAV | SEQ ID NO: 119 |
| peptide 120 | AERPGEAAVA | SEQ ID NO: 120 |
| peptide 121 | GAQFSKTAA | SEQ ID NO: 121 |
| peptide 122 | AQFSKTAAK | SEQ ID NO: 122 |
| peptide 123 | QFSKTAAKG | SEQ ID NO: 123 |
| peptide 124 | FSKTAAKGE | SEQ ID NO: 124 |
| peptide 125 | SKTAAKGEA | SEQ ID NO: 125 |
| peptide 126 | KTAAKGEAA | SEQ ID NO: 126 |
| peptide 127 | TAAKGEAAA | SEQ ID NO: 127 |
| peptide 128 | AAKGEAAAE | SEQ ID NO: 128 |
| peptide 129 | AKGEAAAER | SEQ ID NO: 129 |
| peptide 130 | KGEAAAERP | SEQ ID NO: 130 |
| peptide 131 | GEAAAERPG | SEQ ID NO: 131 |
| peptide 132 | EAAAERPGE | SEQ ID NO: 132 |
| peptide 133 | AAAERPGEA | SEQ ID NO: 133 |
| peptide 134 | AAERPGEAA | SEQ ID NO: 134 |
| peptide 135 | AERPGEAAV | SEQ ID NO: 135 |
| peptide 136 | ERPGEAAVA | SEQ ID NO: 136 |
| peptide 137 | GAQFSKTA | SEQ ID NO: 137 |
| peptide 138 | AQFSKTAA | SEQ ID NO: 138 |
| peptide 139 | QFSKTAAK | SEQ ID NO: 139 |
| peptide 140 | FSKTAAKG | SEQ ID NO: 140 |
| peptide 141 | SKTAAKGE | SEQ ID NO: 141 |
| peptide 142 | KTAAKGEA | SEQ ID NO: 142 |
| peptide 143 | TAAKGEAA | SEQ ID NO: 143 |
| peptide 144 | AAKGEAAA | SEQ ID NO: 144 |
| peptide 145 | AKGEAAAE | SEQ ID NO: 145 |
| peptide 146 | KGEAAAER | SEQ ID NO: 146 |
| peptide 147 | GEAAAERP | SEQ ID NO: 147 |
| peptide 148 | EAAAERPG | SEQ ID NO: 148 |
| peptide 149 | AAAERPGE | SEQ ID NO: 149 |
| peptide 150 | AAERPGEA | SEQ ID NO: 150 |
| peptide 151 | AERPGEAA | SEQ ID NO: 151 |
| peptide 152 | ERPGEAAV | SEQ ID NO: 152 |

TABLE 2-continued

MARCKS-related peptide sequences which may be chemically modified at the N-terminal and/or C-terminal position as described herein.

| Peptide No. | MANS peptide and active MANS-related peptide fragments Amino Acid Sequence | SEQ ID No: |
|---|---|---|
| peptide 153 | RPGEAAVA | SEQ ID NO: 153 |
| peptide 154 | GAQFSKT | SEQ ID NO: 154 |
| peptide 155 | AQFSKTA | SEQ ID NO: 155 |
| peptide 156 | QFSKTAA | SEQ ID NO: 156 |
| peptide 157 | FSKTAAK | SEQ ID NO: 157 |
| peptide 158 | SKTAAKG | SEQ ID NO: 158 |
| peptide 159 | KTAAKGE | SEQ ID NO: 159 |
| peptide 160 | TAAKGEA | SEQ ID NO: 160 |
| peptide 161 | AAKGEAA | SEQ ID NO: 161 |
| peptide 162 | AKGEAAA | SEQ ID NO: 162 |
| peptide 163 | KGEAAAE | SEQ ID NO: 163 |
| peptide 164 | GEAAAER | SEQ ID NO: 164 |
| peptide 165 | EAAAERP | SEQ ID NO: 165 |
| peptide 166 | AAAERPG | SEQ ID NO: 166 |
| peptide 167 | AAERPGE | SEQ ID NO: 167 |
| peptide 168 | AERPGEA | SEQ ID NO: 168 |
| peptide 169 | ERPGEAA | SEQ ID NO: 169 |
| peptide 170 | RPGEAAV | SEQ ID NO: 170 |
| peptide 171 | PGEAAVA | SEQ ID NO: 171 |
| peptide 172 | GAQFSK | SEQ ID NO: 172 |
| peptide 173 | AQFSKT | SEQ ID NO: 173 |
| peptide 174 | QFSKTA | SEQ ID NO: 174 |
| peptide 175 | FSKTAA | SEQ ID NO: 175 |
| peptide 176 | SKTAAK | SEQ ID NO: 176 |
| peptide 177 | KTAAKG | SEQ ID NO: 177 |
| peptide 178 | TAAKGE | SEQ ID NO: 178 |
| peptide 179 | AAKGEA | SEQ ID NO: 179 |
| peptide 180 | AKGEAA | SEQ ID NO: 180 |
| peptide 181 | KGEAAA | SEQ ID NO: 181 |
| peptide 182 | GEAAAE | SEQ ID NO: 182 |
| peptide 183 | EAAAER | SEQ ID NO: 183 |
| peptide 184 | AAAERP | SEQ ID NO: 184 |
| peptide 185 | AAERPG | SEQ ID NO: 185 |
| peptide 186 | AERPGE | SEQ ID NO: 186 |
| peptide 187 | ERPGEA | SEQ ID NO: 187 |
| peptide 188 | RPGEAA | SEQ ID NO: 188 |
| peptide 189 | PGEAAV | SEQ ID NO: 189 |

TABLE 2-continued

MARCKS-related peptide sequences which may be chemically modified at the N-terminal and/or C-terminal position as described herein.

| Peptide No. | MANS peptide and active MANS-related peptide fragments Amino Acid Sequence | SEQ ID No: |
|---|---|---|
| peptide 190 | GEAAVA | SEQ ID NO: 190 |
| peptide 191 | GAQFS | SEQ ID NO: 191 |
| peptide 192 | AQFSK | SEQ ID NO: 192 |
| peptide 193 | QFSKT | SEQ ID NO: 193 |
| peptide 194 | FSKTA | SEQ ID NO: 194 |
| peptide 195 | SKTAA | SEQ ID NO: 195 |
| peptide 196 | KTAAK | SEQ ID NO: 196 |
| peptide 197 | TAAKG | SEQ ID NO: 197 |
| peptide 198 | AAKGE | SEQ ID NO: 198 |
| peptide 199 | AKGEA | SEQ ID NO: 199 |
| peptide 200 | KGEAA | SEQ ID NO: 200 |
| peptide 201 | GEAAA | SEQ ID NO: 201 |
| peptide 202 | EAAAE | SEQ ID NO: 202 |
| peptide 203 | AAAER | SEQ ID NO: 203 |
| peptide 204 | AAERP | SEQ ID NO: 204 |
| peptide 205 | AERPG | SEQ ID NO: 205 |
| peptide 206 | ERPGE | SEQ ID NO: 206 |
| peptide 207 | RPGEA | SEQ ID NO: 207 |
| peptide 208 | PGEAA | SEQ ID NO: 208 |
| peptide 209 | GEAAV | SEQ ID NO: 209 |
| peptide 210 | EAAVA | SEQ ID NO: 210 |
| peptide 211 | GAQF | SEQ ID NO: 211 |
| peptide 212 | AQFS | SEQ ID NO: 212 |
| peptide 213 | QFSK | SEQ ID NO: 213 |
| peptide 214 | FSKT | SEQ ID NO: 214 |
| peptide 215 | SKTA | SEQ ID NO: 215 |
| peptide 216 | KTAA | SEQ ID NO: 216 |
| peptide 217 | TAAK | SEQ ID NO: 217 |
| peptide 218 | AAKG | SEQ ID NO: 218 |
| peptide 219 | AKGE | SEQ ID NO: 219 |
| peptide 220 | KGEA | SEQ ID NO: 220 |
| peptide 221 | GEAA | SEQ ID NO: 221 |
| peptide 222 | EAAA | SEQ ID NO: 222 |
| peptide 223 | AAAE | SEQ ID NO: 223 |
| peptide 224 | AAER | SEQ ID NO: 224 |
| peptide 225 | AERP | SEQ ID NO: 225 |

TABLE 2-continued

MARCKS-related peptide sequences which may be chemically modified at the N-terminal and/or C-terminal position as described herein.

| Peptide No. | MANS peptide and active MANS-related peptide fragments Amino Acid Sequence | SEQ ID No: | |
|---|---|---|---|
| peptide 226 | ERPG | SEQ ID NO: 226 | |
| peptide 227 | RPGE | SEQ ID NO: 227 | |
| peptide 228 | PGEA | SEQ ID NO: 228 | |
| peptide 229 | GEAA | SEQ ID NO: 229 | |
| peptide 230 | EAAV | SEQ ID NO: 230 | |
| peptide 231 | AAVA | SEQ ID NO: 231 | |
| Peptide 232 | GTAPAAEGAGAEVKRASAEAKQAF | SEQ ID NO: 232 | RNS |
| Peptide 233 | GKASQFAKTA | SEQ ID NO: 233 | RNS2 |
| Peptide 234 | RGAQFSKTAAK | SEQ ID NO: 234 | |
| Peptide 235 | RAKGE | SEQ ID NO: 235 | |

The MANS peptide is myristoylated (denoted as MA), and contains the 24 amino acid sequence MA-GAQFSK-TAAKGEAAARPGEAAVA. Without wishing to be bound by theory, the peptide is theorized to interfere with the full length MARCKS protein attaching naturally to the cell membrane and interfering with phosphorylation of MARCKS protein by protein kinase C (PKC).

MANS peptide has been shown to provide a significant reduction in degranulation of goblet cells both in vitro and in vivo. MANS also affects the rate of migration of neutrophils and mesenchymal stem cells. Degranulation of human leukocytes is also inhibited by MANS. In one aspect of this invention, treatment of certain cancer cell lines with MANS-related peptides decreases migration of those cancer cell lines. In one embodiment, MANS-related peptides exhibit inhibition of metastasis of cancer cells. Thus, in one embodiment, the MANS-related peptides provided may be used to treat or prevent metastatic cancer in a subject in need thereof. In some embodiments, MANS-related peptides exhibit properties that make them suitable for use in therapeutic applications, for example, in the treatment of cancers. For example, in one embodiment, MANS-related peptides exhibit enhanced solubility relative to MANS peptide. In another embodiment, some MANS-related peptides exhibit longer half-lives in plasma than the MANS peptide or relative to peptides other than MANS-related peptides. In one embodiment, MANS-related peptides may be useful in the treatment of proliferation of cancer cells. For example, in one embodiment, MANS-related peptides may inhibit proliferation and or migration of cancer cells. In another embodiment, some MANS-related peptides may provide greater inhibition of proliferation and or migration of cancer cells at lower concentrations than the MANS peptide or than other MANS-related peptides.

In one aspect, the MANS-related peptide is selected from the group consisting of:

N-myristoyl-GAQFSKTAAK (SEQ ID No: 106; BIO-11000)

N-acetyl-GAQFSKTAAK; (SEQ ID No: 106; BIO-11006)

N-myristoyl-AKGE; (SEQ ID No: 219; BIO-91200)

N-myristoyl-GAQFSKTAAK-NH2; (SEQ ID No: 106; BIO-11002)

N-acetyl-GAQFSKTAA; (SEQ ID No. 121; BIO-10901)

N-acetyl-GAQFSKTAAK-NH2; (SEQ ID No: 106; BIO-11026)

N-acetyl-GAQFS(d)KTAA(d)K (Lys at positions positions 6 and 10 of the peptide are of d-configuration; (SEQ ID No: 106; BIO-11037)

N-acetyl-RGAQFSKTAAK; (SEQ ID No: 234; BIO-11027)

N-acetyl-RGAQFSKTAAK-NH2; and (SEQ ID No: 234; BIO-11028)

N-acetyl-RAKGE. (SEQ ID NO: 235; BIO-91204)

In one aspect, peptides having 4 to 24 amino acids and which have amino acid sequences that are identical to or are substantially identical to amino acid sequences found in the MANS peptide can be useful in one or more aspects of this invention. These peptides are herein referred to as MANS-related peptides, and exemplary MANS-related peptides are listed in Table 2 as SEQ ID NOs: 1 to 231, 234, and 235. Table 2 also includes the amino acid sequence of the random sequence (RNS) peptide No. 232 (SEQ ID NO: 232), which is used as a control and to demonstrate that amino acid sequence order can be relevant to efficacy in this invention, as well as a second random sequence control peptide 233 (RNS2; SEQ ID NO: 233). Peptides 234 and 235 (SEQ ID NO: 234 and 235) are N-terminal arginine-substituted peptide homologs of peptides 106 and 219, respectively. The arginine can be acylated with, for example, an acetyl group or a myristoyl group.

In one embodiment, peptides which can be useful in the current invention can be selected from the group consisting of synthetic peptides having amino acid sequences listed in Table 2 (excluding random sequence peptides 232 and 233).

In another embodiment, peptides which can be useful in the current invention can be selected from peptides of amino acid sequences as listed in Table 2 (SEQ ID NO: 1 to 231 (inclusive), 234, and 235) and which are optionally N-terminal- and/or C-terminal-chemically modified.

Preferred independent N-terminal chemical modifications of the peptides listed in Table 2 include N-terminal amine group modification by acylation of the N-terminal amino acid of the peptide in the form of an amide selected from the group consisting of:

an amide of a C2 (acetyl) to C24 aliphatic carboxylic acid which may be linear, branched, saturated, or unsaturated, an amide of trifluoroacetic acid, an amide of a benzoic acid, and an amide of a $C_1$ to C24 aliphatic alkyl sulfonic acid; or the N-terminal amine group of the N-terminal amino acid of the peptide can be alkylated with a group selected from the group consisting of:

a $C_1$ (methyl) to $C_{24}$ aliphatic alkyl group, a linear 2-($C_1$ to $C_{24}$ aliphatic alkyl)oxyethyl group, an omega-methoxy-poly(ethyleneoxy)$_n$-ethyl group, where n is from 0 to 10.

Preferred independent C-terminal chemical modifications of the peptides listed in Table 2 include amide formation at the C-terminal carboxylic acid group of the C-terminal amino acid of the peptide in the form of an amide selected from the group consisting of:

an amide of ammonia, an amide of a $C_1$ to $C_{24}$ aliphatic alkyl amine, an amide of a hydroxyl-substituted $C_2$ to $C_{24}$ aliphatic alkyl amine, an amide of a linear 2-(C1 to C24 aliphatic alkyl)oxyethylamine group, and an amide of an omega-methoxy-poly(ethyleneoxy)$_n$-ethylamine group, where n is from 0 to 10.

In addition, the C-terminal carboxylic acid group of the C-terminal amino acid of the peptide is optionally in the form of an ester selected from the group consisting of:

an ester of a $C_1$ to C24 aliphatic alkyl alcohol, an ester of a 2-(omega-methoxy-poly(ethyleneoxy)$_n$)-ethanol group, where n is from 0 to 10, and an ester of a linear PEG-amine, the PEG component of molecular weight from 1,000 to 25,000 Daltons.

In one embodiment, aliphatic portions of groups such as carboxylic acid groups and sulfonic acid groups and alcohol and amino groups can comprise a ring of at least C3 (i.e., at least a cyclopropyl ring).

In one embodiment, the peptide can be N-terminally modified, for example, by an acetyl group or a myristoyl group, as an N-terminal amide, such as Acetyl-GAQFSKTAAK (N-terminal acetyl SEQ ID No: 106) and myristoyl-GAQFSKTAAK (N-terminal myristoyl SEQ ID No: 106), respectively. In another embodiment, the peptide can be C-terminally modified (for example by an amide with ammonia) such as GAQFSKTAAK-NH$_2$ (SEQ ID No: 106 C-terminal amide). In another embodiment, the peptide can be N-terminally modified and C-terminally modified, for example as N-acetyl-peptide-C-amide (with ammonia) such as Acetyl-GAQFSKTAAK-NH$_2$. (N-terminal acetyl SEQ ID No: 106 C-terminal amide) and Myristoyl-GAQFSKTAAK-NH$_2$ (N-terminal myristoyl SEQ ID No: 106 C-terminal amide). These peptides can be used in the methods of this invention and to determine their ability to inhibit metastases of cancer cells.

In one embodiment, a peptide which may find use in this invention can be selected from the group of peptides which contain the amino acid sequence AKGE (SEQ ID No: 219). Such peptides include SEQ ID No: 1 through SEQ ID No: 54, SEQ ID No: 56 through SEQ ID No: 64, SEQ ID No: 67 through SEQ ID No: 75, SEQ ID No: 79 through SEQ ID No: 87, SEQ ID No: 93 through SEQ ID No: 100, SEQ ID No: 108 through SEQ ID No: 114, SEQ ID No: 124 through SEQ ID No: 129, SEQ ID No: 141 through SEQ ID No: 145, SEQ ID No: 159 through SEQ ID No: 162, SEQ ID No: 178 through SEQ ID No: 180, SEQ ID No: 198, SEQ ID No: 199, SEQ ID No: 219, and SEQ ID NO: 235. In one currently preferred embodiment, these peptides are myristoylated or acetylated at the N-terminal amino group.

In one embodiment, this invention discloses a method of attenuating the metastasis of a cancer cell toward an increasing concentration gradient of a chemotactic agent in a fluid or tissue, the method comprising treatment of said cancer cell with a migration-inhibiting amount of a migration-modulating peptide and incubation of said cell with said peptide to form a migration-inhibited cancer cell, wherein the peptide is a MANS-related peptide.

In one aspect, the migration-modulating peptide is selected from the group consisting of MANS-related peptides. In another aspect, the MANS-related peptide comprises the amino acid sequence GAQFSKTAAK (SEQ ID No: 106).

In another aspect, the MANS-related peptide is selected from the group consisting of N-myristoyl-GAQFSKTAAK-GEAAAERPGEAAVA (SEQ ID No: 1) N-myristoyl-GAQFSKTAAKGEAAAERPGEAAV (SEQ ID No: 2); N-myristoyl-GAQFSKTAAKGEAAAERPGEAA (SEQ ID No: 4); N-myristoyl-GAQFSKTAAKGEAAAERPGEA (SEQ ID No: 7); N-myristoyl-GAQFSKTAAKGEAAAERPGE (SEQ ID No: 11); N-myristoyl-GAQFSKTAAK-GEAAAERPG (SEQ ID No: 16); N-myristoyl-GAQFSK-TAAKGEAAAERP (SEQ ID No: 22); N-myristoyl-GAQF-SKTAAKGEAAAER (SEQ ID No: 29); N-myristoyl-GAQFSKTAAKGEAAAE (SEQ ID No: 37); N-myristoyl-GAQFSKTAAKGEAAA (SEQ ID No: 46); N-myristoyl-GAQFSKTAAKGEAA (SEQ ID No: 56); N-myristoyl-GAQFSKTAAKGEA (SEQ ID No: 67); N-myristoyl-GAQFSKTAAKGE (SEQ ID No: 79); N-myristoyl-GAQFSKTAAKG (SEQ ID No: 92); N-myristoyl-GAQFSKTAAK (SEQ ID No: 106); N-myristoyl-GAQFSKTAA (SEQ ID No: 121); N-myristoyl-GAQFSKTA (SEQ ID No: 137); N-myristoyl-GAQFSKT (SEQ ID No: 154); N-myristoyl-GAQFSK (SEQ ID No: 172), N-myristoyl-GAQFS (SEQ ID No: 191), N-myristoyl-GAQF (SEQ ID No: 211), N-acetyl-RGAQFSKTAAK (SEQ ID No: 234), N-acetyl-RGAQFSKTAAK-NH2 (SEQ ID No: 234), N-acetyl-RAKGE (SEQ ID NO: 235), and a combination thereof.

In another aspect, the MANS-related peptide is selected from the group consisting of:

```
                              (SEQ ID No: 1; MANS peptide)
    N-myristoyl-GAQFSKTAAKGEAAAERPGEAAVA;

(SEQ ID No: 106; BIO-11000)
    N-myristoyl-GAQFSKTAAK;
```

```
                    (SEQ ID No: 106; BIO-11006)
N-acetyl-GAQFSKTAAK;

(SEQ ID No: 106; BIO-11026)
N-acetyl-GAQFSKTAAK-NH2;

(SEQ ID No: 219; BIO-91200)
N-myristoyl-AKGE;

(SEQ ID No: 106; BIO-11002)
N-myristoyl-GAQFSKTAAK-NH2;

(SEQ ID No. 121; BIO-10901)
N-acetyl-GAQFSKTAA (SEQ ID No: 234; BIO-11027)
N-acetyl-RGAQFSKTAAK (SEQ ID No: 234; BIO-11028)
N-acetyl-RGAQFSKTAAK-NH2,
and (SEQ ID NO: 235; BIO-91204)
N-acetyl-RAKGE.
```

In one aspect, the metastasis-inhibiting dose of a peptide of this invention can be in the range of about 0.01 mg/kg/day to about 10 mg/kg/day. In a further embodiment, the metastasis-inhibiting dose of a peptide is about 0.1 mg/kg/day to about 5.0 mg/kg/day. In a yet further embodiment, the metastasis-inhibiting dose of a peptide is about 0.5 mg/kg/day to about 2.5 mg/kg/day. For example, the metastasis-inhibiting dose of a peptide of this invention is about 0.01, about 0.05, about 0.1, about 0.5, about 0.75, about 1.0, about 1.25, about 1.5, about 1.75, about 2.0, about 2.25, about 2.5, about 2.75, about 3.0, about 3.5, about 4.0, about 5.0, about 6.0, about 7.0, about 8.0, about 9.0, about 10.0, or more mg/kg/day.

In one embodiment, this invention provides a method for inhibiting metastasis of a cancer cell, wherein the administration is by oral, intravenous, intraperitoneal, intramuscular, inhalation, or suppository routes. In another embodiment, this invention discloses a method for inhibiting metastasis of a cancer cell, wherein the administration is by inhalation of a liquid solution or suspension or dry powder formulation of the MARCKS-inhibitory compound. In one embodiment, a method for treating cancer is provided, wherein a MARCKS-inhibitory compound is administered to a subject in need thereof by inhalation of a liquid solution or suspension or dry powder formulation of the MARCKS-inhibitory compound. For example, in one embodiment, a MANS-related peptide is administered to a subject in need thereof by inhalation of a liquid solution or suspension or dry powder formulation of the MANS-related peptide. In another embodiment, a MANS-related peptide is administered by intravenous, intraperitoneal, or intramuscular injection, or by oral or suppository administration.

In another aspect, this invention discloses a method for inhibiting metastasis of a cancer cell, or treating cancer in a subject in need thereof, wherein the MANS-related peptide is administered is by injection of a liquid formulation of the peptide, and wherein the liquid formulation is isotonic, and wherein the liquid or suspension formulation is buffered, and wherein the injection is systemic into a subject. In another embodiment, the injection is into the region of a tumor. In another embodiment, the injection is into the tumor.

In another aspect, this invention discloses a method for inhibiting metastasis of a cancer cell, wherein the cancer cell resides in a mammal. In one embodiment, a method for treating cancer is provided, wherein a MANS-related peptide is administered to the subject in need thereof, and wherein the subject has a tumor. The peptides of this invention can be formulated using one or more pharmaceutically acceptable excipients or ingredients to provide pharmaceutical compositions useful for administration to cancer cells, such as cancer cells in a primary tumor. Such compositions can be as solutions or suspensions in a liquid, especially in buffered solution, wherein phosphate buffer is useful, when administration by injection or by inhalation is useful. Isotonic solutions or suspensions are preferred embodiments.

It is anticipated that administration of an antibody, polynucleotide, nucleic acid molecule, or peptide composition of this invention in mammals such as canines, felines, and human patients, can be effective if done by injection into a primary tumor region (e.g., directly into a primary tumor, or into a margin of a primary tumor, or into a blood vessel feeding a primary tumor) in the mammal, wherein the injection is done at regular intervals (for example, every 1 to every 72 hours), optionally in combination with or separately with one or more other or additional chemotherapy drugs.

One or more additional therapeutic agents, including chemotherapeutic drugs and cancer specific antibodies, can be administered in addition to the MARCKS-inhibitory antibody, polynucleotide, nucleic acid molecule, or peptide formulation, before, during, or after the peptide administration. Exemplary chemotherapeutic drugs include, but are not limited to, carboplatin, cisplatin, oxaliplatin, cyclophosphamide, dacarbazine, temozolomide, gemcitabine, capecitabine, cladribine, clofarabine, cytarabine, floxuridine, fludarabine, hydroxyurea, methotrexate, pemetrexed, pentostatin, thioguanadine, daunorubicin, doxurubicin, epirubicin, idarubicin, topotecan, irinotecan, etoposide, eniposide, colchicine, vincristine, vinblastine, vinorelbine, paclitaxel, and docetaxel. Exemplary cancer specific agents and antibodies include, but are not limited to, Afatinib, Aldesleukin, Alemtuzumab, Axitinib, Belimumab, Bevacizumab, Bortezomib, Bosutinib, Brentuximab vedotin, Cabozantinib, Canakinumab, Carfilzomib, Cetuximab, Crizotinib, Dabrafenib, Dasatinib, Denosumab, Erlotinib, Everolimus, Gefitinib, Ibritumomab tiuxetan, Ibrutinib, Imatinib, Ipilimumab, Lapatinib, Nilotinib, Obinutuzumab, Ofatumumab, Panitumumab, Pazopanib, Pertuzumab, Ponatinib, Regorafenib, Rituximab, Romidepsin, Ruxolitinib, Sipuleucel-T, Sorafenib, Temsirolimus, Tocilizumab, Tofacitinib, Tositumomab, Trametinib, Trastuzumab, Vandetanib, Vemurafenib, Vismodegib, Vorinostat, and Ziv-aflibercept.

Administration may be, for example, by inhalation as a liquid or dry powder aerosol or spray, such as into the airways of a patient with cancer, which spray may form a coating on a tissue containing a cancer cell, or as a liquid for injection into a fluid or tissue containing or in contact with a cancer cell prior to metastasis. Use of a mild surface active agent such as a phospholipid is contemplated to assist solubilization and transmembrane uptake of the MANS-related peptide. Administration may also be, for example, by a dry powder, preferably a nanoparticulate or a microparticulate powder, applicable by sprinkling onto a tissue containing a cancer cell. Addition of a microparticulate carbohydrate carrier to the preparation of the peptide will facilitate inhalation delivery of nanoparticulate peptide into airways and epithelial tissue areas.

A preferred method of application of the MARCKS-inhibitory antibody, polynucleotide, nucleic acid molecule, or peptide composition comprises injection into tissue in or proximal to a tumor, which tumor contains a cancer cell prior to metastasis.

As used herein, the phrase "effective amount" or "therapeutically effective amount" refers to a nontoxic but sufficient amount of the compositions used in the practice of the invention that is effective to achieve the desired effect, i.e., to inhibit metastasis and/or proliferation of a cancer cell, and/or to inhibit, treat, or prevent cancer in a subject in need thereof. Thus, the activity contemplated by the present methods includes both medical therapeutic and/or prophylactic treatment, as appropriate, including, for example, a reduction and/or alleviation of the signs, symptoms, or causes of a cancer. A therapeutically effective amount of compound of this invention is typically an amount such that when it is administered in a physiologically tolerable excipient composition, it is sufficient to achieve an effective intracellular concentration and local concentration in the tissue.

"Cancer" herein refers to or describes the physiological condition in mammals that is typically characterized by unregulated cell growth. Examples of cancer include but are not limited to carcinoma, lymphoma, blastoma, sarcoma (including liposarcoma, osteogenic sarcoma, angiosarcoma, endotheliosarcoma, lymphangiosarcoma, lymphangioendotheliosarcoma, leiomyosarcoma, rhabdomyosarcoma, fibrosarcoma, myxosarcoma, chondrosarcoma), osteoclastoma, neuroendocrine tumors, mesothelioma, chordoma, synovioma, schwanoma, meningioma, adenocarcinoma, melanoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, small cell lung carcinoma, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophageal cancer, tumors of the biliary tract, Ewing's tumor, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, testicular tumor, lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, multiple myeloma, Waldenstrom's macroglobulinemia, myelodysplastic disease, heavy chain disease, neuroendocrine tumors, Schwanoma, and other carcinomas, head and neck cancer, myeloid neoplasias such as acute myelogenous leukemias, including AML with maturation, AML without differentiation, acute promyelocytic leukemia, acute myelomonocytic leukemia, and acute monocytic leukemias, myelodysplastic syndromes, and chronic myeloproliferative disorders, including chronic myelogenous leukemia, tumors of the central nervous system, e.g., brain tumors (glioma, neuroblastoma, astrocytoma, medulloblastoma, ependymoma, and retinoblastoma), solid tumors (nasopharyngeal cancer, basal cell carcinoma, pancreatic cancer, cancer of the bile duct, Kaposi's sarcoma, testicular cancer, uterine, vaginal or cervical cancers, ovarian cancer, primary liver cancer or endometrial cancer, tumors of the vascular system (angiosarcoma and hemangiopericytoma), hematologic neoplasias and neoplastic-like conditions for example, Hodgkin's lymphoma; non-Hodgkin's lymphomas (Burkitt's lymphoma, small lymphocytic lymphoma/chronic lymphocytic leukemia, mycosis fungoides, mantle cell lymphoma, follicular lymphoma, diffuse large B-cell lymphoma, marginal zone lymphoma, hairy cell leukemia and lymphoplasmacytic leukemia), tumors of lymphocyte precursor cells, including B-cell acute lymphoblastic leukemia/lymphoma, and T-cell acute lymphoblastic leukemia/lymphoma, thymoma, tumors of the mature T and NK cells, including peripheral T-cell leukemias, adult T-cell leukemia/T-cell lymphomas and large granular lymphocytic leukemia, osteolytic bone cancers, and bone metastasis.

The present invention is further illustrated by reference to the following Examples. However, it should be noted that these Examples, like the embodiments described above, are illustrative and are not to be construed as restricting the scope of the invention in any way.

EXAMPLES

Example 1

Peptide Effects on Migration of Cancer Cell Lines

Protocol for a Migration Assay

CL1-5 cells, an aggressively metastatic cell line derived from a human adenocarcinoma, were cultured in RPMI 1640 media with 10% FBS, 37° C. at 95% Oxygen/5% $CO_2$ until ready for use. Transwell plates (24-well, 8-um pore size; Costar, Cambridge, Mass., USA) were used to conduct the migration assay. The lower chambers of the Transwell plates were filled with 600 µl of basal media containing 10% FBS. The cells ($1 \times 10^5$) were pretreated with 50 or 100 µM of the indicated test peptide for 30 min, and then suspended in 100 µl of basal media containing 1% BSA and added to the upper chamber, and the cells then were incubated at 37° C. for 12 hr. The cells on the upper surface of the filters were removed using cotton swabs, and the cells that migrated to the lower surface of the filters were washed, fixed, and stained with hematoxylin and counted under the microscope. The percent change in migration was determined by counting the number of cells that migrated to the lower surface of the filters. At least 3 separate microscopic fields were counted per membrane (n=4).

Alternative Transwell Method

Primary CL1-5 cells originated from human adenocarcinoma lung cancer. Transwell plates with 24-wells, 8-µ pore size (Costar, Cambridge, Mass., USA) were used to conduct the migration assay. The lower chambers of the transwell plates were filled with 600 of basal media containing 10% FBS. The cells ($1-2 \times 10^5$) were suspended in 100 µL of basal media containing 1% BSA. The test peptide at desired concentration was added to the upper chamber directly or after preincubation with cancer cells. The plates were then incubated at 37° C. for 12 hours. The cells on the upper surface of the filters were removed using cotton swabs. The cells that migrated to the lower surface of the filters were washed, fixed, and stained with hematoxylin and counted under the microscope. At least five separate microscopic fields are counted per membrane (n=3). The percent change in migration was determined by counting the number of cells that migrated to the lower surface of the filters.

The count means the actual number of cells which migrated to the lower chamber and counted by a light microscope at 40× magnification, presented as the mean number of cells in 10 randomly chosen fields for each treatment.

The "index" was calculated by dividing the number of cells that migrated in the presence of peptides by the number of cells that migrated randomly (control group). Index=control cell count/treated cells count. This calculation can reflect the extent that the migration of cells was blocked by 30 minute pretreatment with MANS-related peptides.

FIG. 1 displays a cell count field of a negative control after a migration time of 12 hours.

FIG. 2A displays a cell count field obtained after pretreatment with 50 µmolar of MANS peptide followed by a migration time of 12 hours.

FIG. 2B displays a cell count field obtained after pretreatment with 100 µmolar of MANS peptide followed by a migration time of 12 hours.

FIG. 3A displays a cell count field obtained after pretreatment with 50 µmolar of RNS peptide followed by a migration time of 12 hours.

FIG. 3B displays a cell count field obtained after pretreatment with 100 µmolar of RNS peptide followed by a migration time of 12 hours.

Figures 4A, 4B:
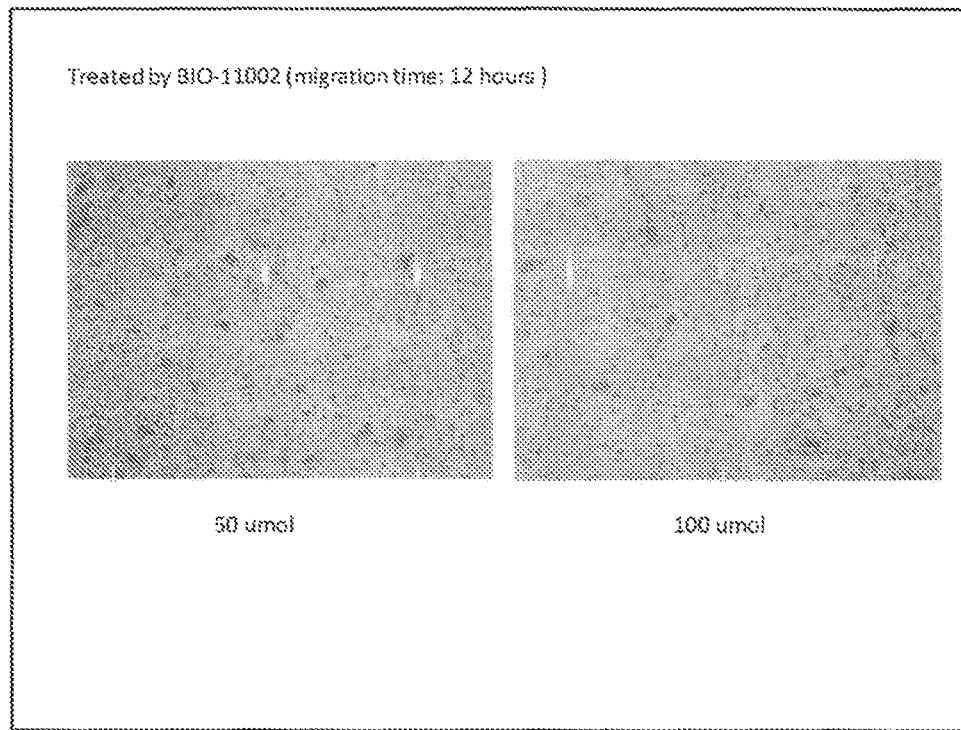
FIG. 4A displays a cell count field obtained after pretreatment with 50 μmolar of MANS-related peptide BIO-11002 followed by a migration time of 12 hours.
FIG. 4B displays a cell count field obtained after pretreatment with 100 μmolar of MANS-related peptide BIO-11002 followed by a migration time of 12 hours.

FIG. 4A displays a cell count field obtained after pretreatment with 50 µmolar of MANS-related peptide BIO-11002 (N-myristoyl—SEQ ID NO: 106-NH2) followed by a migration time of 12 hours.

FIG. 4B displays a cell count field obtained after pretreatment with 100 µmolar of MANS-related peptide BIO-11002 followed by a migration time of 12 hours.

Figures 5A, 5B:
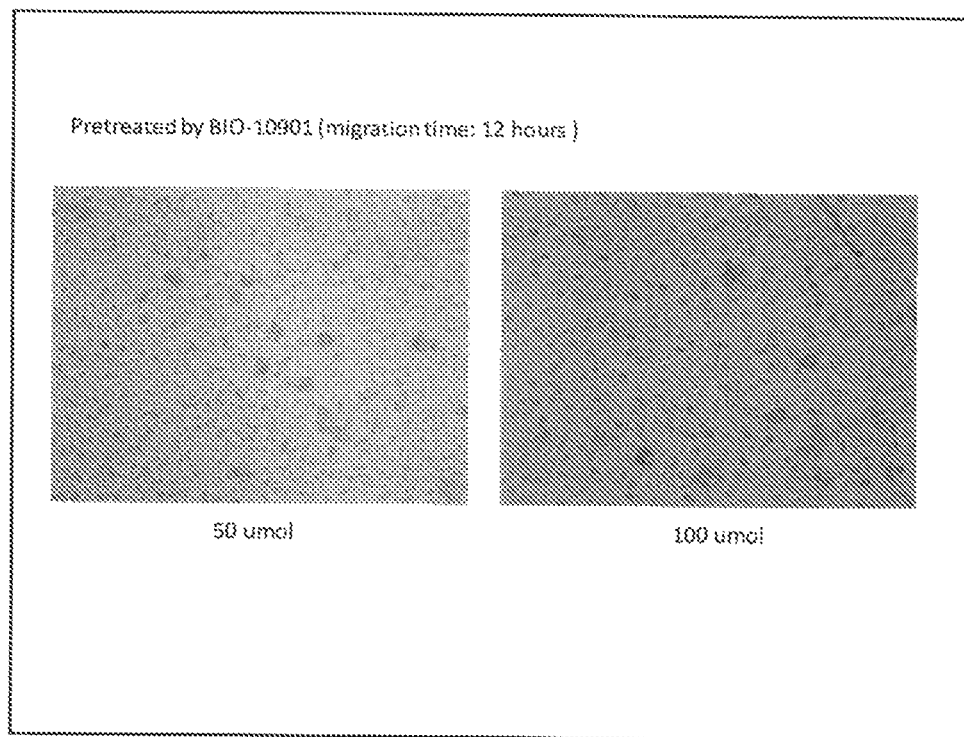
FIG. 5A displays a cell count field obtained after pretreatment with 50 μmolar of MANS-related peptide BIO-10901 followed by a migration time of 12 hours.
FIG. 5B displays a cell count field obtained after pretreatment with 100 μmolar of MANS-related peptide BIO-10901 followed by a migration time of 12 hours.

FIG. 5A displays a cell count field obtained after pretreatment with 50 µmolar of MANS-related peptide BIO-10901 (N-acetyl—SEQ ID NO: 121) followed by a migration time of 12 hours.

FIG. 5B displays a cell count field obtained after pretreatment with 100 µmolar of MANS-related peptide BIO-10901 followed by a migration time of 12 hours.

Figures 6A, 6B:
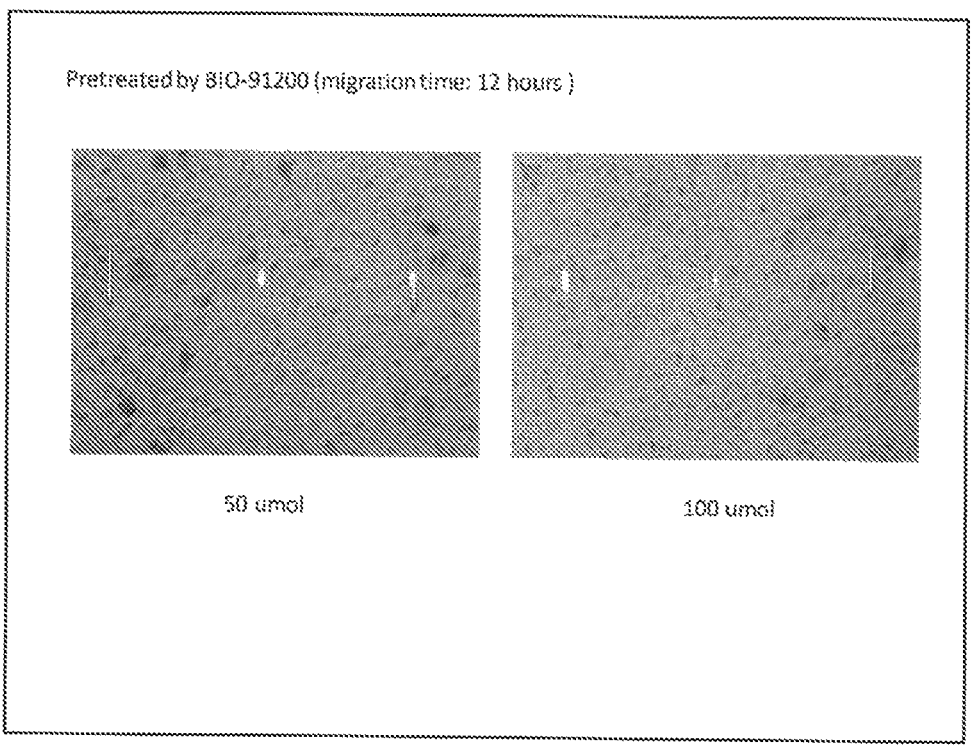
FIG. 6A displays a cell count field obtained after pretreatment with 50 μmolar of MANS-related peptide BIO-91200 followed by a migration time of 12 hours.
FIG. 6B displays a cell count field obtained after pretreatment with 100 μmolar of MANS-related peptide BIO-91200 followed by a migration time of 12 hours.

FIG. 6A displays a cell count field obtained after pretreatment with 50 µmolar of MANS-related peptide BIO-91200 (N-myristoyl—SEQ ID NO: 219) followed by a migration time of 12 hours.

FIG. 6B displays a cell count field obtained after pretreatment with 100 µmolar of MANS-related peptide BIO-91200 followed by a migration time of 12 hours.

FIG. 7A displays migrated cell numbers obtained 12 hours after pretreatment at 50 µmolar with MANS peptide, RNS peptide, and MANS-related test peptides BIO-11002 (SEQ ID NO: 6), BIO-10901 (SEQ ID NO: 121), and BIO-9120 (SEQ ID NO: 219), and control (no peptide). For MANS peptide, the cell number was approximately 40; for RNS peptide, the cell number was approximately 95; for BIO-11002 (SEQ ID NO: 106), the cell number was approximately 50); for BIO-10901 (SEQ ID NO: 121), the cell number was approximately 60; and for BIO-91200 (SEQ ID NO: 219), the cell number was approximately 65. Each of the MANS-related peptides MANS, BIO-11002, BIO-10901, and BIO-91200 demonstrated significantly reduced migrated cell numbers of the aggressive human NSCLC cell line (CL1-5) relative to control and to RNS random sequence peptide.

FIG. 7B displays migrated cell numbers obtained 12 hours after pretreatment at 100 µmolar with MANS peptide, RNS peptide, and MANS-related test peptides BIO-11002 (SEQ ID NO: 106), BIO-10901 (SEQ ID NO: 121), and BIO-91200 (SEQ ID NO: 219), and control (no peptide). For MANS peptide, the cell number was approximately 20); for RNS peptide, the cell number was approximately 90; for BIO-11002 (SEQ ID NO: 106), the cell number was approximately 25; for BIO-10901 (SEQ ID NO: 121), the cell number was approximately 35; and for BIO-91200 (SEQ ID NO: 219), the cell number was approximately 40; for the control (no peptide), the cell number was approximately 90. Each of the MANS-related peptides MANS, BIO-11002, BIO-10901, and BIO-91200 demonstrated significantly reduced migrated cell numbers of the aggressive human NSCLC cell line (CL1-5) relative to control and to RNS random sequence peptide.

FIG. 8A displays the migration index of aggressive human NSCLC cell line cells, wherein a higher value of the migration index signifies less migration after pretreatment with a peptide or peptide composition of the invention at 50 µmolar followed by 12 hours of treatment according to the protocol. The following are the migration index values: control=1; MANS peptide=approximately 2.5; RNS peptide=approximately 1.1; BIO-11002=approximately 2.7; BIO-10901=approximately 1.75; and BIO-91200=approximately 1.7. Each of the MANS-related peptides MANS, BIO-11002, BIO-10901, and BIO-91200 demonstrated significantly increased migration index numbers relative to control and to RNS peptide.

FIG. 8B displays the migration index of aggressive human NSCLC cell line cells, wherein a higher value of the migration index signifies less migration after pretreatment with a peptide or peptide composition of the invention at 100 µmolar followed by 12 hours of treatment according to the protocol. The following are depicted migration index values: control=1; MANS peptide=approximately 4.3; RNS peptide=approximately 1; BIO-11002=approximately 3.8; BIO-10901=approximately 2.7; and BIO-91200=approximately 2.4. Each of the MANS-related peptides MANS, BIO-11002, BIO-10901, and BIO-91200 demonstrated significantly increased migration index numbers relative to control and to RNS peptide.

Figure 9:
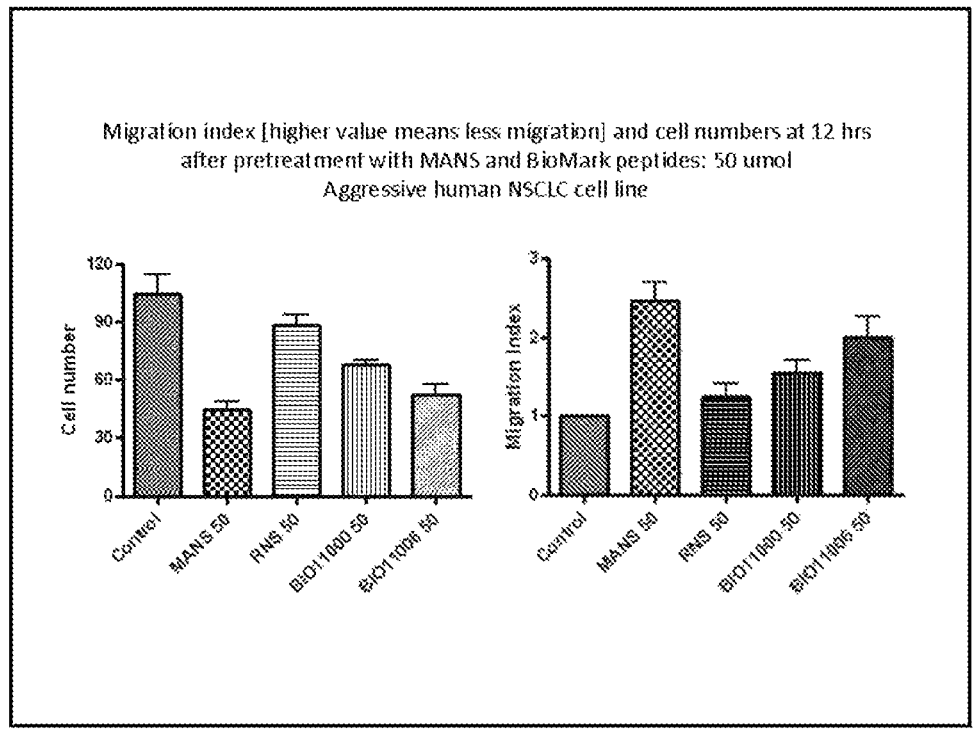
FIG. 9 graphically displays respective cell numbers (left panel) and migration index number (right panel) for MANS, RNS, BIO-11000, or BIO-11006, or control (no peptide) in experiments using 50 μmolar of the indicated peptide and the aggressive human NSCLC cell line.

FIG. 9 graphically displays side-by-side respective cell numbers and migration index number results of 50 µmolar peptide pretreatment in experiments using the aggressive human NSCLC cell line (CL1-5). Control with no peptide pretreatment gives a cell number of approximately 105; and migration index number=1.0 Results after 50 µmolar pretreatment with MANS peptide followed by 12 hours according to the protocol gives a cell number of approximately 45; and migration index of approximately 2.5. Results after 50 µmolar pretreatment with RNS peptide gives a cell number of approximately 90; and migration index of approximately 1.3. Results after 50 µmolar pretreatment with BIO-11000 gives a cell number of approximately 70; and migration index of approximately 1.5. Results after 50 µmolar pretreatment with BIO-11006 give cell number of approximately 50; and migration index of approximately 2. The results demonstrate that higher values of migration index are associated with less migration, and less migration is associated with higher values of migration index. Each of the MANS-related peptides MANS, BIO-11000, and BIO-11006 demonstrated decreased migrated cell numbers and increased migration index numbers relative to control and to RNS peptide.

Figure 10:
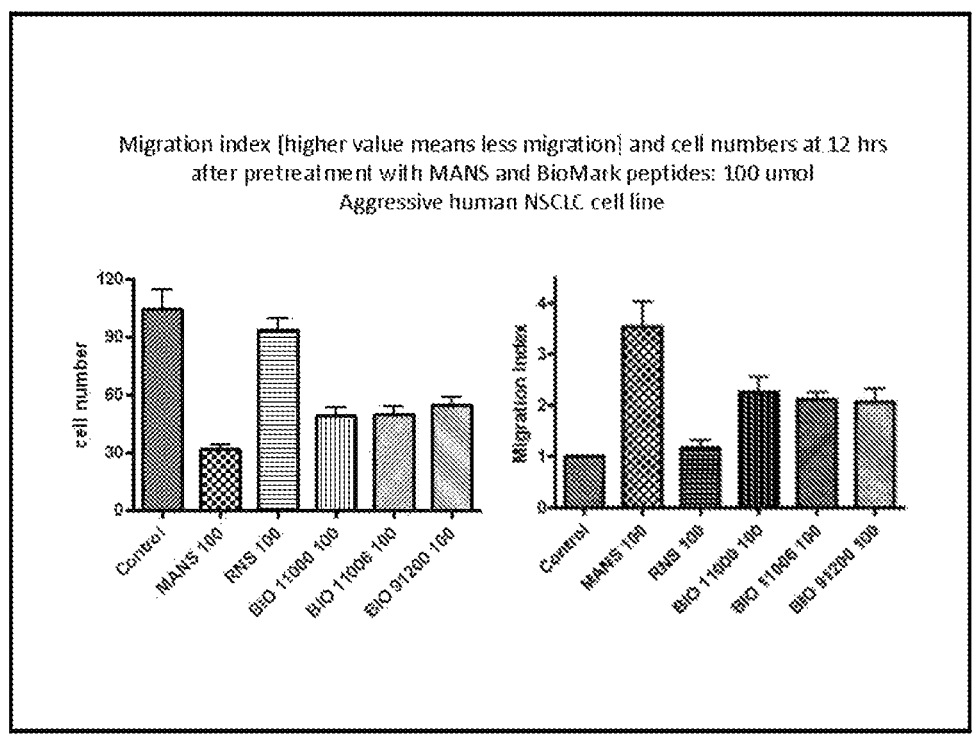
FIG. 10 graphically displays respective cell numbers (left panel) and migration index number (right panel) for MANS, RNS, BIO-11000, BIO-11006, BIO-91200, or control (no peptide) in experiments using 100 μmolar of the indicated peptide and the aggressive human NSCLC cell line.

FIG. 10 graphically displays side-by-side respective cell numbers and migration index number results for 100 µmolar peptide pretreatment in experiments using the aggressive human NSCLC cell line (CL1-5). Control with no peptide pretreatment gives a cell number of approximately 105; and migration index number=1.0. Results after 100 µmolar pretreatment with MANS peptide followed by 12 hours according to the protocol to gives a cell number of approximately 35; and migration index of approximately 3.5. Results after 100 µmolar pretreatment with RNS peptide gives a cell number of approximately 95; and migration index of approximately 1.2. Results after 100 µmolar pretreatment with BIO-11000 gives a cell number of approximately 50; and migration index of approximately 2.3. Results after 100 µmolar pretreatment with BIO-11006 gives a cell number of approximately 50; and migration index of approximately 2.1. Results after 100 µmolar pretreatment with BIO-91200 gives a cell number of approximately 55; and migration index of approximately 2.1. The results demonstrate that higher values of migration index are associated with less cell migration, and less cell migration is associated with higher values of migration index. Each of the MANS-related peptides MANS, BIO-11000, BIO-11006, and BIO-91200 demonstrated decreased migrated cell numbers and increased migration index numbers relative to control and to RNS peptide.

Example 2

Inhibition of Lung Cancer Metastasis by MANS Peptide or BIO-11006 Using Orthotopic Lung Injection Xenograph Model The metastatic activity of cancer cells in vivo after treatment with MANS peptide or BIO-11006 was assessed in the orthotopic lung injection xenograph model. After pretreatment with either PBS, or PBS+MANS, BIO-11006 (SEQ ID NO: 106), or the control RNS peptide at 100 µM for 4 hours, PC-9 cells were injected into the left lobe of the lung of nude mice. Seven days later, these mice were given systemic treatment with either PBS only (Con), RNS (additional control peptide), MANS or BIO-11006 at 50 nmoles per intraperitoneal injection once every three days. At 25 days (6 injections) post—seeding of these tumor cells, mice were sacrificed and the number of metastasized tumor nodules in the contralateral lung and other organs was counted. As shown in Table 3 below, MANS, RNS or BIO-11006—treated groups showed no difference in average size of the tumor at the site of injection compared to PBS—treated or to each other, suggesting that these treatments do not affect tumorigenesis. However, a significant decrease of metastatic nodules was noted in the contralateral lung and other organs in the MANS and BIO-11006—treated mice compared to the PBS- or RNS-treated groups; in fact, treatment with the MANS or BIO-11006 peptides essentially totally blocked all metastasis from the tumor to other lung sites as well as to other organs.

These in vivo results support the concept that inhibition of MARCKS function by MANS-related peptides can reduce the metastatic spread of lung cancer cells in vivo.

Example 3

Peptide Effects on Migration of Cancer A549 Cell Lines

The human adenocarcinoma-derived alveolar epithelial cell line A549 (an invasive cell line) was obtained from the American Type Culture Collection (ATCC) and was cultured in RPMI-1640 supplemented with 10% fetal bovine serum and 100 U/ml penicillin/streptomycin, in 75 $cm^2$ tissue culture flasks. The cells reached confluence by the third day of culture at 37° C. in an atmosphere of 95% air and 5% $CO_2$ and were maintained by serial passage.

The test peptides (MANS, RNS, BIO-11006, BIO-11000, BIO-11002, BIO-91200, and BIO-10901) were dissolved in PBS at a pH of 7.0; slow vortex mixing for about two hours aided solubility.

Transwell plates (24-well, 8-µM pore size; Costar, Cambridge, Mass., USA) were used to conduct the migration assay. The lower chambers of the transwell plates were filled with 600 µl of basal medium containing 10% FBS. The cells ($1\times10^5$) were suspended in 100 µl of basal medium containing 1% BSA and added to the upper chamber, and the plates incubated at 37° C. with 5% $CO_2$ for 12 hr in PBS (control), or the indicated test peptides at 10, 25 or 50 µM. The cells on the upper surface of the filters were removed using cotton swabs. The cells that migrated to the lower surface of the filters were washed, fixed, and stained with hematoxylin and counted under the microscope. The percent change in migration is determined by counting the number of cells that migrated to the lower surface of the filters. At least four separate microscopic fields are counted per membrane, with a total of three replicate experiments at each concentration. The statistics software "Prizm" was used for data analysis.

Figure 11:
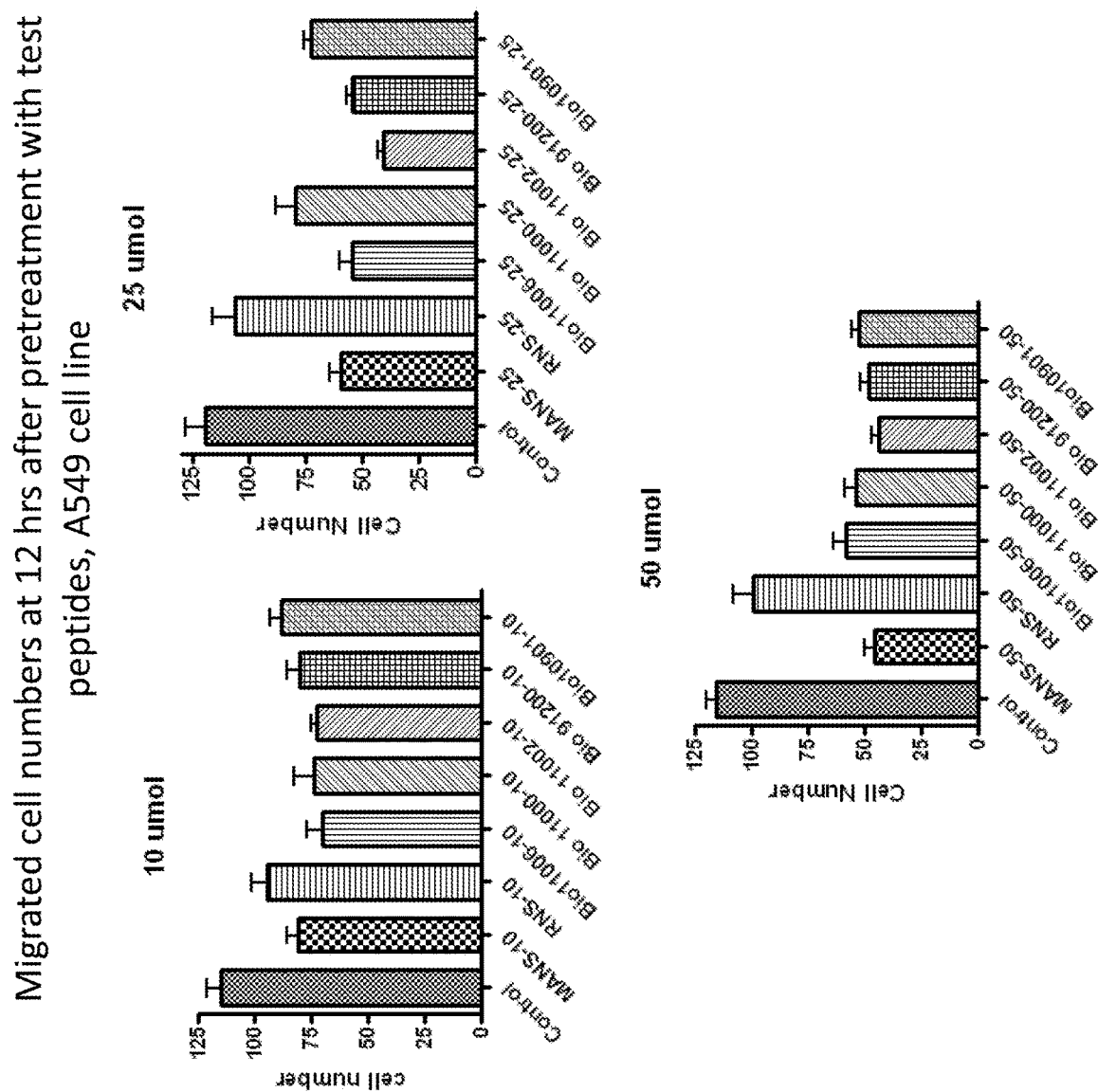
FIG. 11 shows the migrated cell numbers 12 hours after pretreatment of A549 cells with no peptide or with the indicated test peptide (MANS, RNS, BIO-11006, BIO-11000, BIO-11002, BIO-91200, or BIO-10901) at 10 μmolar (top left panel), 25 μmolar (top right panel) or 50 μmolar (bottom panel) of peptide.

As shown in FIG. 11, treatment with each of the test peptides resulted in a reduced cell number after treatment relative to control (no peptide) or to RNS peptide. At 50 µm, each of the MANS-related peptides MANS, BIO-11006, BIO-11000, BIO-11002. BIO-91200, and BIO-10901 demonstrated decreased migrated cell numbers and increased migration index numbers relative to control and to RNS peptide. At lower concentrations, the effect of several MANS-related peptides was significantly different even in comparison to MANS peptide. In particular, at 25 µm, treatment with BIO-11006, BIO-11002, or BIO-91200 resulted in a significantly reduced cell numbers in compari-

TABLE 3

The suppressive effect of MARCKS-related peptides on cancer metastasis in vivo

| Group | Tumor Size (mm) Mean ± SE | No. of Metastatic Lung Tumors Mean ± SE (L't; R't) | Metastases (affected mice/total mice) | | | |
|---|---|---|---|---|---|---|
| | | | Heart | Spleen | Intestines | Diaphragm |
| PBS (n = 3) | 1.50 ± 0.26 | 1.67 ± 0.29; 5.67 ± 0.77 | 1/1 | 2/3 | 1/3 | 2/3 |
| RNS (n = 4) | 1.72 ± 0.41 | 1.00 ± 0.40; 5.75 ± 2.01 | 3/4 | 2/4 | 1/4 | 3/4 |
| MANS (n = 4) | 1.48 ± 0.54 | 0; 0 | 0/4 | 0/4 | 0/4 | 0/4 |
| BIO-11006 (n = 2) | 1.61 ± 0.37 | 0; 0 | 0/2 | 0/2 | 0/2 | 0/2 | son to control (no peptide) or control RNS peptide, as well as in comparison to MANS peptide (FIG. 11).

Taken together, the results of the studies showed that the MANS-related peptides can block migration of aggressive cancer cell lines, and that several different MANS-related peptides exhibited an effect on migration of at least three different cancer cell lines. The results of the studies also showed that at least two different MANS-related peptides were able to block or inhibit metastasis of cancer cells injected into mammals (i.e., mice).

Example 4

Effects of Peptide BIO-11006 in Lung Cancer Implantation

Figure 12:
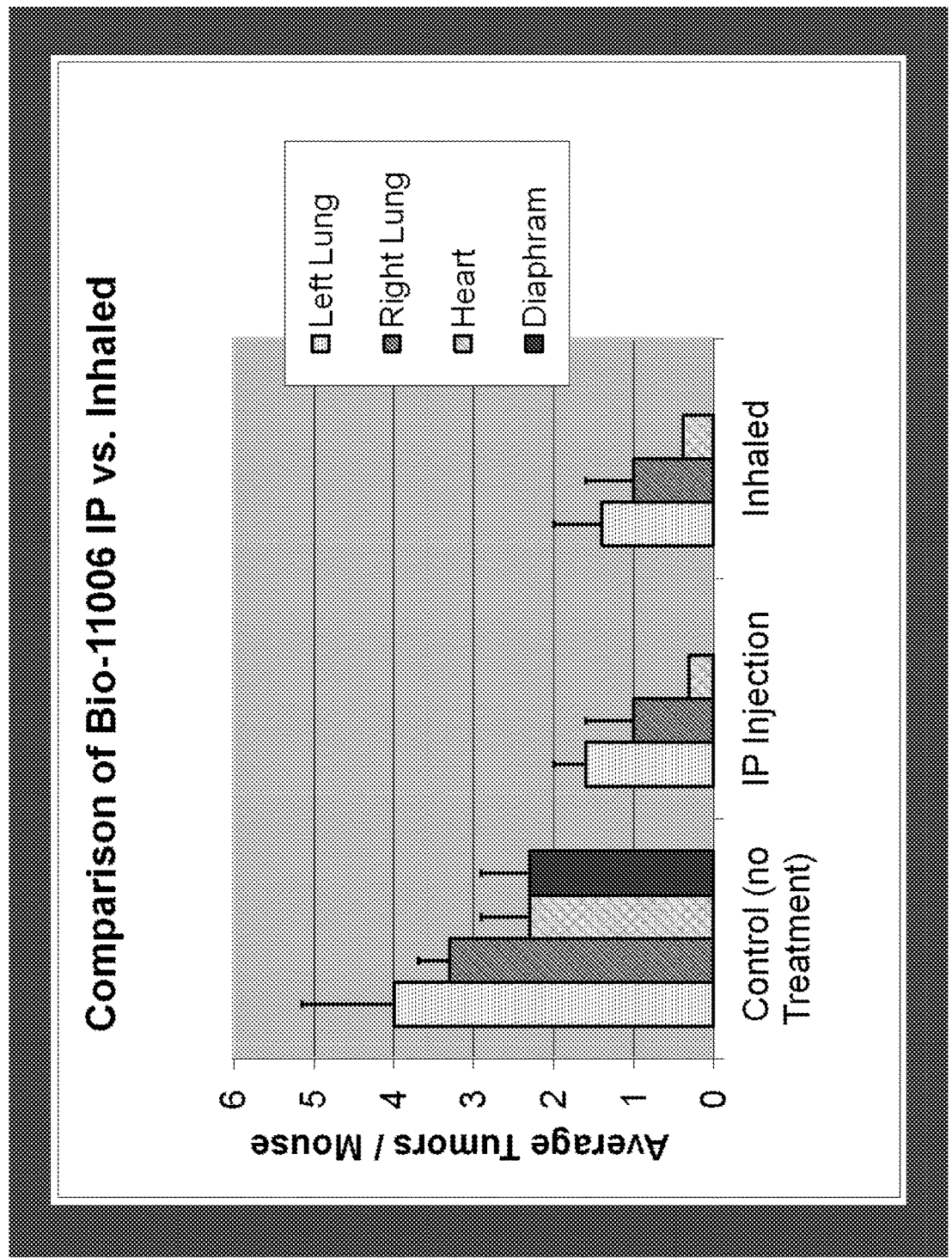
FIG. 12 shows the average number of tumors per mouse in the left lung, right lung, heart, and diaphragm in animals treated with BIO-11006. BIO-11006 (100 μM in PBS) was administered once daily for 22 days, starting at 3 days post cancer cell inoculation, via intraperitoneal injection (50 μL) or inhalation (30 mins, Nebulizer Delivery System, Aeroneb Lab).

In this study, inhibition of lung cancer metastasis by peptide BIO-11006 in an orthotopic lung cancer implantation model in SCID mice assessed. Human adenocarcinoma cells (PC-9) ($1-2 \times 10^5$) were suspended in 40 µL of PBS, pH 7.4 containing 0.5 mg/mL of Matrigel™ (BD Bioscience) and injected into the left lung of SCID mice (n=3) using a syringe with 29 gauge needle. BIO-11006 (100 µM, in PBS) was administered either (a) by i.p. injection (50 µL) once daily for 22 days starting at 3 days post cancer cell inoculation or (b) by aerosol inhalation using a Nebulizer Delivery System (Aeroneb Lab) over 30 min once daily for 22 days starting at 3 days post cancer cell inoculation. The results of the study are depicted in FIG. 12, which graphically displays the average number of tumors in the right lung, heart, and diaphragm as a function of the route of administration of the test compound (ip injection versus inhalation). Both i.p. and aerosol administration of BIO-11006 reduced cancer cell metastasis by more than 50% in the right lung and heart, and 100% in the diaphragm. Thus, both routes of administration had significant inhibitory effects on cancer cell metastasis.

Example 5

Inhibition of Lung Cancer Metastasis

Figure 13:
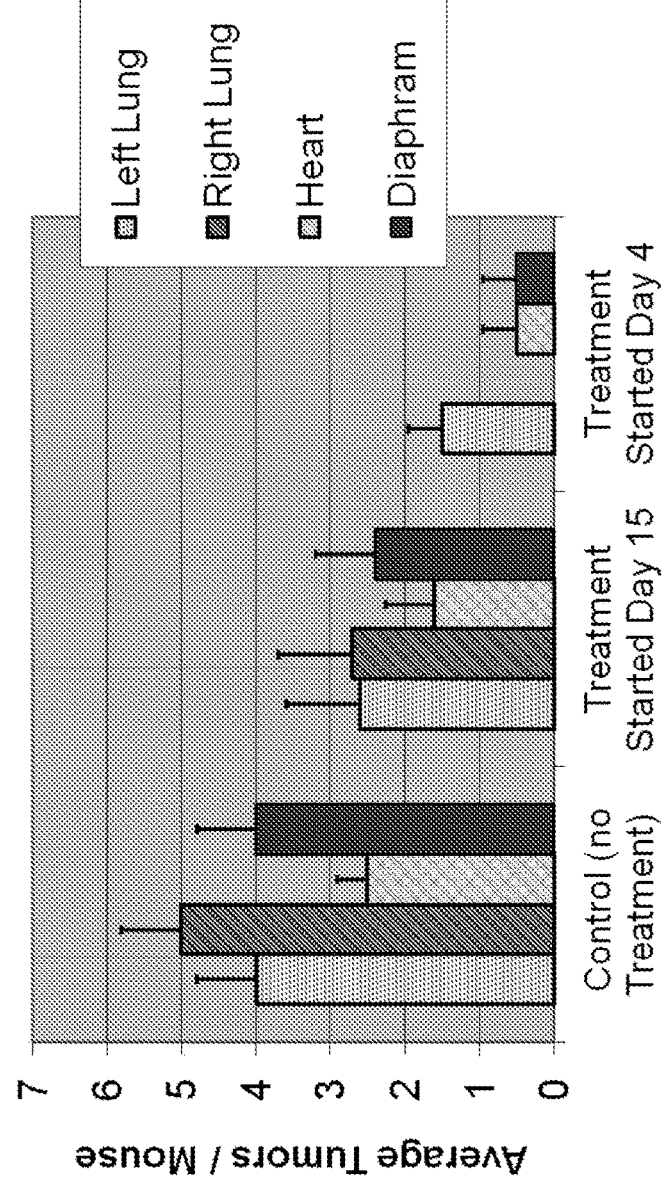
FIG. 13 shows the average number of tumors per mouse in the left lung, right lung, heart, and diaphragm in mice administered BIO-11006 (100 μM in PBS) by inhalation using a Nebulizer Delivery System (Aeroneb Lab) over 30 days, once daily beginning on Day 15 or on Day 4 relative to injection of human adenocarcinoma cells (PC-9).
Figure 14:
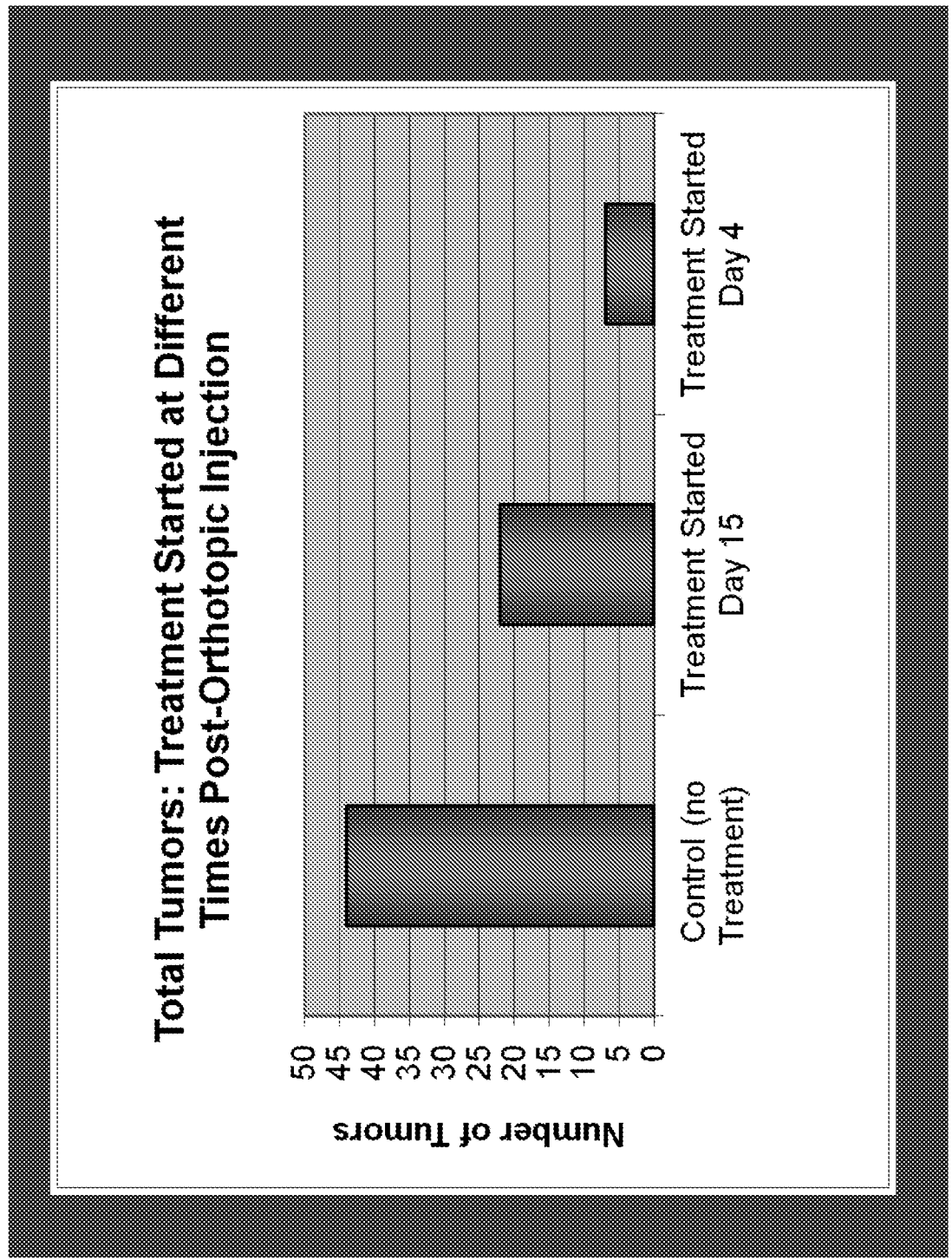
FIG. 14 shows the total number of tumors in mice administered BIO-11006 (100 μM in PBS) by inhalation using a Nebulizer Delivery System (Aeroneb Lab) over 30 days, once daily beginning on Day 15 or on Day 4 relative to injection of PC-9 cells.

In this study, inhibition of lung cancer metastasis by BIO-11006 was investigated in an orthotopic lung cancer implantation model in SCID mice. Human adenocarcinoma cells (PC-9) ($1-2 \times 10^5$) were suspended in 40 µL of PBS containing 0.5 mg/mL of Matrigel™ (BD Bioscience) and injected into the left lung of SCID mice (n=3) using a 29 gauge needle. BIO-11006 was administered starting either 4 days or 15 days post cancer cell inoculation by aerosol using 100 µM solution in PBS by Nebulizer Delivery System (Aeroneb Lab) over 30 min once daily for 25 days post cancer cell inoculation. At end of the experiment, the mice were sacrificed and lungs, heart, and diaphragm tissues collected and number of tumor nodules in each tissue measured. The results of this experiment are presented graphically in FIGS. 13 and 14. FIG. 13 shows that when the treatment was started at 4 days post inoculation of cancer cells, the tumor metastasis was inhibited by 60-90% in the left lung, heart, and diaphragm, and by 100% in the right lung. When the treatment was initiated at 15 days post inoculation of cancer cells, the inhibition of tumor metastasis was about 50% in the lungs, heart, and diaphragm. FIG. 14 depicts the total number of tumor nodules found in all tissues when peptide treatment was started at 15 days post cancer cell inoculation or 4 days post cancer cell inoculation. As shown in FIG. 14, peptide treatment starting at 15 days post cancer cell inoculation resulted in reduced tumor nodules, and peptide treatment starting at 4 days post inoculation resulted in even further reduced tumor nodules.

Example 6

Anti-Metastatic Efficacy of Peptides

This example demonstrates the anti-metastatic efficacy of test compounds of the invention in SCID mice bearing human lung adenocarcinoma cells. Female NOD.CB17-Prkdc$^{scid}$/NCrHsd, Mus musculus mice (Harlan, The Netherlands), housed in individually ventilated cages, were randomized into six groups of eight mice each. A549 cells ($2.5 \times 10^6$) were injected into the mice via the tail vein. The control group received aerosolized vehicle PBS; while the groups 2 and 3 received the aerosolized test compound BIO-11006 either from −1 day before the cancer cells injection (group 2) or from +3 days after the cancer cell injection (group 3) on every other day for 7 weeks via nebulizer (Aeroneb Lab). Groups 4 and 5 received the aerosolized test compound MANS peptide either from −1 day before the cancer cell line injection (group 4) or from +3 days after the cell line injection (group 5) on every other day for 7 weeks via a nebulizer (Aeroneb Lab). For aerosol delivery, solution of each test compound (100 µM) was prepared in PBS, pH 7.0. For each treatment, 5 mL of test compound solution was aerosolized over 30 minutes into a chamber containing four mice at a time. The mice were monitored for body weight every other day for 7 weeks.

Figure 15:
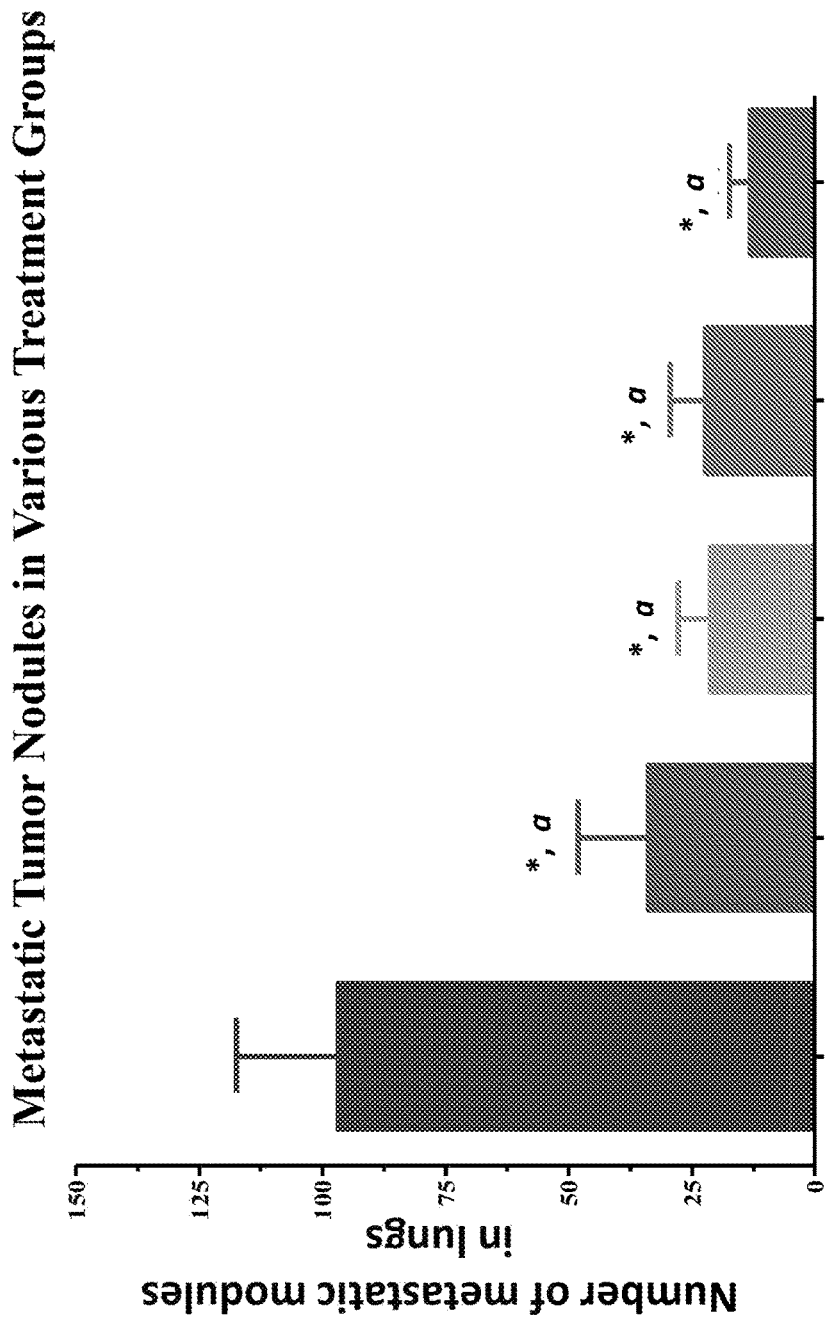
FIG. 15 depicts the number of metastatic nodules found in mice treated with every other day with vehicle control, aerosolized BIO-11006 beginning on day −1 or day +3 relative to A549 cancer cell injection, or aerosolized MANS beginning on day −1 or day +3 relative to A549 cancer cell injection. Aerosolized peptides (100 μM in PBS) were administered by inhalation using the Nebulizer Delivery System (Aeroneb Lab). *, $p<0.05$, statistically significant compared to control group; a, statistically non-significant in comparison among the groups.

One group of mice (n=7) served as normal control. These were untreated naïve mice used to monitor the health status of mice during the study period. All animals from all groups were sacrificed on Day 53. The results are provided in Table 4 and FIG. 15. FIG. 15 compares number of metastatic nodules in lungs after respective administration of BIO-11006 and MANS peptide on Day 53 following A549 cell injection. Table 4 shows the number of metastatic nodules in the lungs, as well as the number of animals with focal tumor nodules and/or distant metastasis. Overall, the test peptides showed substantial inhibition of tumor metastasis (70-80%) in animals administered BIO-11006 or MANS peptide starting on day −1 or Day +3 relative to A549 cell injection (FIG. 15). Moreover, the number of metastatic nodules in treated mice was significantly reduced relative to vehicle control recipients, and none of the treated mice exhibited evidence of distant metastases (Table 4). There were few focal tumor nodules in 7/8 of mice treated with BIO-11006 peptide starting at either Day −1 or Day +3 relative to A549 cell injection.

TABLE 4

Metastatic nodules and distant metastasis in mice treated with BIO-11006 or MANS

| Group | No. of metastatic nodules in lungs Mean ± SEM | Remarks |
|---|---|---|
| Vehicle Control | 97 ± 21 | Multi-focal tumor nodules in all animals (8/8) Evidence of distant metastasis in diaphragm and sternum (2/8) |

TABLE 4-continued

Metastatic nodules and distant metastasis
in mice treated with BIO-11006 or MANS

| Group | No. of metastatic nodules in lungs Mean ± SEM | Remarks |
|---|---|---|
| BIO-11006 peptide (−1 Day treatment group) | 34 ± 14 | Few focal tumor nodules in 7/8 animals<br>No distant metastasis |
| BIO-11006 peptide (+3 Day treatment group) | 21 ± 6 | Few focal tumor nodules in 7/8 animals<br>No distant metastasis |
| MANS peptide (−1 Day treatment group) | 22 ± 7 | Few focal tumor nodules in 4/8 animals<br>No distant metastasis |
| MANS peptide (+3 Day treatment group) | 13 ± 4 | Few focal tumor nodules in 7/8 animals<br>No distant metastasis |

Example 7

Anti-Metastatic Activity of MANS-Related Peptides in Murine Melanoma

In this study, the relative anti-metastatic activity of MANS-related peptides administered by four different routes is determined using a syngeneic mouse model. Murine melanoma cell line B16F10 $2\times10^6$ cells in 200 µl of cell suspension in DMEM media is injected in the footpad or between the skin and cartilage on the dorsal side of the ear; or by intravenous, intramuscular, or intraperitoneal injection.

Two days after cell inoculation, animals are randomized and divided into groups consisting of n=10 in each group. Animals in different groups are administered with MANS-related peptide by intraperitoneal (ip), intravenous (iv), or intramuscular (im) routes respectively at a dose of about 6.25 mg/kg. In some groups, animals are treated by inhalation route (5 ml of 0.1 mM MANS-related peptide in PBS) using preclinical nebulizer (Aeroneb Lab; Aerogen). One group of mice serves as vehicle control and treated with PBS by im route. Peptides are administered every other day for 6 weeks.

Tumor scoring is done weekly. After 6 weeks of treatment, all animals are humanely sacrificed and the lymph nodes & other tissue samples are collected, fixed in formalin and subjected to histopathology to assess the presence of metastatic melanoma cells. Clinical toxic signs and symptoms are assessed during the 6 wee administration period. Tumor burden and mortalities are assessed at the end of the study period. The results of the study will show that MANS-related peptides inhibit tumor metastasis in a murine melanoma model.

Example 8 siRNA Knockdown of MARCKS in Cancer Cells

Figure 16:
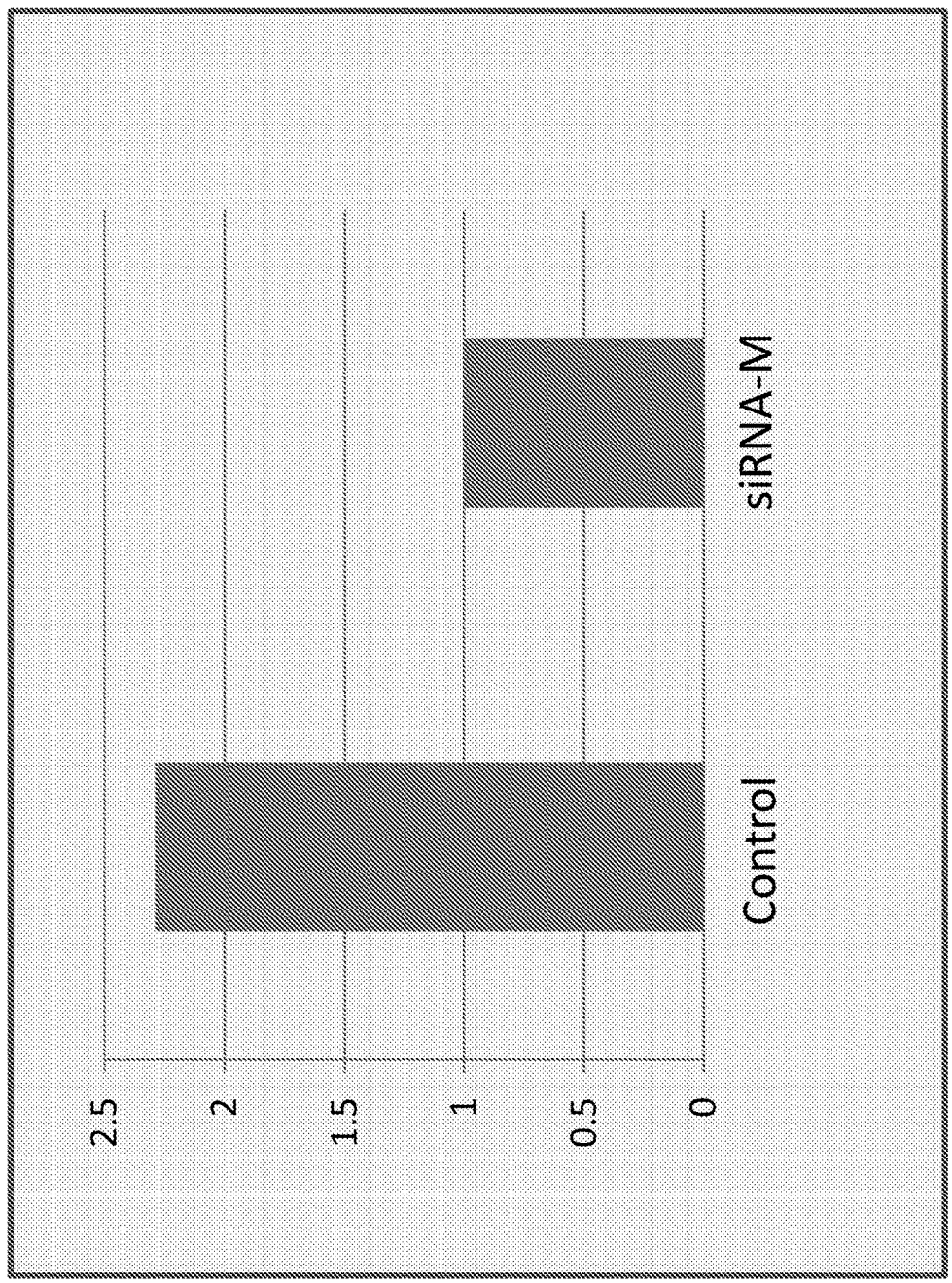
FIG. 16 shows the level of MARCKS protein following administration of 100 nM MARCKS siRNA or control siRNA in PC9 cells.
Figure 17:
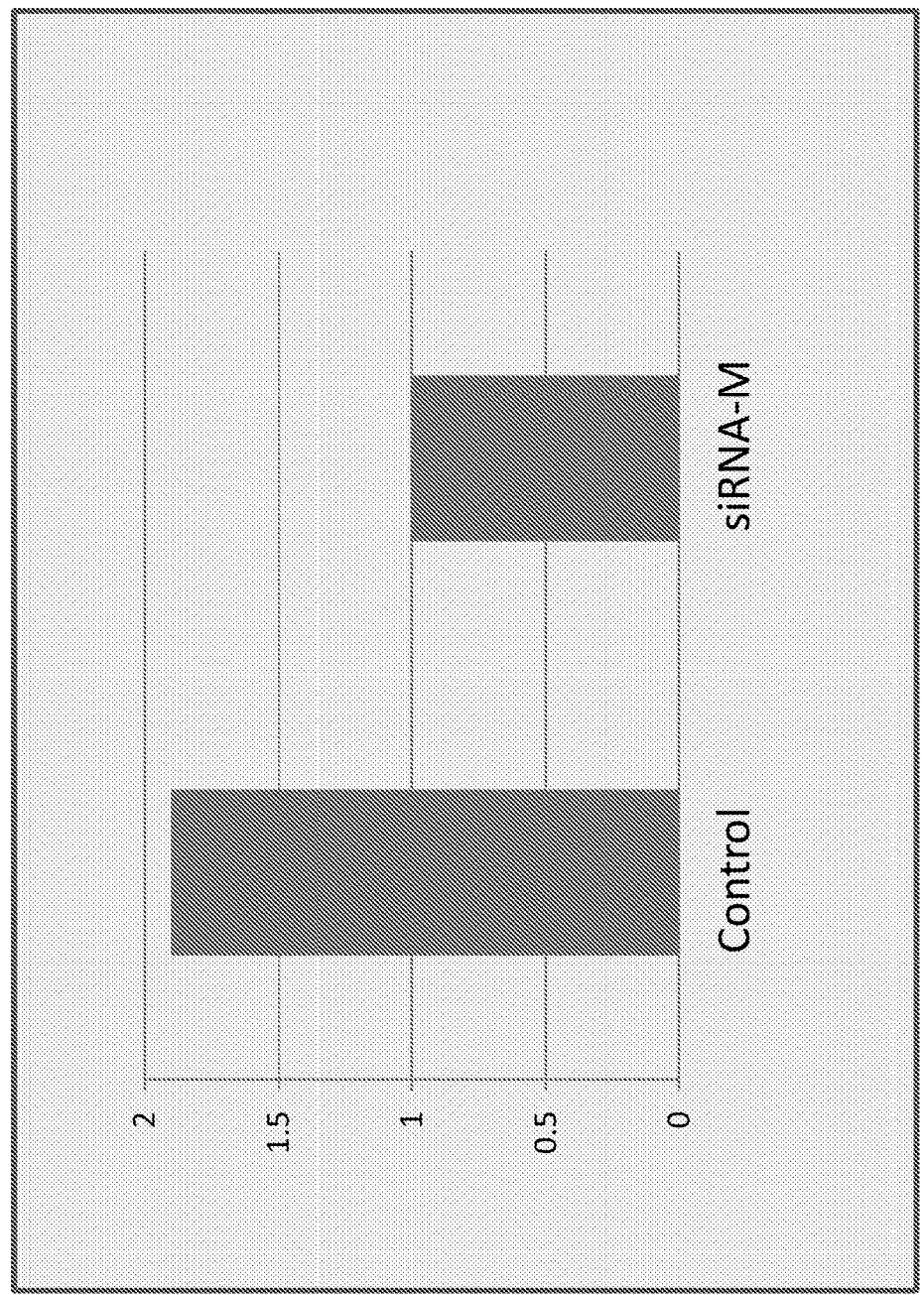
FIG. 17 shows the level of MARCKS protein following administration of 100 nM MARCKS siRNA or control siRNA in A549 cells.

This study was conducted to determine the effects of siRNA knockdown of MARCKS expression on migration of cancer cells. PC-9 or A-549 human lung cancer cells were seeded in plastic wells and cultured until cells reached 70% confluence. Cells were then transfected with 100 nM of MARCKS siRNA or control siRNA (100 nM) from Ambion (Austin, Tex.) by using the DharmaFECT DuoTransfection reagent (Dharmacon, Lafayette, Colo.). After 72 hours, the cells were harvested and equivalent amounts of proteins separated by SDS/PAGE for immunoblot analysis using MARKS specific antibodies. Western blot analysis was performed to confirm siRNA-induced down regulation of endogenous MARCKS. As shown in FIGS. 16 and 17, MARCKS protein was knocked down by approximately 60% in PC9 cells (FIG. 16) and approximately 50% in A549 cells (FIG. 17) compared to cells treated with control siRNA.

The effects MARCKS knockdown by siRNA on cell migration were determined using a transwell assay. Following siRNA knockdown, PC-9 or A549 cells were cultured in RPMI 1640 medium with 10% FBS at 37° C., with 5% CO2. Transwell® plates (24-well, 8-um pore size) were used for the migration assays. The lower chambers contained 600 µl basal medium+10% FBS. Cells ($1\times10^5$) were suspended in 100 µl of basal medium+1% BSA and added to the upper chamber; plates were incubated for 12 hr. Cells that migrated to the lower surface of the filters were stained with hematoxylin and counted. At least 3 separate microscopic fields were counted per membrane.

Figure 18:
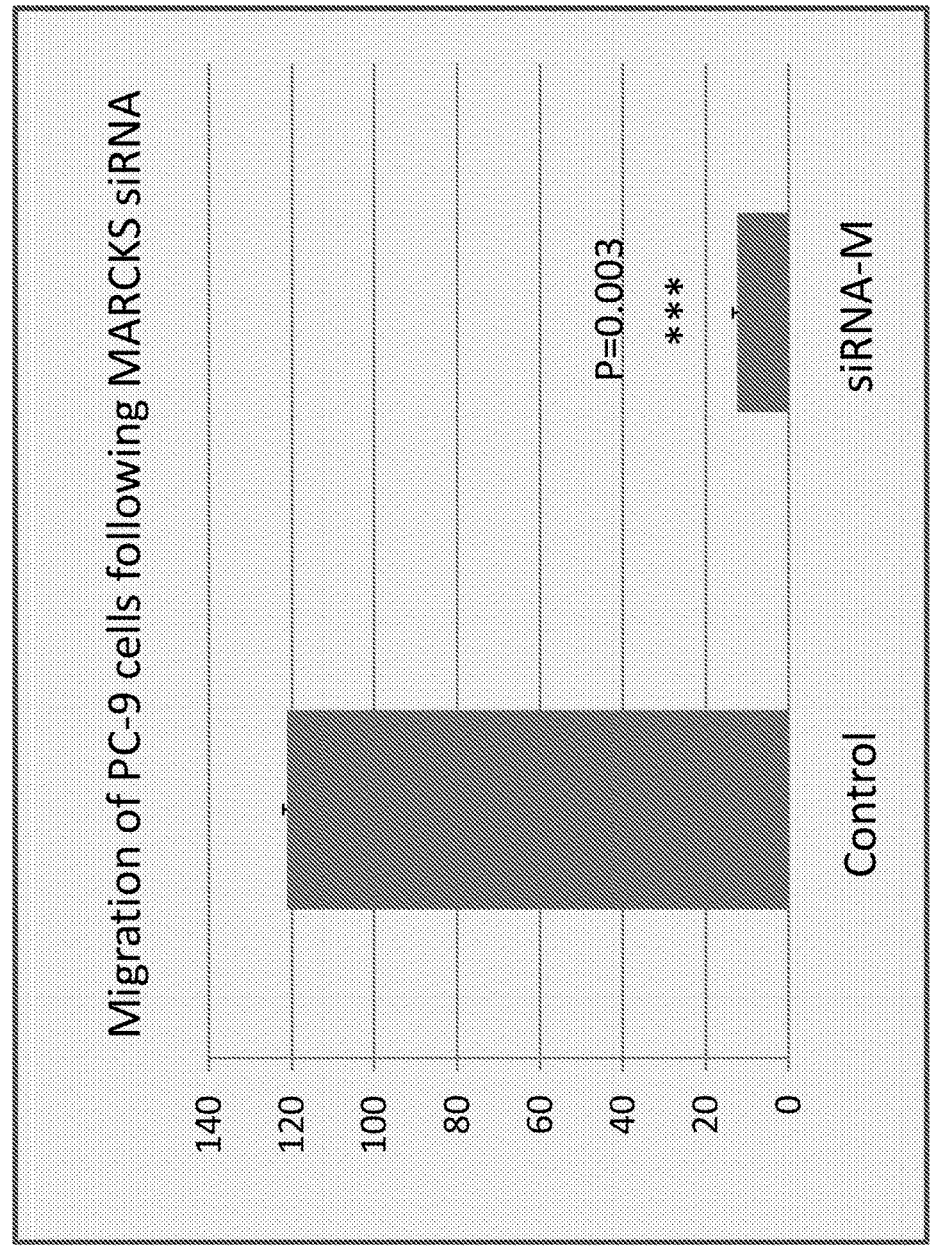
FIG. 18 shows the migration of PC9 cancer cells following treatment with 100 nMMARCKS siRNA or control siRNA.
Figure 19:
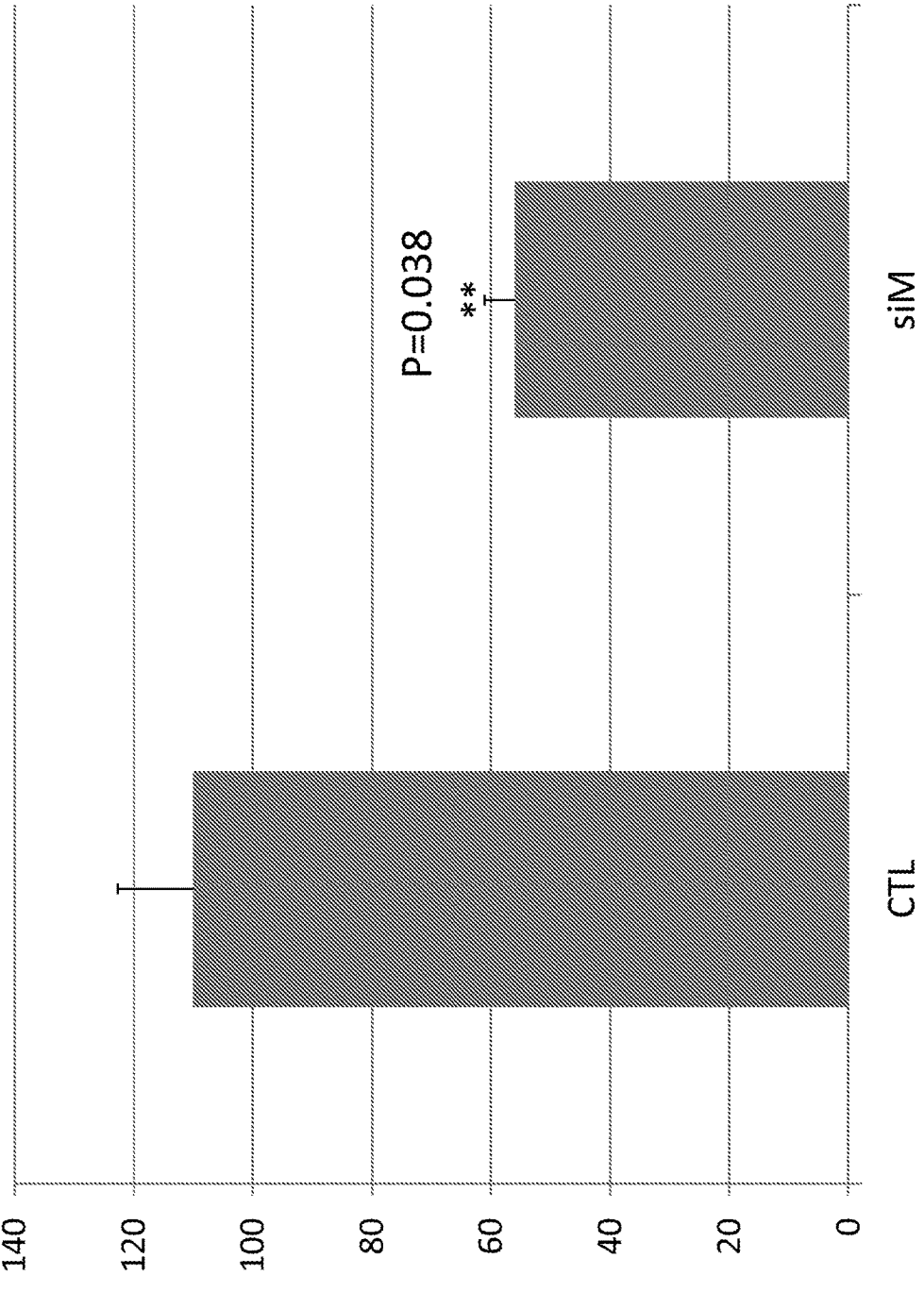
FIG. 19 shows the migration of A549 cancer cells following treatment with 100 nM MARCKS siRNA or control siRNA.

The results of the study are shown in FIGS. 18 and 19. Treatment with MARCKS siRNA significantly inhibited migration of both PC-9 and A549 cells. siRNA knockdown of MARCKS resulted in 90% reduction in cell migration for PC9 cell line (FIG. 18) and resulted in approximately 50% reduction in cell migration for A549 cell line (FIG. 19). Therefore, inhibition of MARCKS expression results in significant reduction in cancer cell migration.

Example 9

MicroRNA21 Inhibition Increases MARCKS and Enhances Cancer Cell Migration

Figure 20:
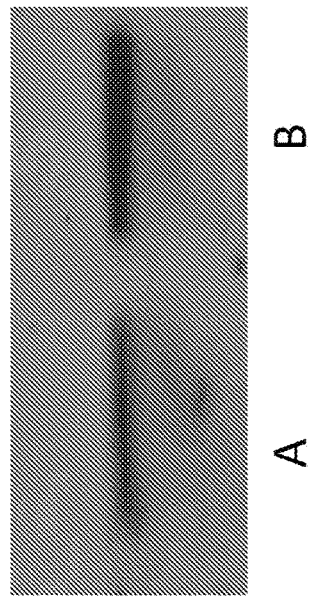
FIG. 20 shows expression of MARCKS in PC9 cells by Western Blot following treatment with 50 nM negative control (HiPerfect vehicle; lane A) or 50 nM miR21 inhibitor (lane B).
Figure 21:
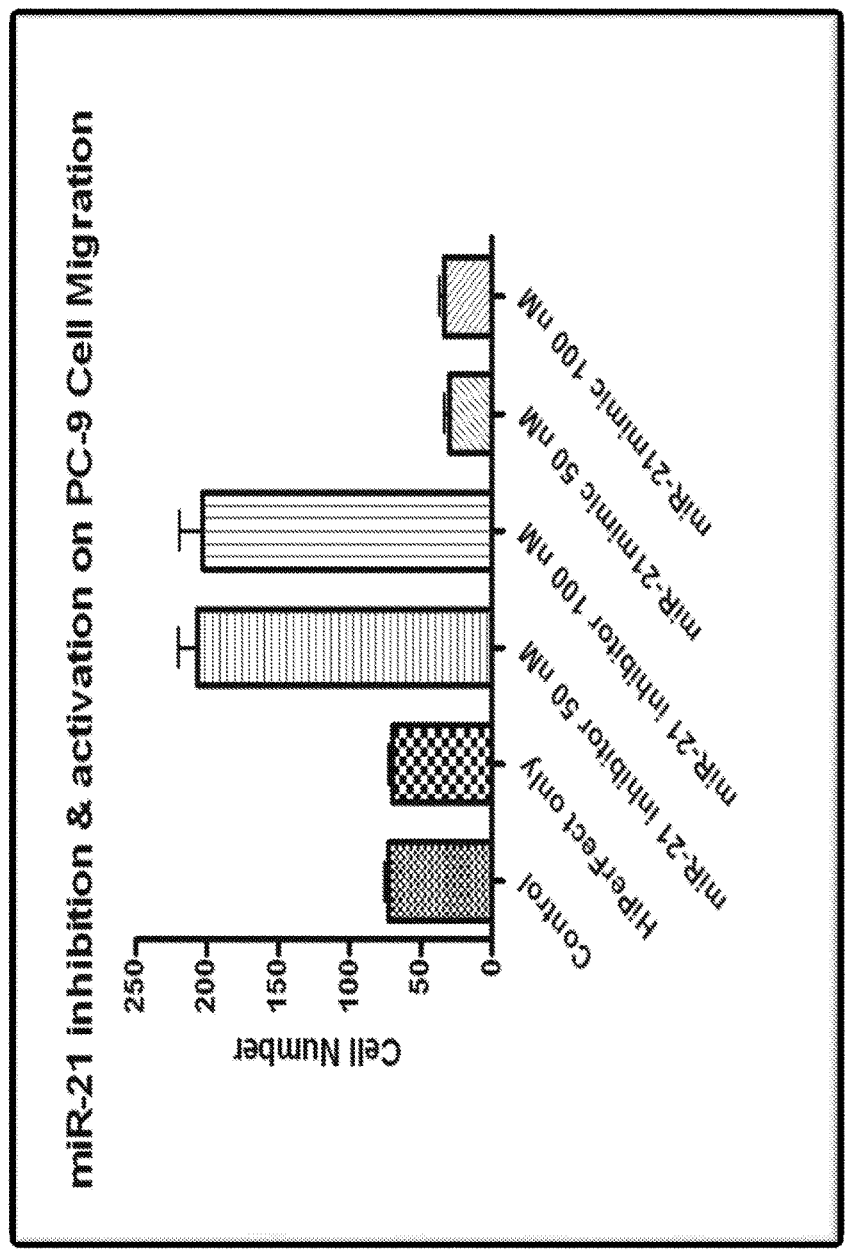
FIG. 21 shows the migration of PC9 cancer cells following miR21 inhibition (50 nM or 100 nM mir-21 inhibitor) or miR21 activation (50 nM or 100 nM miR-21 mimic).

MicroRNA 21 (miR21) regulates levels of MARCKS in cells. In these studies, PC9 human lung cancer cells were transfected with 50 nM or 100 nM of miR21 inhibitor or a mir21 mimic, or a vehicle-only negative control. Levels of MARCKS were measured 48 hours later by Western Blot. Treatment with the miR21 inhibitor (50 nM) increased levels of MARCKS in the cells by ~2.5 fold (FIG. 20). These values correlated with the migration capability of the cells when placed in migration chambers over a 12 hour period. Cells treated with the miR21 inhibitor at 50 or 100 nM showed enhanced migration correlating with increased levels of MARCKS, while cells treated with miR21 mimic showed decreased migration correlating with decreased levels of MARCKS (FIG. 21). Cells treated with HiPerfect vehicle control showed the same level of migration relative to untreated PC9 cells (FIG. 21). The results of the study showed that an increase in MARCKS expression via miR21 inhibition increases cancer cell migration. Moreover, activation of miR21 resulted in decreased migration of PC9 cells.

Taken together, the studies showed that cancer cell migration, and metastasis of cancer cells, can be inhibited by targeting MARCKS using several different means of MARCKS inhibition, including MANS-related peptides and inhibitory microRNAs, i.e., a miR21 mimic.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications cited herein are incorporated herein by reference for the purpose of disclosing and describing specific aspects of the invention for which the publication is cited.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

The invention claimed is:

1. A method for treating cancer in a subject in need thereof, the method comprising administration of a myristoylated alanine-rich C-kinase substrate (MARCKS)-inhibitory compound to the subject, wherein the MARCKS-inhibitory compound is a MARCKS-inhibitory peptide having an amino acid sequence selected from the group consisting of SEQ ID NO: 1 to SEQ ID NO: 231, SEQ ID NO: 234, and SEQ ID NO: 235; wherein the N-terminal and/or C-terminal amino acid of the peptide sequence is optionally chemically modified.

2. The method of claim 1, wherein the method for treating cancer comprises inhibiting metastasis, cancer cell proliferation, tumor growth, or angiogenesis.

3. The method of claim 1, wherein the N-terminal amino acid of the peptide is chemically modified by acylation of the N-terminal amino acid of the peptide in the form of an amide selected from the group consisting of:
   an amide of a $C_2$ (acetyl) to $C_{24}$ aliphatic carboxylic acid which may be linear, branched, saturated, or unsaturated,
   an amide of trifluoroacetic acid,
   an amide of benzoic acid, and
   an amide of a $C_1$ to $C_{24}$ aliphatic alkyl sulfonic acid; or
   the N-terminal amine group of the N-terminal amino acid of the peptide can be alkylated with a group selected from the group consisting of:
   a $C_1$ to $C_{24}$ aliphatic alkyl group,
   linear 2-($C_1$ to $C_{24}$ aliphatic alkyl)oxyethyl group,
   an omega-methoxy-poly(ethyleneoxy)$_n$-ethyl group, where n is from 0 to 10.

4. The method of claim 3, wherein the N-terminal amide is selected from the group consisting of acetyl and myristoyl.

5. The method of claim 1, wherein the administration is by inhalation of a liquid solution or suspension, or by inhalation of a dry powder formulation of the peptide, or by injection of a liquid formulation of the peptide.

6. The method of claim 5, wherein the injection is into a tumor containing the cancer cell or wherein the injection is systemic.

7. The method of claim 6, wherein the tumor is a solid tumor.

8. The method of claim 6, wherein the tumor is a non-solid tumor.

9. The method of claim 1, wherein the C-terminal amino acid of the peptide is chemically modified by amide formation at the C-terminal carboxylic acid group of the C-terminal amino acid of the peptide in the form of an amide selected from the group consisting of:
   an amide of ammonia,
   an amide of a $C_1$ to $C_{24}$ aliphatic alkyl amine,
   an amide of a hydroxyl-substituted $C_2$ to $C_{24}$ aliphatic alkyl amine,
   an amide of a linear 2-($C_1$ to $C_{24}$ aliphatic alkyl)oxyethylamine group, and
   an amide of an omega-methoxy-poly(ethyleneoxy)$_n$-ethylamine group, where n is from 0 to 10.

10. The method of claim 1, wherein the peptide is selected from the group consisting of N-acetyl-GAQFSKTAAK (SEQ ID No: 106); N-myristoyl-AKGE (SEQ ID No: 219); N-myristoyl-GAQFSKTAAK-NH2 (SEQ ID No: 106); N myristoyl-GAQFSKTAAK (SEQ ID No: 106); N-acetyl-GAQFSKTAA (SEQ ID No: 121); N-myristoyl-GAQFSKTAA (SEQ ID No: 121); N-acetyl-GAQFSKTAAK-NH2 (SEQ ID No: 106); and acetyl-GAQFS(d)KTAA(d)K (SEQ ID No. 106).

11. The method of claim 1, wherein the peptide is administered in a dose from between about 0.01 mg/kg/day to about 10 mg/kg/day.

12. The method of claim 1, the method comprising administering a therapeutically effective amount of a peptide selected from the group consisting of N-myristoyl-GAQFSKTAAKGEAAAERPGEAAVA (SEQ ID No: 1); N-myristoyl-GAQFSKTAAKGEAAAERPGEAV (SEQ ID No: 2); N-myristoyl-GAQFSKTAAKGEAAAERPGEAA (SEQ ID No: 4); N-myristoyl-GAQFSKTAAKGEAAAERPGEA (SEQ ID No: 7); N-myristoyl-GAQFSKTAAKGEAAAERPGE (SEQ ID No: 11); N-myristoyl-GAQFSKTAAKGEAAAERPG (SEQ ID No: 16); N-myristoyl-GAQFSKTAAKGEAAAERP (SEQ ID No: 22); N-myristoyl-GAQFSKTAAKGEAAAER (SEQ ID No: 29); N-myristoyl-GAQFSKTAAKGEAAAE (SEQ ID No: 37); N-myristoyl-GAQFSKTAAKGEAAA (SEQ ID No: 46); N-myristoyl-GAQFSKTAAKGEAA (SEQ ID No: 56); N-myristoyl-GAQFSKTAAKGEA (SEQ ID No: 67); N-myristoyl-GAQFSKTAAKGE (SEQ ID No: 79); N-myristoyl-GAQFSKTAAKG (SEQ ID No: 92); N-myristoyl-GAQFSKTAAK (SEQ ID No: 106); N-myristoyl-GAQFSKTAA (SEQ ID No: 121); N-myristoyl-GAQFSKTA (SEQ ID No: 137); N-myristoyl-GAQFSKT (SEQ ID No: 154); N-myristoyl-GAQFSK (SEQ ID No: 172), N-myristoyl-GAQFS (SEQ ID No: 191), N-myristoyl-GAQF (SEQ ID No: 211), N-acetyl-RGAQFSKTAAK (SEQ ID No: 234), N-acetyl-RGAQFSKTAAK-NH2 (SEQ ID No: 234), N-acetyl-RAKGE (SEQ ID NO: 235), and a combination thereof.

* * * * *

SEQUENCE LISTING

```
<160> NUMBER OF SEQ ID NOS: 240

<210> SEQ ID NO 1
<211> LENGTH: 24
<212> TYPE: PRT
<213> ORGANISM: Homo sapiens

<400> SEQUENCE: 1

Gly Ala Gln Phe Ser Lys Thr Ala Ala Lys Gly Glu Ala Ala Ala Glu
1               5                   10                  15

Arg Pro Gly Glu Ala Ala Val Ala
            20

<210> SEQ ID NO 2
<211> LENGTH: 23
<212> TYPE: PRT
<213> ORGANISM: Homo sapiens

<400> SEQUENCE: 2

Gly Ala Gln Phe Ser Lys Thr Ala Ala Lys Gly Glu Ala Ala Ala Glu
1               5                   10                  15

Arg Pro Gly Glu Ala Ala Val
            20

<210> SEQ ID NO 3
<211> LENGTH: 23
<212> TYPE: PRT
<213> ORGANISM: Homo sapiens

<400> SEQUENCE: 3

Ala Gln Phe Ser Lys Thr Ala Ala Lys Gly Glu Ala Ala Ala Glu Arg
1               5                   10                  15

Pro Gly Glu Ala Ala Val Ala
            20

<210> SEQ ID NO 4
<211> LENGTH: 22
<212> TYPE: PRT
<213> ORGANISM: Homo sapiens

<400> SEQUENCE: 4

Gly Ala Gln Phe Ser Lys Thr Ala Ala Lys Gly Glu Ala Ala Ala Glu
1               5                   10                  15

Arg Pro Gly Glu Ala Ala
            20

<210> SEQ ID NO 5
<211> LENGTH: 22
<212> TYPE: PRT
<213> ORGANISM: Homo sapiens

<400> SEQUENCE: 5

Ala Gln Phe Ser Lys Thr Ala Ala Lys Gly Glu Ala Ala Ala Glu Arg
1               5                   10                  15

Pro Gly Glu Ala Ala Val
            20
```

<210> SEQ ID NO 6
<211> LENGTH: 22
<212> TYPE: PRT
<213> ORGANISM: Homo sapiens

<400> SEQUENCE: 6

Gln Phe Ser Lys Thr Ala Ala Lys Gly Glu Ala Ala Ala Glu Arg Pro
1               5                   10                  15

Gly Glu Ala Ala Val Ala
            20

<210> SEQ ID NO 7
<211> LENGTH: 21
<212> TYPE: PRT
<213> ORGANISM: Homo sapiens

<400> SEQUENCE: 7

Gly Ala Gln Phe Ser Lys Thr Ala Ala Lys Gly Glu Ala Ala Ala Glu
1               5                   10                  15

Arg Pro Gly Glu Ala
            20

<210> SEQ ID NO 8
<211> LENGTH: 21
<212> TYPE: PRT
<213> ORGANISM: Homo sapiens

<400> SEQUENCE: 8

Ala Gln Phe Ser Lys Thr Ala Ala Lys Gly Glu Ala Ala Ala Glu Arg
1               5                   10                  15

Pro Gly Glu Ala Ala
            20

<210> SEQ ID NO 9
<211> LENGTH: 21
<212> TYPE: PRT
<213> ORGANISM: Homo sapiens

<400> SEQUENCE: 9

Gln Phe Ser Lys Thr Ala Ala Lys Gly Glu Ala Ala Ala Glu Arg Pro
1               5                   10                  15

Gly Glu Ala Ala Val
            20

<210> SEQ ID NO 10
<211> LENGTH: 21
<212> TYPE: PRT
<213> ORGANISM: Homo sapiens

<400> SEQUENCE: 10

Phe Ser Lys Thr Ala Ala Lys Gly Glu Ala Ala Ala Glu Arg Pro Gly
1               5                   10                  15

Glu Ala Ala Val Ala
            20

<210> SEQ ID NO 11
<211> LENGTH: 20
<212> TYPE: PRT
<213> ORGANISM: Homo sapiens

<400> SEQUENCE: 11

```
Gly Ala Gln Phe Ser Lys Thr Ala Ala Lys Gly Glu Ala Ala Ala Glu
1               5                   10                  15

Arg Pro Gly Glu
            20

<210> SEQ ID NO 12
<211> LENGTH: 20
<212> TYPE: PRT
<213> ORGANISM: Homo sapiens

<400> SEQUENCE: 12

Ala Gln Phe Ser Lys Thr Ala Ala Lys Gly Glu Ala Ala Ala Glu Arg
1               5                   10                  15

Pro Gly Glu Ala
            20

<210> SEQ ID NO 13
<211> LENGTH: 20
<212> TYPE: PRT
<213> ORGANISM: Homo sapiens

<400> SEQUENCE: 13

Gln Phe Ser Lys Thr Ala Ala Lys Gly Glu Ala Ala Ala Glu Arg Pro
1               5                   10                  15

Gly Glu Ala Ala
            20

<210> SEQ ID NO 14
<211> LENGTH: 20
<212> TYPE: PRT
<213> ORGANISM: Homo sapiens

<400> SEQUENCE: 14

Phe Ser Lys Thr Ala Ala Lys Gly Glu Ala Ala Ala Glu Arg Pro Gly
1               5                   10                  15

Glu Ala Ala Val
            20

<210> SEQ ID NO 15
<211> LENGTH: 20
<212> TYPE: PRT
<213> ORGANISM: Homo sapiens

<400> SEQUENCE: 15

Ser Lys Thr Ala Ala Lys Gly Glu Ala Ala Ala Glu Arg Pro Gly Glu
1               5                   10                  15

Ala Ala Val Ala
            20

<210> SEQ ID NO 16
<211> LENGTH: 19
<212> TYPE: PRT
<213> ORGANISM: Homo sapiens

<400> SEQUENCE: 16

Gly Ala Gln Phe Ser Lys Thr Ala Ala Lys Gly Glu Ala Ala Ala Glu
1               5                   10                  15

Arg Pro Gly

<210> SEQ ID NO 17
<211> LENGTH: 19
<212> TYPE: PRT
```

```
<213> ORGANISM: Homo sapiens

<400> SEQUENCE: 17

Ala Gln Phe Ser Lys Thr Ala Ala Lys Gly Glu Ala Ala Ala Glu Arg
1               5                   10                  15

Pro Gly Glu

<210> SEQ ID NO 18
<211> LENGTH: 19
<212> TYPE: PRT
<213> ORGANISM: Homo sapiens

<400> SEQUENCE: 18

Gln Phe Ser Lys Thr Ala Ala Lys Gly Glu Ala Ala Ala Glu Arg Pro
1               5                   10                  15

Gly Glu Ala

<210> SEQ ID NO 19
<211> LENGTH: 19
<212> TYPE: PRT
<213> ORGANISM: Homo sapiens

<400> SEQUENCE: 19

Phe Ser Lys Thr Ala Ala Lys Gly Glu Ala Ala Ala Glu Arg Pro Gly
1               5                   10                  15

Glu Ala Ala

<210> SEQ ID NO 20
<211> LENGTH: 19
<212> TYPE: PRT
<213> ORGANISM: Homo sapiens

<400> SEQUENCE: 20

Ser Lys Thr Ala Ala Lys Gly Glu Ala Ala Ala Glu Arg Pro Gly Glu
1               5                   10                  15

Ala Ala Val

<210> SEQ ID NO 21
<211> LENGTH: 19
<212> TYPE: PRT
<213> ORGANISM: Homo sapiens

<400> SEQUENCE: 21

Lys Thr Ala Ala Lys Gly Glu Ala Ala Ala Glu Arg Pro Gly Glu Ala
1               5                   10                  15

Ala Val Ala

<210> SEQ ID NO 22
<211> LENGTH: 18
<212> TYPE: PRT
<213> ORGANISM: Homo sapiens

<400> SEQUENCE: 22

Gly Ala Gln Phe Ser Lys Thr Ala Ala Lys Gly Glu Ala Ala Ala Glu
1               5                   10                  15

Arg Pro

<210> SEQ ID NO 23
<211> LENGTH: 18
<212> TYPE: PRT
<213> ORGANISM: Homo sapiens
```

<400> SEQUENCE: 23

Ala Gln Phe Ser Lys Thr Ala Ala Lys Gly Glu Ala Ala Ala Glu Arg
1               5                   10                  15

Pro Gly

<210> SEQ ID NO 24
<211> LENGTH: 18
<212> TYPE: PRT
<213> ORGANISM: Homo sapiens

<400> SEQUENCE: 24

Gln Phe Ser Lys Thr Ala Ala Lys Gly Glu Ala Ala Ala Glu Arg Pro
1               5                   10                  15

Gly Glu

<210> SEQ ID NO 25
<211> LENGTH: 18
<212> TYPE: PRT
<213> ORGANISM: Homo sapiens

<400> SEQUENCE: 25

Phe Ser Lys Thr Ala Ala Lys Gly Glu Ala Ala Ala Glu Arg Pro Gly
1               5                   10                  15

Glu Ala

<210> SEQ ID NO 26
<211> LENGTH: 18
<212> TYPE: PRT
<213> ORGANISM: Homo sapiens

<400> SEQUENCE: 26

Ser Lys Thr Ala Ala Lys Gly Glu Ala Ala Ala Glu Arg Pro Gly Glu
1               5                   10                  15

Ala Ala

<210> SEQ ID NO 27
<211> LENGTH: 18
<212> TYPE: PRT
<213> ORGANISM: Homo sapiens

<400> SEQUENCE: 27

Lys Thr Ala Ala Lys Gly Glu Ala Ala Ala Glu Arg Pro Gly Glu Ala
1               5                   10                  15

Ala Val

<210> SEQ ID NO 28
<211> LENGTH: 18
<212> TYPE: PRT
<213> ORGANISM: Homo sapiens

<400> SEQUENCE: 28

Thr Ala Ala Lys Gly Glu Ala Ala Ala Glu Arg Pro Gly Glu Ala Ala
1               5                   10                  15

Val Ala

<210> SEQ ID NO 29
<211> LENGTH: 17
<212> TYPE: PRT
<213> ORGANISM: Homo sapiens

```
<400> SEQUENCE: 29

Gly Ala Gln Phe Ser Lys Thr Ala Ala Lys Gly Glu Ala Ala Ala Glu
1               5                   10                  15

Arg

<210> SEQ ID NO 30
<211> LENGTH: 17
<212> TYPE: PRT
<213> ORGANISM: Homo sapiens

<400> SEQUENCE: 30

Ala Gln Phe Ser Lys Thr Ala Ala Lys Gly Glu Ala Ala Ala Glu Arg
1               5                   10                  15

Pro

<210> SEQ ID NO 31
<211> LENGTH: 17
<212> TYPE: PRT
<213> ORGANISM: Homo sapiens

<400> SEQUENCE: 31

Gln Phe Ser Lys Thr Ala Ala Lys Gly Glu Ala Ala Ala Glu Arg Pro
1               5                   10                  15

Gly

<210> SEQ ID NO 32
<211> LENGTH: 17
<212> TYPE: PRT
<213> ORGANISM: Homo sapiens

<400> SEQUENCE: 32

Phe Ser Lys Thr Ala Ala Lys Gly Glu Ala Ala Ala Glu Arg Pro Gly
1               5                   10                  15

Glu

<210> SEQ ID NO 33
<211> LENGTH: 17
<212> TYPE: PRT
<213> ORGANISM: Homo sapiens

<400> SEQUENCE: 33

Ser Lys Thr Ala Ala Lys Gly Glu Ala Ala Ala Glu Arg Pro Gly Glu
1               5                   10                  15

Ala

<210> SEQ ID NO 34
<211> LENGTH: 17
<212> TYPE: PRT
<213> ORGANISM: Homo sapiens

<400> SEQUENCE: 34

Lys Thr Ala Ala Lys Gly Glu Ala Ala Ala Glu Arg Pro Gly Glu Ala
1               5                   10                  15

Ala

<210> SEQ ID NO 35
<211> LENGTH: 17
<212> TYPE: PRT
<213> ORGANISM: Homo sapiens

<400> SEQUENCE: 35
```

```
Thr Ala Ala Lys Gly Glu Ala Ala Ala Glu Arg Pro Gly Glu Ala Ala
1               5                   10                  15

Val

<210> SEQ ID NO 36
<211> LENGTH: 17
<212> TYPE: PRT
<213> ORGANISM: Homo sapiens

<400> SEQUENCE: 36

Ala Ala Lys Gly Glu Ala Ala Ala Glu Arg Pro Gly Glu Ala Ala Val
1               5                   10                  15

Ala

<210> SEQ ID NO 37
<211> LENGTH: 16
<212> TYPE: PRT
<213> ORGANISM: Homo sapiens

<400> SEQUENCE: 37

Gly Ala Gln Phe Ser Lys Thr Ala Ala Lys Gly Glu Ala Ala Ala Glu
1               5                   10                  15

<210> SEQ ID NO 38
<211> LENGTH: 16
<212> TYPE: PRT
<213> ORGANISM: Homo sapiens

<400> SEQUENCE: 38

Ala Gln Phe Ser Lys Thr Ala Ala Lys Gly Glu Ala Ala Ala Glu Arg
1               5                   10                  15

<210> SEQ ID NO 39
<211> LENGTH: 16
<212> TYPE: PRT
<213> ORGANISM: Homo sapiens

<400> SEQUENCE: 39

Gln Phe Ser Lys Thr Ala Ala Lys Gly Glu Ala Ala Ala Glu Arg Pro
1               5                   10                  15

<210> SEQ ID NO 40
<211> LENGTH: 16
<212> TYPE: PRT
<213> ORGANISM: Homo sapiens

<400> SEQUENCE: 40

Phe Ser Lys Thr Ala Ala Lys Gly Glu Ala Ala Ala Glu Arg Pro Gly
1               5                   10                  15

<210> SEQ ID NO 41
<211> LENGTH: 16
<212> TYPE: PRT
<213> ORGANISM: Homo sapiens

<400> SEQUENCE: 41

Ser Lys Thr Ala Ala Lys Gly Glu Ala Ala Ala Glu Arg Pro Gly Glu
1               5                   10                  15

<210> SEQ ID NO 42
<211> LENGTH: 16
<212> TYPE: PRT
<213> ORGANISM: Homo sapiens
```

<400> SEQUENCE: 42

Lys Thr Ala Ala Lys Gly Glu Ala Ala Ala Glu Arg Pro Gly Glu Ala
1               5                   10                  15

<210> SEQ ID NO 43
<211> LENGTH: 16
<212> TYPE: PRT
<213> ORGANISM: Homo sapiens

<400> SEQUENCE: 43

Thr Ala Ala Lys Gly Glu Ala Ala Ala Glu Arg Pro Gly Glu Ala Ala
1               5                   10                  15

<210> SEQ ID NO 44
<211> LENGTH: 16
<212> TYPE: PRT
<213> ORGANISM: Homo sapiens

<400> SEQUENCE: 44

Ala Ala Lys Gly Glu Ala Ala Ala Glu Arg Pro Gly Glu Ala Ala Val
1               5                   10                  15

<210> SEQ ID NO 45
<211> LENGTH: 16
<212> TYPE: PRT
<213> ORGANISM: Homo sapiens

<400> SEQUENCE: 45

Ala Lys Gly Glu Ala Ala Ala Glu Arg Pro Gly Glu Ala Ala Val Ala
1               5                   10                  15

<210> SEQ ID NO 46
<211> LENGTH: 15
<212> TYPE: PRT
<213> ORGANISM: Homo sapiens

<400> SEQUENCE: 46

Gly Ala Gln Phe Ser Lys Thr Ala Ala Lys Gly Glu Ala Ala Ala
1               5                   10                  15

<210> SEQ ID NO 47
<211> LENGTH: 15
<212> TYPE: PRT
<213> ORGANISM: Homo sapiens

<400> SEQUENCE: 47

Ala Gln Phe Ser Lys Thr Ala Ala Lys Gly Glu Ala Ala Ala Glu
1               5                   10                  15

<210> SEQ ID NO 48
<211> LENGTH: 15
<212> TYPE: PRT
<213> ORGANISM: Homo sapiens

<400> SEQUENCE: 48

Gln Phe Ser Lys Thr Ala Ala Lys Gly Glu Ala Ala Ala Glu Arg
1               5                   10                  15

<210> SEQ ID NO 49
<211> LENGTH: 15
<212> TYPE: PRT
<213> ORGANISM: Homo sapiens

<400> SEQUENCE: 49

Phe Ser Lys Thr Ala Ala Lys Gly Glu Ala Ala Ala Glu Arg Pro
1               5                   10                  15

<210> SEQ ID NO 50
<211> LENGTH: 15
<212> TYPE: PRT
<213> ORGANISM: Homo sapiens

<400> SEQUENCE: 50

Ser Lys Thr Ala Ala Lys Gly Glu Ala Ala Ala Glu Arg Pro Gly
1               5                   10                  15

<210> SEQ ID NO 51
<211> LENGTH: 15
<212> TYPE: PRT
<213> ORGANISM: Homo sapiens

<400> SEQUENCE: 51

Lys Thr Ala Ala Lys Gly Glu Ala Ala Ala Glu Arg Pro Gly Glu
1               5                   10                  15

<210> SEQ ID NO 52
<211> LENGTH: 15
<212> TYPE: PRT
<213> ORGANISM: Homo sapiens

<400> SEQUENCE: 52

Thr Ala Ala Lys Gly Glu Ala Ala Ala Glu Arg Pro Gly Glu Ala
1               5                   10                  15

<210> SEQ ID NO 53
<211> LENGTH: 15
<212> TYPE: PRT
<213> ORGANISM: Homo sapiens

<400> SEQUENCE: 53

Ala Ala Lys Gly Glu Ala Ala Ala Glu Arg Pro Gly Glu Ala Ala
1               5                   10                  15

<210> SEQ ID NO 54
<211> LENGTH: 15
<212> TYPE: PRT
<213> ORGANISM: Homo sapiens

<400> SEQUENCE: 54

Ala Lys Gly Glu Ala Ala Ala Glu Arg Pro Gly Glu Ala Ala Val
1               5                   10                  15

<210> SEQ ID NO 55
<211> LENGTH: 15
<212> TYPE: PRT
<213> ORGANISM: Homo sapiens

<400> SEQUENCE: 55

Lys Gly Glu Ala Ala Ala Glu Arg Pro Gly Glu Ala Ala Val Ala
1               5                   10                  15

<210> SEQ ID NO 56
<211> LENGTH: 14
<212> TYPE: PRT
<213> ORGANISM: Homo sapiens

<400> SEQUENCE: 56

Gly Ala Gln Phe Ser Lys Thr Ala Ala Lys Gly Glu Ala Ala

```
1               5                   10
```

<210> SEQ ID NO 57
<211> LENGTH: 14
<212> TYPE: PRT
<213> ORGANISM: Homo sapiens

<400> SEQUENCE: 57

```
Ala Gln Phe Ser Lys Thr Ala Ala Lys Gly Glu Ala Ala Ala
1               5                   10
```

<210> SEQ ID NO 58
<211> LENGTH: 14
<212> TYPE: PRT
<213> ORGANISM: Homo sapiens

<400> SEQUENCE: 58

```
Gln Phe Ser Lys Thr Ala Ala Lys Gly Glu Ala Ala Ala Glu
1               5                   10
```

<210> SEQ ID NO 59
<211> LENGTH: 14
<212> TYPE: PRT
<213> ORGANISM: Homo sapiens

<400> SEQUENCE: 59

```
Phe Ser Lys Thr Ala Ala Lys Gly Glu Ala Ala Ala Glu Arg
1               5                   10
```

<210> SEQ ID NO 60
<211> LENGTH: 14
<212> TYPE: PRT
<213> ORGANISM: Homo sapiens

<400> SEQUENCE: 60

```
Ser Lys Thr Ala Ala Lys Gly Glu Ala Ala Ala Glu Arg Pro
1               5                   10
```

<210> SEQ ID NO 61
<211> LENGTH: 14
<212> TYPE: PRT
<213> ORGANISM: Homo sapiens

<400> SEQUENCE: 61

```
Lys Thr Ala Ala Lys Gly Glu Ala Ala Ala Glu Arg Pro Gly
1               5                   10
```

<210> SEQ ID NO 62
<211> LENGTH: 14
<212> TYPE: PRT
<213> ORGANISM: Homo sapiens

<400> SEQUENCE: 62

```
Thr Ala Ala Lys Gly Glu Ala Ala Ala Glu Arg Pro Gly Glu
1               5                   10
```

<210> SEQ ID NO 63
<211> LENGTH: 14
<212> TYPE: PRT
<213> ORGANISM: Homo sapiens

<400> SEQUENCE: 63

```
Ala Ala Lys Gly Glu Ala Ala Ala Glu Arg Pro Gly Glu Ala
1               5                   10
```

<210> SEQ ID NO 64
<211> LENGTH: 14
<212> TYPE: PRT
<213> ORGANISM: Homo sapiens

<400> SEQUENCE: 64

Ala Lys Gly Glu Ala Ala Ala Glu Arg Pro Gly Glu Ala Ala
1               5                   10

<210> SEQ ID NO 65
<211> LENGTH: 14
<212> TYPE: PRT
<213> ORGANISM: Homo sapiens

<400> SEQUENCE: 65

Lys Gly Glu Ala Ala Ala Glu Arg Pro Gly Glu Ala Ala Val
1               5                   10

<210> SEQ ID NO 66
<211> LENGTH: 14
<212> TYPE: PRT
<213> ORGANISM: Homo sapiens

<400> SEQUENCE: 66

Gly Glu Ala Ala Ala Glu Arg Pro Gly Glu Ala Ala Val Ala
1               5                   10

<210> SEQ ID NO 67
<211> LENGTH: 13
<212> TYPE: PRT
<213> ORGANISM: Homo sapiens

<400> SEQUENCE: 67

Gly Ala Gln Phe Ser Lys Thr Ala Ala Lys Gly Glu Ala
1               5                   10

<210> SEQ ID NO 68
<211> LENGTH: 13
<212> TYPE: PRT
<213> ORGANISM: Homo sapiens

<400> SEQUENCE: 68

Ala Gln Phe Ser Lys Thr Ala Ala Lys Gly Glu Ala Ala
1               5                   10

<210> SEQ ID NO 69
<211> LENGTH: 13
<212> TYPE: PRT
<213> ORGANISM: Homo sapiens

<400> SEQUENCE: 69

Gln Phe Ser Lys Thr Ala Ala Lys Gly Glu Ala Ala Ala
1               5                   10

<210> SEQ ID NO 70
<211> LENGTH: 13
<212> TYPE: PRT
<213> ORGANISM: Homo sapiens

<400> SEQUENCE: 70

Phe Ser Lys Thr Ala Ala Lys Gly Glu Ala Ala Ala Glu
1               5                   10

<210> SEQ ID NO 71

```
<211> LENGTH: 13
<212> TYPE: PRT
<213> ORGANISM: Homo sapiens

<400> SEQUENCE: 71

Ser Lys Thr Ala Ala Lys Gly Glu Ala Ala Ala Glu Arg
1               5                   10

<210> SEQ ID NO 72
<211> LENGTH: 13
<212> TYPE: PRT
<213> ORGANISM: Homo sapiens

<400> SEQUENCE: 72

Lys Thr Ala Ala Lys Gly Glu Ala Ala Ala Glu Arg Pro
1               5                   10

<210> SEQ ID NO 73
<211> LENGTH: 13
<212> TYPE: PRT
<213> ORGANISM: Homo sapiens

<400> SEQUENCE: 73

Thr Ala Ala Lys Gly Glu Ala Ala Ala Glu Arg Pro Gly
1               5                   10

<210> SEQ ID NO 74
<211> LENGTH: 13
<212> TYPE: PRT
<213> ORGANISM: Homo sapiens

<400> SEQUENCE: 74

Ala Ala Lys Gly Glu Ala Ala Ala Glu Arg Pro Gly Glu
1               5                   10

<210> SEQ ID NO 75
<211> LENGTH: 13
<212> TYPE: PRT
<213> ORGANISM: Homo sapiens

<400> SEQUENCE: 75

Ala Lys Gly Glu Ala Ala Ala Glu Arg Pro Gly Glu Ala
1               5                   10

<210> SEQ ID NO 76
<211> LENGTH: 13
<212> TYPE: PRT
<213> ORGANISM: Homo sapiens

<400> SEQUENCE: 76

Lys Gly Glu Ala Ala Ala Glu Arg Pro Gly Glu Ala Ala
1               5                   10

<210> SEQ ID NO 77
<211> LENGTH: 13
<212> TYPE: PRT
<213> ORGANISM: Homo sapiens

<400> SEQUENCE: 77

Gly Glu Ala Ala Ala Glu Arg Pro Gly Glu Ala Ala Val
1               5                   10

<210> SEQ ID NO 78
<211> LENGTH: 13
<212> TYPE: PRT
```

<213> ORGANISM: Homo sapiens

<400> SEQUENCE: 78

Glu Ala Ala Glu Arg Pro Gly Glu Ala Ala Val Ala
1               5                   10

<210> SEQ ID NO 79
<211> LENGTH: 12
<212> TYPE: PRT
<213> ORGANISM: Homo sapiens

<400> SEQUENCE: 79

Gly Ala Gln Phe Ser Lys Thr Ala Ala Lys Gly Glu
1               5                   10

<210> SEQ ID NO 80
<211> LENGTH: 12
<212> TYPE: PRT
<213> ORGANISM: Homo sapiens

<400> SEQUENCE: 80

Ala Gln Phe Ser Lys Thr Ala Ala Lys Gly Glu Ala
1               5                   10

<210> SEQ ID NO 81
<211> LENGTH: 12
<212> TYPE: PRT
<213> ORGANISM: Homo sapiens

<400> SEQUENCE: 81

Gln Phe Ser Lys Thr Ala Ala Lys Gly Glu Ala Ala
1               5                   10

<210> SEQ ID NO 82
<211> LENGTH: 12
<212> TYPE: PRT
<213> ORGANISM: Homo sapiens

<400> SEQUENCE: 82

Phe Ser Lys Thr Ala Ala Lys Gly Glu Ala Ala Ala
1               5                   10

<210> SEQ ID NO 83
<211> LENGTH: 12
<212> TYPE: PRT
<213> ORGANISM: Homo sapiens

<400> SEQUENCE: 83

Ser Lys Thr Ala Ala Lys Gly Glu Ala Ala Ala Glu
1               5                   10

<210> SEQ ID NO 84
<211> LENGTH: 12
<212> TYPE: PRT
<213> ORGANISM: Homo sapiens

<400> SEQUENCE: 84

Lys Thr Ala Ala Lys Gly Glu Ala Ala Ala Glu Arg
1               5                   10

<210> SEQ ID NO 85
<211> LENGTH: 12
<212> TYPE: PRT
<213> ORGANISM: Homo sapiens

```
<400> SEQUENCE: 85

Thr Ala Ala Lys Gly Glu Ala Ala Ala Glu Arg Pro
1               5                   10

<210> SEQ ID NO 86
<211> LENGTH: 12
<212> TYPE: PRT
<213> ORGANISM: Homo sapiens

<400> SEQUENCE: 86

Ala Ala Lys Gly Glu Ala Ala Ala Glu Arg Pro Gly
1               5                   10

<210> SEQ ID NO 87
<211> LENGTH: 12
<212> TYPE: PRT
<213> ORGANISM: Homo sapiens

<400> SEQUENCE: 87

Ala Lys Gly Glu Ala Ala Ala Glu Arg Pro Gly Glu
1               5                   10

<210> SEQ ID NO 88
<211> LENGTH: 12
<212> TYPE: PRT
<213> ORGANISM: Homo sapiens

<400> SEQUENCE: 88

Lys Gly Glu Ala Ala Ala Glu Arg Pro Gly Glu Ala
1               5                   10

<210> SEQ ID NO 89
<211> LENGTH: 12
<212> TYPE: PRT
<213> ORGANISM: Homo sapiens

<400> SEQUENCE: 89

Gly Glu Ala Ala Ala Glu Arg Pro Gly Glu Ala Ala
1               5                   10

<210> SEQ ID NO 90
<211> LENGTH: 12
<212> TYPE: PRT
<213> ORGANISM: Homo sapiens

<400> SEQUENCE: 90

Glu Ala Ala Ala Glu Arg Pro Gly Glu Ala Ala Val
1               5                   10

<210> SEQ ID NO 91
<211> LENGTH: 12
<212> TYPE: PRT
<213> ORGANISM: Homo sapiens

<400> SEQUENCE: 91

Ala Ala Ala Glu Arg Pro Gly Glu Ala Ala Val Ala
1               5                   10

<210> SEQ ID NO 92
<211> LENGTH: 11
<212> TYPE: PRT
<213> ORGANISM: Homo sapiens

<400> SEQUENCE: 92
```

Gly Ala Gln Phe Ser Lys Thr Ala Ala Lys Gly
1               5                   10

<210> SEQ ID NO 93
<211> LENGTH: 11
<212> TYPE: PRT
<213> ORGANISM: Homo sapiens

<400> SEQUENCE: 93

Ala Gln Phe Ser Lys Thr Ala Ala Lys Gly Glu
1               5                   10

<210> SEQ ID NO 94
<211> LENGTH: 11
<212> TYPE: PRT
<213> ORGANISM: Homo sapiens

<400> SEQUENCE: 94

Gln Phe Ser Lys Thr Ala Ala Lys Gly Glu Ala
1               5                   10

<210> SEQ ID NO 95
<211> LENGTH: 11
<212> TYPE: PRT
<213> ORGANISM: Homo sapiens

<400> SEQUENCE: 95

Phe Ser Lys Thr Ala Ala Lys Gly Glu Ala Ala
1               5                   10

<210> SEQ ID NO 96
<211> LENGTH: 11
<212> TYPE: PRT
<213> ORGANISM: Homo sapiens

<400> SEQUENCE: 96

Ser Lys Thr Ala Ala Lys Gly Glu Ala Ala Ala
1               5                   10

<210> SEQ ID NO 97
<211> LENGTH: 11
<212> TYPE: PRT
<213> ORGANISM: Homo sapiens

<400> SEQUENCE: 97

Lys Thr Ala Ala Lys Gly Glu Ala Ala Ala Glu
1               5                   10

<210> SEQ ID NO 98
<211> LENGTH: 11
<212> TYPE: PRT
<213> ORGANISM: Homo sapiens

<400> SEQUENCE: 98

Thr Ala Ala Lys Gly Glu Ala Ala Ala Glu Arg
1               5                   10

<210> SEQ ID NO 99
<211> LENGTH: 11
<212> TYPE: PRT
<213> ORGANISM: Homo sapiens

<400> SEQUENCE: 99

Ala Ala Lys Gly Glu Ala Ala Ala Glu Arg Pro
1               5                   10

```
<210> SEQ ID NO 100
<211> LENGTH: 11
<212> TYPE: PRT
<213> ORGANISM: Homo sapiens

<400> SEQUENCE: 100

Ala Lys Gly Glu Ala Ala Ala Glu Arg Pro Gly
1               5                   10

<210> SEQ ID NO 101
<211> LENGTH: 11
<212> TYPE: PRT
<213> ORGANISM: Homo sapiens

<400> SEQUENCE: 101

Lys Gly Glu Ala Ala Ala Glu Arg Pro Gly Glu
1               5                   10

<210> SEQ ID NO 102
<211> LENGTH: 11
<212> TYPE: PRT
<213> ORGANISM: Homo sapiens

<400> SEQUENCE: 102

Gly Glu Ala Ala Ala Glu Arg Pro Gly Glu Ala
1               5                   10

<210> SEQ ID NO 103
<211> LENGTH: 11
<212> TYPE: PRT
<213> ORGANISM: Homo sapiens

<400> SEQUENCE: 103

Glu Ala Ala Ala Glu Arg Pro Gly Glu Ala Ala
1               5                   10

<210> SEQ ID NO 104
<211> LENGTH: 11
<212> TYPE: PRT
<213> ORGANISM: Homo sapiens

<400> SEQUENCE: 104

Ala Ala Ala Glu Arg Pro Gly Glu Ala Ala Val
1               5                   10

<210> SEQ ID NO 105
<211> LENGTH: 11
<212> TYPE: PRT
<213> ORGANISM: Homo sapiens

<400> SEQUENCE: 105

Ala Ala Glu Arg Pro Gly Glu Ala Ala Val Ala
1               5                   10

<210> SEQ ID NO 106
<211> LENGTH: 10
<212> TYPE: PRT
<213> ORGANISM: Homo sapiens

<400> SEQUENCE: 106

Gly Ala Gln Phe Ser Lys Thr Ala Ala Lys
1               5                   10
```

```
<210> SEQ ID NO 107
<211> LENGTH: 10
<212> TYPE: PRT
<213> ORGANISM: Homo sapiens

<400> SEQUENCE: 107

Ala Gln Phe Ser Lys Thr Ala Ala Lys Gly
1               5                   10

<210> SEQ ID NO 108
<211> LENGTH: 10
<212> TYPE: PRT
<213> ORGANISM: Homo sapiens

<400> SEQUENCE: 108

Gln Phe Ser Lys Thr Ala Ala Lys Gly Glu
1               5                   10

<210> SEQ ID NO 109
<211> LENGTH: 10
<212> TYPE: PRT
<213> ORGANISM: Homo sapiens

<400> SEQUENCE: 109

Phe Ser Lys Thr Ala Ala Lys Gly Glu Ala
1               5                   10

<210> SEQ ID NO 110
<211> LENGTH: 10
<212> TYPE: PRT
<213> ORGANISM: Homo sapiens

<400> SEQUENCE: 110

Ser Lys Thr Ala Ala Lys Gly Glu Ala Ala
1               5                   10

<210> SEQ ID NO 111
<211> LENGTH: 10
<212> TYPE: PRT
<213> ORGANISM: Homo sapiens

<400> SEQUENCE: 111

Lys Thr Ala Ala Lys Gly Glu Ala Ala Ala
1               5                   10

<210> SEQ ID NO 112
<211> LENGTH: 10
<212> TYPE: PRT
<213> ORGANISM: Homo sapiens

<400> SEQUENCE: 112

Thr Ala Ala Lys Gly Glu Ala Ala Ala Glu
1               5                   10

<210> SEQ ID NO 113
<211> LENGTH: 10
<212> TYPE: PRT
<213> ORGANISM: Homo sapiens

<400> SEQUENCE: 113

Ala Ala Lys Gly Glu Ala Ala Ala Glu Arg
1               5                   10

<210> SEQ ID NO 114
<211> LENGTH: 10
```

```
<212> TYPE: PRT
<213> ORGANISM: Homo sapiens

<400> SEQUENCE: 114

Ala Lys Gly Glu Ala Ala Ala Glu Arg Pro
1               5                   10

<210> SEQ ID NO 115
<211> LENGTH: 10
<212> TYPE: PRT
<213> ORGANISM: Homo sapiens

<400> SEQUENCE: 115

Lys Gly Glu Ala Ala Ala Glu Arg Pro Gly
1               5                   10

<210> SEQ ID NO 116
<211> LENGTH: 10
<212> TYPE: PRT
<213> ORGANISM: Homo sapiens

<400> SEQUENCE: 116

Gly Glu Ala Ala Ala Glu Arg Pro Gly Glu
1               5                   10

<210> SEQ ID NO 117
<211> LENGTH: 10
<212> TYPE: PRT
<213> ORGANISM: Homo sapiens

<400> SEQUENCE: 117

Glu Ala Ala Ala Glu Arg Pro Gly Glu Ala
1               5                   10

<210> SEQ ID NO 118
<211> LENGTH: 10
<212> TYPE: PRT
<213> ORGANISM: Homo sapiens

<400> SEQUENCE: 118

Ala Ala Ala Glu Arg Pro Gly Glu Ala Ala
1               5                   10

<210> SEQ ID NO 119
<211> LENGTH: 10
<212> TYPE: PRT
<213> ORGANISM: Homo sapiens

<400> SEQUENCE: 119

Ala Ala Glu Arg Pro Gly Glu Ala Ala Val
1               5                   10

<210> SEQ ID NO 120
<211> LENGTH: 10
<212> TYPE: PRT
<213> ORGANISM: Homo sapiens

<400> SEQUENCE: 120

Ala Glu Arg Pro Gly Glu Ala Ala Val Ala
1               5                   10

<210> SEQ ID NO 121
<211> LENGTH: 9
<212> TYPE: PRT
<213> ORGANISM: Homo sapiens
```

<400> SEQUENCE: 121

Gly Ala Gln Phe Ser Lys Thr Ala Ala
1               5

<210> SEQ ID NO 122
<211> LENGTH: 9
<212> TYPE: PRT
<213> ORGANISM: Homo sapiens

<400> SEQUENCE: 122

Ala Gln Phe Ser Lys Thr Ala Ala Lys
1               5

<210> SEQ ID NO 123
<211> LENGTH: 9
<212> TYPE: PRT
<213> ORGANISM: Homo sapiens

<400> SEQUENCE: 123

Gln Phe Ser Lys Thr Ala Ala Lys Gly
1               5

<210> SEQ ID NO 124
<211> LENGTH: 9
<212> TYPE: PRT
<213> ORGANISM: Homo sapiens

<400> SEQUENCE: 124

Phe Ser Lys Thr Ala Ala Lys Gly Glu
1               5

<210> SEQ ID NO 125
<211> LENGTH: 9
<212> TYPE: PRT
<213> ORGANISM: Homo sapiens

<400> SEQUENCE: 125

Ser Lys Thr Ala Ala Lys Gly Glu Ala
1               5

<210> SEQ ID NO 126
<211> LENGTH: 9
<212> TYPE: PRT
<213> ORGANISM: Homo sapiens

<400> SEQUENCE: 126

Lys Thr Ala Ala Lys Gly Glu Ala Ala
1               5

<210> SEQ ID NO 127
<211> LENGTH: 9
<212> TYPE: PRT
<213> ORGANISM: Homo sapiens

<400> SEQUENCE: 127

Thr Ala Ala Lys Gly Glu Ala Ala Ala
1               5

<210> SEQ ID NO 128
<211> LENGTH: 9
<212> TYPE: PRT
<213> ORGANISM: Homo sapiens

<400> SEQUENCE: 128

Ala Ala Lys Gly Glu Ala Ala Ala Glu
1               5

<210> SEQ ID NO 129
<211> LENGTH: 9
<212> TYPE: PRT
<213> ORGANISM: Homo sapiens

<400> SEQUENCE: 129

Ala Lys Gly Glu Ala Ala Ala Glu Arg
1               5

<210> SEQ ID NO 130
<211> LENGTH: 9
<212> TYPE: PRT
<213> ORGANISM: Homo sapiens

<400> SEQUENCE: 130

Lys Gly Glu Ala Ala Ala Glu Arg Pro
1               5

<210> SEQ ID NO 131
<211> LENGTH: 9
<212> TYPE: PRT
<213> ORGANISM: Homo sapiens

<400> SEQUENCE: 131

Gly Glu Ala Ala Ala Glu Arg Pro Gly
1               5

<210> SEQ ID NO 132
<211> LENGTH: 9
<212> TYPE: PRT
<213> ORGANISM: Homo sapiens

<400> SEQUENCE: 132

Glu Ala Ala Ala Glu Arg Pro Gly Glu
1               5

<210> SEQ ID NO 133
<211> LENGTH: 9
<212> TYPE: PRT
<213> ORGANISM: Homo sapiens

<400> SEQUENCE: 133

Ala Ala Ala Glu Arg Pro Gly Glu Ala
1               5

<210> SEQ ID NO 134
<211> LENGTH: 9
<212> TYPE: PRT
<213> ORGANISM: Homo sapiens

<400> SEQUENCE: 134

Ala Ala Glu Arg Pro Gly Glu Ala Ala
1               5

<210> SEQ ID NO 135
<211> LENGTH: 9
<212> TYPE: PRT
<213> ORGANISM: Homo sapiens

<400> SEQUENCE: 135

Ala Glu Arg Pro Gly Glu Ala Ala Val

```
1               5

<210> SEQ ID NO 136
<211> LENGTH: 9
<212> TYPE: PRT
<213> ORGANISM: Homo sapiens

<400> SEQUENCE: 136

Glu Arg Pro Gly Glu Ala Ala Val Ala
1               5

<210> SEQ ID NO 137
<211> LENGTH: 8
<212> TYPE: PRT
<213> ORGANISM: Homo sapiens

<400> SEQUENCE: 137

Gly Ala Gln Phe Ser Lys Thr Ala
1               5

<210> SEQ ID NO 138
<211> LENGTH: 8
<212> TYPE: PRT
<213> ORGANISM: Homo sapiens

<400> SEQUENCE: 138

Ala Gln Phe Ser Lys Thr Ala Ala
1               5

<210> SEQ ID NO 139
<211> LENGTH: 8
<212> TYPE: PRT
<213> ORGANISM: Homo sapiens

<400> SEQUENCE: 139

Gln Phe Ser Lys Thr Ala Ala Lys
1               5

<210> SEQ ID NO 140
<211> LENGTH: 8
<212> TYPE: PRT
<213> ORGANISM: Homo sapiens

<400> SEQUENCE: 140

Phe Ser Lys Thr Ala Ala Lys Gly
1               5

<210> SEQ ID NO 141
<211> LENGTH: 8
<212> TYPE: PRT
<213> ORGANISM: Homo sapiens

<400> SEQUENCE: 141

Ser Lys Thr Ala Ala Lys Gly Glu
1               5

<210> SEQ ID NO 142
<211> LENGTH: 8
<212> TYPE: PRT
<213> ORGANISM: Homo sapiens

<400> SEQUENCE: 142

Lys Thr Ala Ala Lys Gly Glu Ala
1               5
```

```
<210> SEQ ID NO 143
<211> LENGTH: 8
<212> TYPE: PRT
<213> ORGANISM: Homo sapiens

<400> SEQUENCE: 143

Thr Ala Ala Lys Gly Glu Ala Ala
1               5

<210> SEQ ID NO 144
<211> LENGTH: 8
<212> TYPE: PRT
<213> ORGANISM: Homo sapiens

<400> SEQUENCE: 144

Ala Ala Lys Gly Glu Ala Ala Ala
1               5

<210> SEQ ID NO 145
<211> LENGTH: 8
<212> TYPE: PRT
<213> ORGANISM: Homo sapiens

<400> SEQUENCE: 145

Ala Lys Gly Glu Ala Ala Ala Glu
1               5

<210> SEQ ID NO 146
<211> LENGTH: 8
<212> TYPE: PRT
<213> ORGANISM: Homo sapiens

<400> SEQUENCE: 146

Lys Gly Glu Ala Ala Ala Glu Arg
1               5

<210> SEQ ID NO 147
<211> LENGTH: 8
<212> TYPE: PRT
<213> ORGANISM: Homo sapiens

<400> SEQUENCE: 147

Gly Glu Ala Ala Ala Glu Arg Pro
1               5

<210> SEQ ID NO 148
<211> LENGTH: 8
<212> TYPE: PRT
<213> ORGANISM: Homo sapiens

<400> SEQUENCE: 148

Glu Ala Ala Ala Glu Arg Pro Gly
1               5

<210> SEQ ID NO 149
<211> LENGTH: 8
<212> TYPE: PRT
<213> ORGANISM: Homo sapiens

<400> SEQUENCE: 149

Ala Ala Ala Glu Arg Pro Gly Glu
1               5

<210> SEQ ID NO 150
```

```
<211> LENGTH: 8
<212> TYPE: PRT
<213> ORGANISM: Homo sapiens

<400> SEQUENCE: 150

Ala Ala Glu Arg Pro Gly Glu Ala
1               5

<210> SEQ ID NO 151
<211> LENGTH: 8
<212> TYPE: PRT
<213> ORGANISM: Homo sapiens

<400> SEQUENCE: 151

Ala Glu Arg Pro Gly Glu Ala Ala
1               5

<210> SEQ ID NO 152
<211> LENGTH: 8
<212> TYPE: PRT
<213> ORGANISM: Homo sapiens

<400> SEQUENCE: 152

Glu Arg Pro Gly Glu Ala Ala Val
1               5

<210> SEQ ID NO 153
<211> LENGTH: 8
<212> TYPE: PRT
<213> ORGANISM: Homo sapiens

<400> SEQUENCE: 153

Arg Pro Gly Glu Ala Ala Val Ala
1               5

<210> SEQ ID NO 154
<211> LENGTH: 7
<212> TYPE: PRT
<213> ORGANISM: Homo sapiens

<400> SEQUENCE: 154

Gly Ala Gln Phe Ser Lys Thr
1               5

<210> SEQ ID NO 155
<211> LENGTH: 7
<212> TYPE: PRT
<213> ORGANISM: Homo sapiens

<400> SEQUENCE: 155

Ala Gln Phe Ser Lys Thr Ala
1               5

<210> SEQ ID NO 156
<211> LENGTH: 7
<212> TYPE: PRT
<213> ORGANISM: Homo sapiens

<400> SEQUENCE: 156

Gln Phe Ser Lys Thr Ala Ala
1               5

<210> SEQ ID NO 157
<211> LENGTH: 7
<212> TYPE: PRT
```

-continued

<213> ORGANISM: Homo sapiens

<400> SEQUENCE: 157

Phe Ser Lys Thr Ala Ala Lys
1               5

<210> SEQ ID NO 158
<211> LENGTH: 7
<212> TYPE: PRT
<213> ORGANISM: Homo sapiens

<400> SEQUENCE: 158

Ser Lys Thr Ala Ala Lys Gly
1               5

<210> SEQ ID NO 159
<211> LENGTH: 7
<212> TYPE: PRT
<213> ORGANISM: Homo sapiens

<400> SEQUENCE: 159

Lys Thr Ala Ala Lys Gly Glu
1               5

<210> SEQ ID NO 160
<211> LENGTH: 7
<212> TYPE: PRT
<213> ORGANISM: Homo sapiens

<400> SEQUENCE: 160

Thr Ala Ala Lys Gly Glu Ala
1               5

<210> SEQ ID NO 161
<211> LENGTH: 7
<212> TYPE: PRT
<213> ORGANISM: Homo sapiens

<400> SEQUENCE: 161

Ala Ala Lys Gly Glu Ala Ala
1               5

<210> SEQ ID NO 162
<211> LENGTH: 7
<212> TYPE: PRT
<213> ORGANISM: Homo sapiens

<400> SEQUENCE: 162

Ala Lys Gly Glu Ala Ala Ala
1               5

<210> SEQ ID NO 163
<211> LENGTH: 7
<212> TYPE: PRT
<213> ORGANISM: Homo sapiens

<400> SEQUENCE: 163

Lys Gly Glu Ala Ala Ala Glu
1               5

<210> SEQ ID NO 164
<211> LENGTH: 7
<212> TYPE: PRT
<213> ORGANISM: Homo sapiens

<400> SEQUENCE: 164

Gly Glu Ala Ala Ala Glu Arg
1               5

<210> SEQ ID NO 165
<211> LENGTH: 7
<212> TYPE: PRT
<213> ORGANISM: Homo sapiens

<400> SEQUENCE: 165

Glu Ala Ala Ala Glu Arg Pro
1               5

<210> SEQ ID NO 166
<211> LENGTH: 7
<212> TYPE: PRT
<213> ORGANISM: Homo sapiens

<400> SEQUENCE: 166

Ala Ala Ala Glu Arg Pro Gly
1               5

<210> SEQ ID NO 167
<211> LENGTH: 7
<212> TYPE: PRT
<213> ORGANISM: Homo sapiens

<400> SEQUENCE: 167

Ala Ala Glu Arg Pro Gly Glu
1               5

<210> SEQ ID NO 168
<211> LENGTH: 7
<212> TYPE: PRT
<213> ORGANISM: Homo sapiens

<400> SEQUENCE: 168

Ala Glu Arg Pro Gly Glu Ala
1               5

<210> SEQ ID NO 169
<211> LENGTH: 7
<212> TYPE: PRT
<213> ORGANISM: Homo sapiens

<400> SEQUENCE: 169

Glu Arg Pro Gly Glu Ala Ala
1               5

<210> SEQ ID NO 170
<211> LENGTH: 7
<212> TYPE: PRT
<213> ORGANISM: Homo sapiens

<400> SEQUENCE: 170

Arg Pro Gly Glu Ala Ala Val
1               5

<210> SEQ ID NO 171
<211> LENGTH: 7
<212> TYPE: PRT
<213> ORGANISM: Homo sapiens

<400> SEQUENCE: 171

Pro Gly Glu Ala Ala Val Ala
1               5

<210> SEQ ID NO 172
<211> LENGTH: 6
<212> TYPE: PRT
<213> ORGANISM: Homo sapiens

<400> SEQUENCE: 172

Gly Ala Gln Phe Ser Lys
1               5

<210> SEQ ID NO 173
<211> LENGTH: 6
<212> TYPE: PRT
<213> ORGANISM: Homo sapiens

<400> SEQUENCE: 173

Ala Gln Phe Ser Lys Thr
1               5

<210> SEQ ID NO 174
<211> LENGTH: 6
<212> TYPE: PRT
<213> ORGANISM: Homo sapiens

<400> SEQUENCE: 174

Gln Phe Ser Lys Thr Ala
1               5

<210> SEQ ID NO 175
<211> LENGTH: 6
<212> TYPE: PRT
<213> ORGANISM: Homo sapiens

<400> SEQUENCE: 175

Phe Ser Lys Thr Ala Ala
1               5

<210> SEQ ID NO 176
<211> LENGTH: 6
<212> TYPE: PRT
<213> ORGANISM: Homo sapiens

<400> SEQUENCE: 176

Ser Lys Thr Ala Ala Lys
1               5

<210> SEQ ID NO 177
<211> LENGTH: 6
<212> TYPE: PRT
<213> ORGANISM: Homo sapiens

<400> SEQUENCE: 177

Lys Thr Ala Ala Lys Gly
1               5

<210> SEQ ID NO 178
<211> LENGTH: 6
<212> TYPE: PRT
<213> ORGANISM: Homo sapiens

<400> SEQUENCE: 178

Thr Ala Ala Lys Gly Glu
1               5

-continued

```
<210> SEQ ID NO 179
<211> LENGTH: 6
<212> TYPE: PRT
<213> ORGANISM: Homo sapiens

<400> SEQUENCE: 179

Ala Ala Lys Gly Glu Ala
1               5

<210> SEQ ID NO 180
<211> LENGTH: 6
<212> TYPE: PRT
<213> ORGANISM: Homo sapiens

<400> SEQUENCE: 180

Ala Lys Gly Glu Ala Ala
1               5

<210> SEQ ID NO 181
<211> LENGTH: 6
<212> TYPE: PRT
<213> ORGANISM: Homo sapiens

<400> SEQUENCE: 181

Lys Gly Glu Ala Ala Ala
1               5

<210> SEQ ID NO 182
<211> LENGTH: 6
<212> TYPE: PRT
<213> ORGANISM: Homo sapiens

<400> SEQUENCE: 182

Gly Glu Ala Ala Ala Glu
1               5

<210> SEQ ID NO 183
<211> LENGTH: 6
<212> TYPE: PRT
<213> ORGANISM: Homo sapiens

<400> SEQUENCE: 183

Glu Ala Ala Ala Glu Arg
1               5

<210> SEQ ID NO 184
<211> LENGTH: 6
<212> TYPE: PRT
<213> ORGANISM: Homo sapiens

<400> SEQUENCE: 184

Ala Ala Ala Glu Arg Pro
1               5

<210> SEQ ID NO 185
<211> LENGTH: 6
<212> TYPE: PRT
<213> ORGANISM: Homo sapiens

<400> SEQUENCE: 185

Ala Ala Glu Arg Pro Gly
1               5
```

```
<210> SEQ ID NO 186
<211> LENGTH: 6
<212> TYPE: PRT
<213> ORGANISM: Homo sapiens

<400> SEQUENCE: 186

Ala Glu Arg Pro Gly Glu
1               5

<210> SEQ ID NO 187
<211> LENGTH: 6
<212> TYPE: PRT
<213> ORGANISM: Homo sapiens

<400> SEQUENCE: 187

Glu Arg Pro Gly Glu Ala
1               5

<210> SEQ ID NO 188
<211> LENGTH: 6
<212> TYPE: PRT
<213> ORGANISM: Homo sapiens

<400> SEQUENCE: 188

Arg Pro Gly Glu Ala Ala
1               5

<210> SEQ ID NO 189
<211> LENGTH: 6
<212> TYPE: PRT
<213> ORGANISM: Homo sapiens

<400> SEQUENCE: 189

Pro Gly Glu Ala Ala Val
1               5

<210> SEQ ID NO 190
<211> LENGTH: 6
<212> TYPE: PRT
<213> ORGANISM: Homo sapiens

<400> SEQUENCE: 190

Gly Glu Ala Ala Val Ala
1               5

<210> SEQ ID NO 191
<211> LENGTH: 5
<212> TYPE: PRT
<213> ORGANISM: Homo sapiens

<400> SEQUENCE: 191

Gly Ala Gln Phe Ser
1               5

<210> SEQ ID NO 192
<211> LENGTH: 5
<212> TYPE: PRT
<213> ORGANISM: Homo sapiens

<400> SEQUENCE: 192

Ala Gln Phe Ser Lys
1               5

<210> SEQ ID NO 193
<211> LENGTH: 5
```

```
<212> TYPE: PRT
<213> ORGANISM: Homo sapiens

<400> SEQUENCE: 193

Gln Phe Ser Lys Thr
1               5

<210> SEQ ID NO 194
<211> LENGTH: 5
<212> TYPE: PRT
<213> ORGANISM: Homo sapiens

<400> SEQUENCE: 194

Phe Ser Lys Thr Ala
1               5

<210> SEQ ID NO 195
<211> LENGTH: 5
<212> TYPE: PRT
<213> ORGANISM: Homo sapiens

<400> SEQUENCE: 195

Ser Lys Thr Ala Ala
1               5

<210> SEQ ID NO 196
<211> LENGTH: 5
<212> TYPE: PRT
<213> ORGANISM: Homo sapiens

<400> SEQUENCE: 196

Lys Thr Ala Ala Lys
1               5

<210> SEQ ID NO 197
<211> LENGTH: 5
<212> TYPE: PRT
<213> ORGANISM: Homo sapiens

<400> SEQUENCE: 197

Thr Ala Ala Lys Gly
1               5

<210> SEQ ID NO 198
<211> LENGTH: 5
<212> TYPE: PRT
<213> ORGANISM: Homo sapiens

<400> SEQUENCE: 198

Ala Ala Lys Gly Glu
1               5

<210> SEQ ID NO 199
<211> LENGTH: 5
<212> TYPE: PRT
<213> ORGANISM: Homo sapiens

<400> SEQUENCE: 199

Ala Lys Gly Glu Ala
1               5

<210> SEQ ID NO 200
<211> LENGTH: 5
<212> TYPE: PRT
<213> ORGANISM: Homo sapiens
```

<400> SEQUENCE: 200

Lys Gly Glu Ala Ala
1               5

<210> SEQ ID NO 201
<211> LENGTH: 5
<212> TYPE: PRT
<213> ORGANISM: Homo sapiens

<400> SEQUENCE: 201

Gly Glu Ala Ala Ala
1               5

<210> SEQ ID NO 202
<211> LENGTH: 5
<212> TYPE: PRT
<213> ORGANISM: Homo sapiens

<400> SEQUENCE: 202

Glu Ala Ala Ala Glu
1               5

<210> SEQ ID NO 203
<211> LENGTH: 5
<212> TYPE: PRT
<213> ORGANISM: Homo sapiens

<400> SEQUENCE: 203

Ala Ala Ala Glu Arg
1               5

<210> SEQ ID NO 204
<211> LENGTH: 5
<212> TYPE: PRT
<213> ORGANISM: Homo sapiens

<400> SEQUENCE: 204

Ala Ala Glu Arg Pro
1               5

<210> SEQ ID NO 205
<211> LENGTH: 5
<212> TYPE: PRT
<213> ORGANISM: Homo sapiens

<400> SEQUENCE: 205

Ala Glu Arg Pro Gly
1               5

<210> SEQ ID NO 206
<211> LENGTH: 5
<212> TYPE: PRT
<213> ORGANISM: Homo sapiens

<400> SEQUENCE: 206

Glu Arg Pro Gly Glu
1               5

<210> SEQ ID NO 207
<211> LENGTH: 5
<212> TYPE: PRT
<213> ORGANISM: Homo sapiens

<400> SEQUENCE: 207

```
Arg Pro Gly Glu Ala
1               5

<210> SEQ ID NO 208
<211> LENGTH: 5
<212> TYPE: PRT
<213> ORGANISM: Homo sapiens

<400> SEQUENCE: 208

Pro Gly Glu Ala Ala
1               5

<210> SEQ ID NO 209
<211> LENGTH: 5
<212> TYPE: PRT
<213> ORGANISM: Homo sapiens

<400> SEQUENCE: 209

Gly Glu Ala Ala Val
1               5

<210> SEQ ID NO 210
<211> LENGTH: 5
<212> TYPE: PRT
<213> ORGANISM: Homo sapiens

<400> SEQUENCE: 210

Glu Ala Ala Val Ala
1               5

<210> SEQ ID NO 211
<211> LENGTH: 4
<212> TYPE: PRT
<213> ORGANISM: Homo sapiens

<400> SEQUENCE: 211

Gly Ala Gln Phe
1

<210> SEQ ID NO 212
<211> LENGTH: 4
<212> TYPE: PRT
<213> ORGANISM: Homo sapiens

<400> SEQUENCE: 212

Ala Gln Phe Ser
1

<210> SEQ ID NO 213
<211> LENGTH: 4
<212> TYPE: PRT
<213> ORGANISM: Homo sapiens

<400> SEQUENCE: 213

Gln Phe Ser Lys
1

<210> SEQ ID NO 214
<211> LENGTH: 4
<212> TYPE: PRT
<213> ORGANISM: Homo sapiens

<400> SEQUENCE: 214

Phe Ser Lys Thr
```

<210> SEQ ID NO 215
<211> LENGTH: 4
<212> TYPE: PRT
<213> ORGANISM: Homo sapiens

<400> SEQUENCE: 215

Ser Lys Thr Ala
1

<210> SEQ ID NO 216
<211> LENGTH: 4
<212> TYPE: PRT
<213> ORGANISM: Homo sapiens

<400> SEQUENCE: 216

Lys Thr Ala Ala
1

<210> SEQ ID NO 217
<211> LENGTH: 4
<212> TYPE: PRT
<213> ORGANISM: Homo sapiens

<400> SEQUENCE: 217

Thr Ala Ala Lys
1

<210> SEQ ID NO 218
<211> LENGTH: 4
<212> TYPE: PRT
<213> ORGANISM: Homo sapiens

<400> SEQUENCE: 218

Ala Ala Lys Gly
1

<210> SEQ ID NO 219
<211> LENGTH: 4
<212> TYPE: PRT
<213> ORGANISM: Homo sapiens

<400> SEQUENCE: 219

Ala Lys Gly Glu
1

<210> SEQ ID NO 220
<211> LENGTH: 4
<212> TYPE: PRT
<213> ORGANISM: Homo sapiens

<400> SEQUENCE: 220

Lys Gly Glu Ala
1

<210> SEQ ID NO 221
<211> LENGTH: 4
<212> TYPE: PRT
<213> ORGANISM: Homo sapiens

<400> SEQUENCE: 221

Gly Glu Ala Ala
1

```
<210> SEQ ID NO 222
<211> LENGTH: 4
<212> TYPE: PRT
<213> ORGANISM: Homo sapiens

<400> SEQUENCE: 222

Glu Ala Ala Ala
1

<210> SEQ ID NO 223
<211> LENGTH: 4
<212> TYPE: PRT
<213> ORGANISM: Homo sapiens

<400> SEQUENCE: 223

Ala Ala Ala Glu
1

<210> SEQ ID NO 224
<211> LENGTH: 4
<212> TYPE: PRT
<213> ORGANISM: Homo sapiens

<400> SEQUENCE: 224

Ala Ala Glu Arg
1

<210> SEQ ID NO 225
<211> LENGTH: 4
<212> TYPE: PRT
<213> ORGANISM: Homo sapiens

<400> SEQUENCE: 225

Ala Glu Arg Pro
1

<210> SEQ ID NO 226
<211> LENGTH: 4
<212> TYPE: PRT
<213> ORGANISM: Homo sapiens

<400> SEQUENCE: 226

Glu Arg Pro Gly
1

<210> SEQ ID NO 227
<211> LENGTH: 4
<212> TYPE: PRT
<213> ORGANISM: Homo sapiens

<400> SEQUENCE: 227

Arg Pro Gly Glu
1

<210> SEQ ID NO 228
<211> LENGTH: 4
<212> TYPE: PRT
<213> ORGANISM: Homo sapiens

<400> SEQUENCE: 228

Pro Gly Glu Ala
1

<210> SEQ ID NO 229
```

<211> LENGTH: 4
<212> TYPE: PRT
<213> ORGANISM: Homo sapiens

<400> SEQUENCE: 229

Gly Glu Ala Ala
1

<210> SEQ ID NO 230
<211> LENGTH: 4
<212> TYPE: PRT
<213> ORGANISM: Homo sapiens

<400> SEQUENCE: 230

Glu Ala Ala Val
1

<210> SEQ ID NO 231
<211> LENGTH: 4
<212> TYPE: PRT
<213> ORGANISM: Homo sapiens

<400> SEQUENCE: 231

Ala Ala Val Ala
1

<210> SEQ ID NO 232
<211> LENGTH: 24
<212> TYPE: PRT
<213> ORGANISM: Artificial Sequence
<220> FEATURE:
<223> OTHER INFORMATION: RNS missense control peptide

<400> SEQUENCE: 232

Gly Thr Ala Pro Ala Ala Glu Gly Ala Gly Ala Glu Val Lys Arg Ala
1               5                   10                  15

Ser Ala Glu Ala Lys Gln Ala Phe
            20

<210> SEQ ID NO 233
<211> LENGTH: 10
<212> TYPE: PRT
<213> ORGANISM: Artificial Sequence
<220> FEATURE:
<223> OTHER INFORMATION: RNS2 missense control peptide

<400> SEQUENCE: 233

Gly Lys Ala Ser Gln Phe Ala Lys Thr Ala
1               5                   10

<210> SEQ ID NO 234
<211> LENGTH: 11
<212> TYPE: PRT
<213> ORGANISM: Artificial Sequence
<220> FEATURE:
<223> OTHER INFORMATION: mutated MANS peptide fragment

<400> SEQUENCE: 234

Arg Gly Ala Gln Phe Ser Lys Thr Ala Ala Lys
1               5                   10

<210> SEQ ID NO 235
<211> LENGTH: 5
<212> TYPE: PRT
<213> ORGANISM: Artificial Sequence
<220> FEATURE:

<223> OTHER INFORMATION: mutated MANS peptide fragment

<400> SEQUENCE: 235

Arg Ala Lys Gly Glu
1               5

<210> SEQ ID NO 236
<211> LENGTH: 1885
<212> TYPE: DNA
<213> ORGANISM: Homo sapiens
<220> FEATURE:
<221> NAME/KEY: CDS
<222> LOCATION: (309)..(1307)

<400> SEQUENCE: 236

```
tttattactt cttttttttt cgaactacac ttgggctcct ttttttgtgc tcgactttc     60 cacccttttt ccctccctcc tgtgctgctg cttttgatc tcttcgacta aaattttttt   120
atccggagtg tatttaatcg gttctgttct gtcctctcca ccaccccac ccccctccct   180 ccggtgtgtg tgccgctgcc gctgttgccg ccgccgctgc tgctgctgct cgcccgtcg   240 ttacaccaac ccgaggctct ttgtttcccc tcttggatct gttgagtttc tttgttgaag  300 aagccagc atg ggt gcc cag ttc tcc aag acc gca gcg aag gga gaa gcc   350
         Met Gly Ala Gln Phe Ser Lys Thr Ala Ala Lys Gly Glu Ala
         1               5                   10 gcc gcg gag agg cct ggg gag gcg gct gtg gcc tcg tcg cct tcc aaa    398
Ala Ala Glu Arg Pro Gly Glu Ala Ala Val Ala Ser Ser Pro Ser Lys
15                  20                  25                  30 gcg aac gga cag gag aat ggc cac gtg aag gta aac ggc gac gct tcg    446
Ala Asn Gly Gln Glu Asn Gly His Val Lys Val Asn Gly Asp Ala Ser
                35                  40                  45 ccc gcg gcc gcc gag tcg ggc gcc aag gag gag ctg cag gcc aac ggc    494
Pro Ala Ala Ala Glu Ser Gly Ala Lys Glu Glu Leu Gln Ala Asn Gly
            50                  55                  60 agc gcc ccg gcc gcc gac aag gag gag ccc gcg gcc gcc ggg agc ggg    542
Ser Ala Pro Ala Ala Asp Lys Glu Glu Pro Ala Ala Ala Gly Ser Gly
        65                  70                  75 gcg gcg tcg ccc tcc gcg gcc gag aaa ggt gag ccg gcc gcc gcc gct    590
Ala Ala Ser Pro Ser Ala Ala Glu Lys Gly Glu Pro Ala Ala Ala Ala
    80                  85                  90 gcc ccc gag gcc ggg gcc agc ccg gta gag aag gag gcc ccc gcg gaa    638
Ala Pro Glu Ala Gly Ala Ser Pro Val Glu Lys Glu Ala Pro Ala Glu
95                  100                 105                 110 ggc gag gct gcc gag ccc ggc tcg ccc acg gcc gcg gag gga gag gcc    686
Gly Glu Ala Ala Glu Pro Gly Ser Pro Thr Ala Ala Glu Gly Glu Ala
                115                 120                 125 gcg tcg gcc gcc tcc tcg act tct tcg ccc aag gcc gag gac ggg gcc    734
Ala Ser Ala Ala Ser Ser Thr Ser Ser Pro Lys Ala Glu Asp Gly Ala
            130                 135                 140 acg ccc tcg ccc agc aac gag acc ccg aaa aaa aaa aag aag cgc ttt    782
Thr Pro Ser Pro Ser Asn Glu Thr Pro Lys Lys Lys Lys Lys Arg Phe
        145                 150                 155 tcc ttc aag aag tct ttc aag ctg agc ggc ttc tcc ttc aag aag aac    830
Ser Phe Lys Lys Ser Phe Lys Leu Ser Gly Phe Ser Phe Lys Lys Asn
    160                 165                 170 aag aag gag gct gga gaa ggc ggt gag gct gag gcg ccc gct gcc gaa    878
Lys Lys Glu Ala Gly Glu Gly Gly Glu Ala Glu Ala Pro Ala Ala Glu
175                 180                 185                 190 ggc ggc aag gac gag gcc gcc ggg ggc gca gct gcg gcc gcc gcc gag    926
Gly Gly Lys Asp Glu Ala Ala Gly Gly Ala Ala Ala Ala Ala Ala Glu
                195                 200                 205
```

| | | | | | | | | | | | | | | | |
|---|---|---|---|---|---|---|---|---|---|---|---|---|---|---|---|
| gcg | ggc | gcg | gcc | tcc | ggg | gag | cag | gca | gcg | gcg | ccg | ggc | gag | gag | gca | 974
| Ala | Gly | Ala | Ala | Ser | Gly | Glu | Gln | Ala | Ala | Ala | Pro | Gly | Glu | Glu | Ala |
| | | 210 | | | | | 215 | | | | | 220 | | | |

```
gcg ggc gcg gcc tcc ggg gag cag gca gcg gcg ccg ggc gag gag gca    974
Ala Gly Ala Ala Ser Gly Glu Gln Ala Ala Ala Pro Gly Glu Glu Ala
            210                 215                 220 gca gcg ggc gag gag ggg gcg gcg ggt ggc gac tcg cag gag gcc aag   1022
Ala Ala Gly Glu Glu Gly Ala Ala Gly Gly Asp Ser Gln Glu Ala Lys
                225                 230                 235 ccc cag gag gcc gct gtc gcg cca gag aag ccg ccc gcc agc gac gag   1070
Pro Gln Glu Ala Ala Val Ala Pro Glu Lys Pro Pro Ala Ser Asp Glu
        240                 245                 250 acc aag gcc gcc gag gag ccc agc aag gtg gag gag aaa aag gcc gag   1118
Thr Lys Ala Ala Glu Glu Pro Ser Lys Val Glu Glu Lys Lys Ala Glu
255                 260                 265                 270 gag gcc ggg gcc agc gcc gcc gcc tgc gag gcc ccc tcc gcc gcc ggg   1166
Glu Ala Gly Ala Ser Ala Ala Ala Cys Glu Ala Pro Ser Ala Ala Gly
                275                 280                 285 ctg gtg tgc ccc cgg aga gga ggc agc ccc cgc gga gga gcc cgc ggc   1214
Leu Val Cys Pro Arg Arg Gly Gly Ser Pro Arg Gly Gly Ala Arg Gly
            290                 295                 300 cgc cgc agc ctc aat caa gcc tgc gca gcc ccc tca cag gag gcc cag   1262
Arg Arg Ser Leu Asn Gln Ala Cys Ala Ala Pro Ser Gln Glu Ala Gln
                    305                 310                 315 ccc gag tgc agt cca gaa gcc ccc cca gcg gag gcg gca gag taa       1307
Pro Glu Cys Ser Pro Glu Ala Pro Pro Ala Glu Ala Ala Glu
                320                 325                 330 aagagcaagc ttttgtgaga taatcgaaga acatttctc ccccgtttgt ttggttggag   1367
tggtgccagg tactggattt tggagaactt gtctacaacc agggattgat tttaaagatg   1427
tcttttttta ttttactttt ttttaagcac caaattttgt tgttttttt ttctcccctc    1487 cccacagatc ccatctcaaa tcattctgtt aaccaccatt ccaacaggtc gaggagagct   1547
taaacacctt cttcctctgg ccttgtttct cttttatttt ttatttttc gcatcagtat     1607 taatgttttt gcatactttg catctttatt caaaagtgta aactttcttt gtcaatctat    1667
ggacatgccc atatatgaag gagatgggtg ggtcaaaaag ggatatcaaa tgaagtgata    1727
ggggtcacaa tggggaaatt gaagtggtgc ataacattgc caaaatagtg tgccactaga    1787
aatggtgtaa aggctgtctt ttttttttt tttaaagaaa agttattacc atgtattttg      1847
tgaggcaggt ttacaacact acaactcgtg ccgaattc                             1885
```

<210> SEQ ID NO 237
<211> LENGTH: 332
<212> TYPE: PRT
<213> ORGANISM: Homo sapiens

<400> SEQUENCE: 237

```
Met Gly Ala Gln Phe Ser Lys Thr Ala Ala Lys Gly Glu Ala Ala Ala
1               5                   10                  15

Glu Arg Pro Gly Glu Ala Ala Val Ala Ser Ser Pro Ser Lys Ala Asn
            20                  25                  30

Gly Gln Glu Asn Gly His Val Lys Val Asn Gly Asp Ala Ser Pro Ala
        35                  40                  45

Ala Ala Glu Ser Gly Ala Lys Glu Glu Leu Gln Ala Asn Gly Ser Ala
    50                  55                  60

Pro Ala Ala Asp Lys Glu Glu Pro Ala Ala Gly Ser Gly Ala Ala
65                  70                  75                  80

Ser Pro Ser Ala Ala Glu Lys Gly Glu Pro Ala Ala Ala Ala Pro
                85                  90                  95
```

-continued

```
Glu Ala Gly Ala Ser Pro Val Glu Lys Glu Ala Pro Ala Glu Gly Glu
                100                 105                 110

Ala Ala Glu Pro Gly Ser Pro Thr Ala Ala Gly Glu Ala Ala Ser
        115                 120                 125

Ala Ala Ser Ser Thr Ser Ser Pro Lys Ala Glu Asp Gly Ala Thr Pro
    130                 135                 140

Ser Pro Ser Asn Glu Thr Pro Lys Lys Lys Lys Arg Phe Ser Phe
145                 150                 155                 160

Lys Lys Ser Phe Lys Leu Ser Gly Phe Ser Phe Lys Lys Asn Lys Lys
                165                 170                 175

Glu Ala Gly Glu Gly Gly Glu Ala Glu Ala Pro Ala Ala Glu Gly Gly
            180                 185                 190

Lys Asp Glu Ala Ala Gly Gly Ala Ala Ala Ala Ala Glu Ala Gly
        195                 200                 205

Ala Ala Ser Gly Glu Gln Ala Ala Pro Gly Glu Glu Ala Ala Ala
    210                 215                 220

Gly Glu Glu Gly Ala Ala Gly Gly Asp Ser Gln Glu Ala Lys Pro Gln
225                 230                 235                 240

Glu Ala Ala Val Ala Pro Glu Lys Pro Pro Ala Ser Asp Glu Thr Lys
                245                 250                 255

Ala Ala Glu Glu Pro Ser Lys Val Glu Glu Lys Lys Ala Glu Glu Ala
            260                 265                 270

Gly Ala Ser Ala Ala Ala Cys Glu Ala Pro Ser Ala Ala Gly Leu Val
        275                 280                 285

Cys Pro Arg Arg Gly Gly Ser Pro Arg Gly Ala Arg Gly Arg Arg
    290                 295                 300

Ser Leu Asn Gln Ala Cys Ala Ala Pro Ser Gln Glu Ala Gln Pro Glu
305                 310                 315                 320

Cys Ser Pro Glu Ala Pro Pro Ala Glu Ala Glu
                325                 330

<210> SEQ ID NO 238
<211> LENGTH: 2589
<212> TYPE: DNA
<213> ORGANISM: Homo sapiens
<220> FEATURE:
<221> NAME/KEY: CDS
<222> LOCATION: (370)..(1368)

<400> SEQUENCE: 238
caaccaggga gatttctcca ttttcctctct gtctacagtg cggctacaaa tctgggattt       60
ttttattact tcttttttttt tcgaactaca cttgggctcc ttttttttgtg ctcgactttt     120 ccaccctttt tccctccctc ctgtgctgct gcttttgat ctcttcgact aaaattttt        180 tatccggagt gtatttaatc ggttctgttc tgtcctctcc accacccca cccccctccc       240 tccggtgtgt gtgccgctgc cgctgttgcc gccgccgctg ctgctgctgc tgcccccgtc      300
gttacaccaa cccgaggctc tttgtttccc ctcttggatc tgttgagttt ctttgttgaa      360 gaagccagc atg ggt gcc cag ttc tcc aag acc gca gcg aag gga gaa gcc      411
          Met Gly Ala Gln Phe Ser Lys Thr Ala Ala Lys Gly Glu Ala
            1               5                   10 gcc gcg gag agg cct ggg gag gcg gct gtg gcc tcg tcg cct tcc aaa        459
Ala Ala Glu Arg Pro Gly Glu Ala Ala Val Ala Ser Ser Pro Ser Lys
 15                  20                  25                  30 gcg aac gga cag gag aat ggc cac gtg aag gta aac ggc gac gct tcg        507
Ala Asn Gly Gln Glu Asn Gly His Val Lys Val Asn Gly Asp Ala Ser
                 35                  40                  45
```

| | | |
|---|---|---|
| ccc gcg gcc gcc gag tcg ggc gcc aag gag gag ctg cag gcc aac ggc<br>Pro Ala Ala Ala Glu Ser Gly Ala Lys Glu Glu Leu Gln Ala Asn Gly<br>50 55 60 | | 555 |
| agc gcc ccg gcc gcc gac aag gag gag ccc gcg gcc gcc ggg agc ggg<br>Ser Ala Pro Ala Ala Asp Lys Glu Glu Pro Ala Ala Ala Gly Ser Gly<br>65 70 75 | | 603 |
| gcg gcg tcg ccc tcc tcg gcc gag aaa ggt gag ccg gcc gcc gcc gct<br>Ala Ala Ser Pro Ser Ser Ala Glu Lys Gly Glu Pro Ala Ala Ala Ala<br>80 85 90 | | 651 |
| gcc ccc gag gcc ggg gcc agc ccg gta gag aag gag gcc ccc gcg gaa<br>Ala Pro Glu Ala Gly Ala Ser Pro Val Glu Lys Glu Ala Pro Ala Glu<br>95 100 105 110 | | 699 |
| ggc gag gct gcc gag ccc ggc tcg gcc acg gcc gcg gag gga gag gcc<br>Gly Glu Ala Ala Glu Pro Gly Ser Ala Thr Ala Ala Glu Gly Glu Ala<br>115 120 125 | | 747 |
| gcg tcg gcc gcc tcc tcg act tct tcg ccc aag gcc gag gac ggg gcc<br>Ala Ser Ala Ala Ser Ser Thr Ser Ser Pro Lys Ala Glu Asp Gly Ala<br>130 135 140 | | 795 |
| acg ccc tcg ccc agc aac gag acc ccg aaa aaa aaa aag aag cgc ttt<br>Thr Pro Ser Pro Ser Asn Glu Thr Pro Lys Lys Lys Lys Lys Arg Phe<br>145 150 155 | | 843 |
| tcc ttc aag aag tct ttc aag ctg agc ggc ttc tcc ttc aag aag aac<br>Ser Phe Lys Lys Ser Phe Lys Leu Ser Gly Phe Ser Phe Lys Lys Asn<br>160 165 170 | | 891 |
| aag aag gag gct gga gaa ggc ggt gag gct gag gcg ccc gct gcc gaa<br>Lys Lys Glu Ala Gly Glu Gly Gly Glu Ala Glu Ala Pro Ala Ala Glu<br>175 180 185 190 | | 939 |
| ggc ggc aag gac gag gcc gcc ggg ggc gca gct gcg gcc gcc gcc gag<br>Gly Gly Lys Asp Glu Ala Ala Gly Gly Ala Ala Ala Ala Ala Ala Glu<br>195 200 205 | | 987 |
| gcg ggc gcg gcc tcc ggg gag cag gca gcg gcg ccg ggc gag gag gcg<br>Ala Gly Ala Ala Ser Gly Glu Gln Ala Ala Ala Pro Gly Glu Glu Ala<br>210 215 220 | | 1035 |
| gca gcg ggc gag gag ggg gcg gcg ggt ggc gac ccg cag gag gcc aag<br>Ala Ala Gly Glu Glu Gly Ala Ala Gly Gly Asp Pro Gln Glu Ala Lys<br>225 230 235 | | 1083 |
| ccc cag gag gcc gct gtc gcg cca gag aag ccg ccc gcc agc gac gag<br>Pro Gln Glu Ala Ala Val Ala Pro Glu Lys Pro Pro Ala Ser Asp Glu<br>240 245 250 | | 1131 |
| acc aag gcc gcc gag gag ccc agc aag gtg gag gag aaa aag gcc gag<br>Thr Lys Ala Ala Glu Glu Pro Ser Lys Val Glu Glu Lys Lys Ala Glu<br>255 260 265 270 | | 1179 |
| gag gcc ggg gcc agc gcc gcc gcc tgc gag gcc ccc tcc gcc gcc ggg<br>Glu Ala Gly Ala Ser Ala Ala Ala Cys Glu Ala Pro Ser Ala Ala Gly<br>275 280 285 | | 1227 |
| ccc ggc gcg ccc ccg gag cag gag gca gcc ccc gcg gag gag ccc gcg<br>Pro Gly Ala Pro Pro Glu Gln Glu Ala Ala Pro Ala Glu Glu Pro Ala<br>290 295 300 | | 1275 |
| gcc gcc gca gcc tcg tca gcc tgc gca gcc ccc tca cag gag gcc cag<br>Ala Ala Ala Ala Ser Ser Ala Cys Ala Ala Pro Ser Gln Glu Ala Gln<br>305 310 315 | | 1323 |
| ccc gag tgc agt cca gaa gcc ccc cca gcg gag gcg gca gag taa<br>Pro Glu Cys Ser Pro Glu Ala Pro Pro Ala Glu Ala Ala Glu<br>320 325 330 | | 1368 |
| aagagcaagc ttttgtgaga taatcgaaga acttttctcc cccgtttgtt tgttggagtg | | 1428 |
| gtgccaggta ctgttttgga gaacttgtct acaaccaggg attgatttta aagatgtctt | | 1488 |
| tttttatttt acttttttttt aagcaccaaa ttttgttgtt ttttttttc tccctcccc | | 1548 |

```
acagatccca tctcaaatca ttctgttaac caccattcca acaggtcgag gagagcttaa    1608
acaccttctt cctctgcctt gtttctcttt tattttttat tttttcgcat cagtattaat    1668
gtttttgcat actttgcatc tttattcaaa agtgtaaact ttctttgtca atctatggac    1728
atgcccatat atgaaggaga tgggtgggtc aaaaagggat atcaaatgaa gtgatagggg    1788
tcacaatggg gaaattgaag tggtgcataa cattgccaaa atagtgtgcc actagaaatg    1848
gtgtaaaggc tgtctttttt ttttttttta agaaaagtt attaccatgt attttgtgag     1908
gcaggtttac aacactacaa gtcttgagtt aagaaggaaa gaggaaaaaa gaaaaaacac    1968
caatacccag atttaaaaaa aaaaaaacga tcatagtctt aggagttcat ttaaaccata    2028 ggaactttc acttatctca tgttagctgt accagtcagt gattaagtag aactacaagt     2088
tgtataggct ttattgttta ttgctggttt atgaccttaa taaagtgtaa ttatgtatta    2148
ccagcagggt gttttaact gtgactattg tataaaaaca aatcttgata tccagaagca     2208
catgaagttt gcaactttcc accctgccca tttttgtaaa actgcagtca tcttggacct    2268
tttaaaacac aaattttaaa ctcaaccaag ctgtgataag tggaatggtt actgtttata    2328
ctgtggtatg tttttgatta cagcagataa tgctttcttt tccagtcgtc tttgagaata    2388
aaggaaaaaa aatcttcaga tgcaatggtt ttgtgtagca tcttgtctat catgttttgt    2448
aaatactgga gaagctttga ccaatttgac ttagagatgg aatgtaactt tgcttacaaa    2508
aattgctatt aaactcctgc ttaaggtgtt ctaattttct gtgagcacac taaaagcgaa    2568
aaataaatgt gaataaaatg t                                              2589
```

<210> SEQ ID NO 239
<211> LENGTH: 332
<212> TYPE: PRT
<213> ORGANISM: Homo sapiens

<400> SEQUENCE: 239

```
Met Gly Ala Gln Phe Ser Lys Thr Ala Ala Lys Gly Glu Ala Ala Ala
1               5                   10                  15

Glu Arg Pro Gly Glu Ala Ala Val Ala Ser Ser Pro Ser Lys Ala Asn
            20                  25                  30

Gly Gln Glu Asn Gly His Val Lys Val Asn Gly Asp Ala Ser Pro Ala
        35                  40                  45

Ala Ala Glu Ser Gly Ala Lys Glu Glu Leu Gln Ala Asn Gly Ser Ala
    50                  55                  60

Pro Ala Ala Asp Lys Glu Glu Pro Ala Ala Gly Ser Gly Ala Ala
65                  70                  75                  80

Ser Pro Ser Ser Ala Glu Lys Gly Glu Pro Ala Ala Ala Ala Pro
                85                  90                  95

Glu Ala Gly Ala Ser Pro Val Glu Lys Glu Ala Pro Ala Glu Gly Glu
            100                 105                 110

Ala Ala Glu Pro Gly Ser Ala Thr Ala Ala Gly Glu Ala Ala Ser
        115                 120                 125

Ala Ala Ser Ser Thr Ser Ser Pro Lys Ala Glu Asp Gly Ala Thr Pro
    130                 135                 140

Ser Pro Ser Asn Glu Thr Pro Lys Lys Lys Lys Arg Phe Ser Phe
145                 150                 155                 160

Lys Lys Ser Phe Lys Leu Ser Gly Phe Ser Phe Lys Lys Asn Lys Lys
                165                 170                 175

Glu Ala Gly Glu Gly Gly Glu Ala Glu Ala Pro Ala Ala Glu Gly Gly
            180                 185                 190
```

```
Lys Asp Glu Ala Ala Gly Gly Ala Ala Ala Ala Ala Glu Ala Gly
    195                 200                 205

Ala Ala Ser Gly Glu Gln Ala Ala Ala Pro Gly Glu Glu Ala Ala Ala
    210                 215                 220

Gly Glu Glu Gly Ala Ala Gly Gly Asp Pro Gln Glu Ala Lys Pro Gln
225                 230                 235                 240

Glu Ala Ala Val Ala Pro Glu Lys Pro Pro Ala Ser Asp Glu Thr Lys
                245                 250                 255

Ala Ala Glu Glu Pro Ser Lys Val Glu Glu Lys Lys Ala Glu Glu Ala
                260                 265                 270

Gly Ala Ser Ala Ala Ala Cys Glu Ala Pro Ser Ala Ala Gly Pro Gly
            275                 280                 285

Ala Pro Pro Glu Gln Glu Ala Ala Pro Ala Glu Glu Pro Ala Ala Ala
        290                 295                 300

Ala Ala Ser Ser Ala Cys Ala Ala Pro Ser Gln Glu Ala Gln Pro Glu
305                 310                 315                 320

Cys Ser Pro Glu Ala Pro Pro Ala Glu Ala Ala Glu
                325                 330

<210> SEQ ID NO 240
<211> LENGTH: 10
<212> TYPE: PRT
<213> ORGANISM: Artificial Sequence
<220> FEATURE:
<223> OTHER INFORMATION: mutated MANS peptide fragment

<400> SEQUENCE: 240

Arg Gly Ala Gln Phe Ser Lys Thr Ala Ala
1               5                   10
```